US012790330B2

(12) United States Patent
Alvaro et al.

(10) Patent No.: US 12,790,330 B2
(45) Date of Patent: Nov. 10, 2026

(54) POTASSIUM CHANNEL MODULATORS

(71) Applicant: Autifony Therapeutics Limited, Hertfordshire (GB)

(72) Inventors: Giuseppe Alvaro, Stevenage (GB); Agostino Marasco, Stevenage (GB); Dean Rivers, Stevenage (GB)

(73) Assignee: Autifony Therapeutics Limited, Hertfordshire (GB)

( * ) Notice: Subject to any disclaimer, the term of this patent is extended or adjusted under 35 U.S.C. 154(b) by 333 days.

(21) Appl. No.: 18/681,686

(22) PCT Filed: Aug. 10, 2022

(86) PCT No.: PCT/GB2022/052083
§ 371 (c)(1),
(2) Date: Feb. 6, 2024

(87) PCT Pub. No.: WO2023/017263
PCT Pub. Date: Feb. 16, 2023

(65) Prior Publication Data

US 2024/0327406 A1 Oct. 3, 2024

(30) Foreign Application Priority Data

Aug. 10, 2021 (EP) ..................................... 21190704

(51) Int. Cl.

| | |
|---|---|
| ***C07D 471/04*** | (2006.01) |
| ***A61K 9/20*** | (2006.01) |
| ***A61K 9/48*** | (2006.01) |
| ***A61K 31/444*** | (2006.01) |
| ***A61K 31/506*** | (2006.01) |
| ***A61P 27/16*** | (2006.01) |

(52) U.S. Cl.
CPC .......... *C07D 471/04* (2013.01); *A61K 9/2009* (2013.01); *A61K 9/2054* (2013.01); *A61K 9/2059* (2013.01); *A61K 9/485* (2013.01); *A61K 9/4858* (2013.01); *A61K 9/4866* (2013.01); *A61K 31/444* (2013.01); *A61K 31/506* (2013.01); *A61P 27/16* (2018.01)

(58) Field of Classification Search
CPC ..... C07D 471/04; A61P 27/16; A61K 31/444; A61K 31/506
See application file for complete search history.

(56) References Cited

U.S. PATENT DOCUMENTS

| | | |
|---|---|---|
| 3,759,933 A | 9/1973 | Mullen et al. |
| 2020/0131156 A1 | 4/2020 | Sams et al. |

FOREIGN PATENT DOCUMENTS

| | | | | |
|---|---|---|---|---|
| EP | 3901152 A1 | 10/2021 | | |
| WO | WO 2008/046135 A1 | 4/2008 | | |
| WO | WO 2011/069951 A1 | 6/2011 | | |
| WO | WO 2011/163355 | 12/2011 | | |
| WO | WO 2012/076877 A1 | 6/2012 | | |
| WO | WO 2012/151640 A1 | 11/2012 | | |
| WO | WO 2012/168710 A1 | 12/2012 | | |
| WO | WO 2013/083994 A1 | 6/2013 | | |
| WO | WO 2013/175215 A1 | 11/2013 | | |
| WO | WO 2017/098254 A1 | 6/2017 | | |
| WO | WO 2017/103604 A1 | 6/2017 | | |
| WO | WO 2018/020263 A1 | 2/2018 | | |
| WO | WO 2018/109484 A1 | 6/2018 | | |
| WO | WO 2021/156584 A1 | 8/2018 | | |
| WO | WO 2019/222816 A1 | 11/2019 | | |
| WO | WO 2020/000065 A2 | 1/2020 | | |
| WO | WO 2020/079422 A1 | 4/2020 | | |
| WO | WO 2020/111263 | 6/2020 | | |
| WO | WO 2021/056048 A1 | 4/2021 | | |
| WO | WO 2021214090 | * | 10/2021 | ........... C07D 471/04 |
| WO | WO 2024/086061 A2 | 4/2024 | | |
| WO | WO 2024/121552 A1 | 6/2024 | | |

OTHER PUBLICATIONS

"Fragile X Syndrome (FXS)," Cleveland Clinic, Updated Feb. 7, 2024, Accessed Mar. 5, 2026 via <https://my.clevelandclinic.org/health/diseases/5476-fragile-x-syndrome#prevention>.*

Gündüz et al., "1,3-Disubstituted urea derivatives: Synthesis, anti-microbial activity evaluation and in silico studies", Bioorg. Chem., vol. 102, Art. 104104, pp. 1-9 (Sep. 2020).

Prasad et al., "Synthesis and biological evaluation of 1-benzyl-N-(2-(phenylamino)pyridin-3-yl)-1H-1,2,3-triazole-4-carboxamides as antimitotic agents", Bioorg Chem., vol. 83, pp. 535-548 (Nov. 2018).

Sarada et al., "Pure blue phosphorescence by new N-heterocyclic carbene-based Ir(III) Complexes for organic light-emitting diode application", Dyes and Pigments, vol. 150, pp. 1-8 (Mar. 2018).

Yutilov et al., "Synthesis of 1- and 3-substituted imidazo[4,5-b]pyridine-2-ones", Russ J. Org. Chem., vol. 42, No. 6, pp. 897-900 (Jun. 2006).

* cited by examiner

*Primary Examiner* — Alicia L Otton

(74) *Attorney, Agent, or Firm* — McDermott Will & Schulte LLP; Brennen P. Baylor; Margaret Sampson

(57) ABSTRACT

Ion channel modulator compounds of the formula: (Formula (I)), and related aspects.

(I)

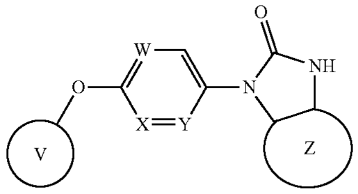

4 Claims, No Drawings

POTASSIUM CHANNEL MODULATORS

CROSS-REFERENCE TO RELATED APPLICATIONS

This application is a U.S. National Stage Application under 35 U.S.C. § 371 which claims the benefit of priority to International Patent Application No. PCT/GB2022/052083, filed Aug. 10, 2022, which claims the benefit of priority to GB Patent Application No. 21190704.3 filed Aug. 10, 2021, each of which is hereby incorporated by reference in its entirety.

TECHNICAL FIELD

This invention relates to novel compounds, pharmaceutical compositions containing them and their use as medicaments, in particular in the prophylaxis or treatment of progressive myoclonic epilepsy, including PME associated with mutations in the KCNC1 gene, hearing disorders, including hearing loss and tinnitus, as well as Fragile X syndrome, schizophrenia, substance abuse disorders, and pain.

BACKGROUND TO THE INVENTION

The Kv3 voltage-gated potassium channel family includes four members, Kv3.1, Kv3.2, Kv3.3, and Kv3.4. Kv3 channels are activated by depolarisation of the plasma membrane to voltages more positive than −20 mV; furthermore, the channels deactivate rapidly upon repolarisation of the membrane. These biophysical properties ensure that the channels open towards the peak of the depolarising phase of the neuronal action potential to initiate repolarisation. Rapid termination of the action potential mediated by Kv3 channels allows the neuron to recover more quickly to reach sub-threshold membrane potentials from which further action potentials can be triggered. As a result, the presence of Kv3 channels in certain neurons contributes to their ability to fire at high frequencies (Rudy et al., 2001). Kv3 subtypes are predominant in the CNS, although Kv3.1, Kv3.3 and Kv3.4 channels are also found in spinal cord (Brooke et al., 2002; 2004; 2006). Kv3 channel subtypes are differentially expressed by sub-classes of interneurons in cortical and hippocampal brain areas (e.g. Chow et al., 1999; Martina et al., 1998; McDonald et al., 2006; Chang et al., 2007), in the thalamus (e.g. Kasten et al., 2007), cerebellum (e.g. Sacco et al., 2006; Puente et al., 2010), and auditory brain stem nuclei (Li et al., 2001).

Characterisation of mice in which one or more of the Kv3 subtypes has been deleted shows that the absence of Kv3.1 gives rise to increased locomotor activity, altered electroencephalographic activity, and a fragmented sleep pattern (Joho et al., 1999). The deletion of Kv3.2 leads to a reduction in seizure threshold and altered cortical electroencephalographic activity (Lau et al., 2000). Deletion of Kv3.3 is associated with mild ataxia and motor deficits (McMahon et al., 2004). Double deletion of Kv3.1 and Kv3.3 gives rise to a severe phenotype characterised by spontaneous seizures, ataxia, and an increased sensitivity to the effects of ethanol (Espinosa et al., 2001; Espinosa et al., 2008). A spontaneous mutation in the Kv3.1 gene (KCNC1) in humans causes progressive myoclonic epilepsy (Muona et al., 2014). Mutations of the Kv3.3 gene (KCNC3) in humans is associated with spinocerebellar ataxia (SCA13) (Figueroa et al., 2010).

Bipolar disorder, schizophrenia, are serious disorders of the central nervous system that have been associated with reduced function of parvalbumin-positive inhibitory interneurons in corticolimbic brain circuits (Reynolds et al., 2004; Benes et al., 2008; Brambilla et al., 2003; Aroniadou-Anderjaska et al., 2007; Ben-Ari, 2006). Parvalbumin positive basket cells express Kv3 channels which allow these neurons to fire at high frequency to provide fast feedback inhibition within local circuits (Markram et al., 2004). Accurate timing of this inhibitory feedback is necessary to sustain network synchronisation, for example, in the generation of gamma frequency field potential oscillations that have been associated with cognitive function (Fisahn et al., 2005; Engel et al., 2001). A reduction in gamma oscillations has been observed in patients with schizophrenia (Spencer et al., 2004), and evidence suggests reduced expression of Kv3.1, but not Kv3.2 in the dorsolateral prefrontal cortex of patients with schizophrenia (Yanagi et al., 2014). Positive modulators of Kv3 channels enhance the firing of parvalbumin positive interneurons (Rosato-Siri et al., 2015; Boddum et al., 2017) leading to increased gamma oscillations (Andrade-Talavera et al., 2020) and rescue deficits in cognitive and social behaviours in animal models (Leger et al., 2015). Furthermore, Kv3 positive modulators reduced abonormal behaviours in a mouse model of bipolar disorder (Parekh et al., 2017)

Fragile X syndrome is a paediatric developmental disorder with autistic features that has also been linked to dysfunction of parvalbumin positive interneurons (e.g. Pirbhoy et al., 2020) and alteration of Kv3.1 channel expression (Darnell et al., 2001; Strumbos et al., 2010). Kv3 channel modulators have been shown to rescue deficits in auditory brainstem function in vitro and in vivo in a mouse model of Fragile X syndrome (El-Hassar et al., 2019).

Voltage-gated ion channels of the Kv3 family are expressed at high levels in auditory brainstem nuclei (Li et al., 2001) where they permit the fast firing of neurons that transmit auditory information from the cochlear to higher brain regions. Phosphorylation of Kv3.1 and Kv3.3 channels in auditory brainstem neurons is suggested to contribute to the rapid physiological adaptation to sound levels that may play a protective role during exposure to noise (Desai et al., 2008; Song et al., 2005). Loss of Kv3.1 channel expression in central auditory neurons is observed in hearing impaired mice (von Hehn et al., 2004); furthermore, a decline in Kv3.1 expression may be associated with loss of hearing in aged mice (Jung et al. 2005), and loss of Kv3 channel function may also follow noise-trauma induced hearing loss (Pilati et al., 2012). Furthermore, pathological plasticity of auditory brainstem networks is likely to contribute to symptoms that are experienced by many people suffering from hearing loss of different types. Recent studies have shown that regulation of Kv3.1 channel function and expression has a major role in controlling auditory neuron excitability (Kaczmarek et al., 2005; Anderson et al., 2018; Glait et al., 2018; Olsen et al., 2018, Chambers et al., 2017), suggesting that this mechanism could account for some of the plastic changes that give rise to hearing-related disorders such as tinnitus.

Recently, Kv3.4 channels have become a target of interest for the treatment of chronic pain. Kv3.4 channels are expressed on neurons of the dorsal root ganglia (Ritter et al., 2012; Chien et al., 2007), where they are predominantly expressed on sensory C-fibres (Chien et al., 2007). Kv3 channels are also expressed by specific subsets of neurons in the spinal cord. Specifically, Kv3.1b (Deuchars et al., 2001; Brooke et al., 2002), Kv3.3 (Brooke et al., 2006), and Kv3.4 subunits (Brooke et al., 2004) have been identified in rodent spinal cord, although not always in association with circuits involved with sensory processing. It is likely that Kv3 channels shape the firing properties of spinal cord neurons, including motoneurons.

In addition recent studies showed the Kv3.4 channels expressed in DRG nociceptors have a significant impact on glutamatergic synaptic transmission (Muqeem et al., 2018). animal model data suggest a down-regulation of Kv3.4 channel surface expression in DRG neurons following spinal cord injury associated with hypersensitivity to painful stimuli (Ritter et al., 2015; Zemel et al., 2017; Zemel et al., 2018). Similarly, it has been observed that there is a down-regulation of Kv3.4 expression in DRGs of rodents following spinal cord ligation (Chien et al., 2007). This latter study also showed that intrathecal administration to rats of an antisense oligonucleotide to supress the expression of Kv3.4 led to hypersensitivity to mechanical stimuli. It has been shown that Kv3.4 channel inactivation could be influenced by protein kinase C-dependent phosphorylation of the channels, and that this physiological mechanism might allow DRG neurons to alter their firing characteristics in response to painful stimuli (Ritter et al., 2012). These studies suggest a causal relationship between the emergence of mechanical allodynia and reduced Kv3.4 channel expression or function. No evaluation of Kv3.1, Kv3.2, or Kv3.3 expression in SC or DRG neurons was conducted in any of these studies, and expression of these two subtypes has not been explicitly demonstrated on DRG neurons (although as mentioned above, they are abundant within specific regions of the spinal cord). The in vivo studies reported above provide a rationale for modulation of Kv3.4 as a novel approach to the treatment of certain neuropathic pain states.

Patent applications WO2011/069951, WO2012/076877, WO2012/168710, WO2013/175215, WO2013/083994, WO2013/182850, WO2017/103604, WO2018/020263, WO2018/109484 and WO2020/079422 disclose compounds which are modulators of Kv3.1 and Kv3.2. Further, the utility of such compounds is demonstrated in animal models of seizure, hyperactivity, sleep disorders, psychosis, hearing disorders and bipolar disorders.

Patent application WO2013/182851 discloses modulation of Kv3.3 channels by certain compounds.

Patent application WO2013/175211 discloses that modulation of Kv3.1, Kv3.2 and/or Kv3.3 channels has been found to be beneficial in preventing or limiting the establishment of a permanent hearing loss resulting from acute noise exposure. The benefits of such prevention may be observed even after administration of the Kv3.1, Kv3.2 and/or Kv3.3 modulator has ceased.

Patent application WO2017/098254 discloses that modulation of Kv3.1, Kv3.2 and/or Kv3.3 channels has been found to be beneficial in the prophylaxis or treatment of pain, in particular neuropathic or inflammatory pain.

Patent applications WO2019/222816, WO2020/000065, WO2020/089262, WO2020/216919 and WO2020/216920 are said to describe compounds which activate Kv3 potassium channels.

Patent applications EP3901152 and WO2021214090, published after the priority date of the present application, are said to describe Kv3 enhancers for the treatment of cognitive disorders.

There remains a need for the identification of alternative modulators of Kv3.1, Kv3.2, Kv3.3 and/or or Kv3.4 channels, in particular modulators of Kv3.1 and/or Kv3.2. Such modulators may demonstrate high in vivo potency, channel selectivity, an improved safety profile, or desirable pharmacokinetic parameters, for example high brain availability and/or low clearance rate that reduces the dose required for therapeutic effect in vivo. Alternative modulators may provide a benefit through having distinct metabolites from known modulators. Compounds which have balanced Kv3.1, Kv3.2, Kv3.3 and/or Kv3.4 modulatory properties may be desirable e.g. compounds with modulate Kv3.1 and Kv3.2 to the same, or a similar extent. For certain therapeutic indications, there is also a need to identify compounds with a different modulatory effect on Kv3.1, Kv3.2, Kv3.3 and/or Kv3.4 channels, for example, compounds that alter the kinetics of channel gating or channel inactivation, and which may behave in vivo as negative modulators of the channels.

SUMMARY OF THE INVENTION

The present invention provides a compound of formula (I):

(I)

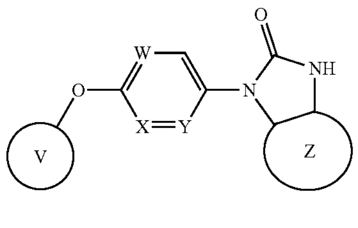

wherein:

V is group (Va), group (Vb) or group (Vc);

wherein group (Va) and group (Vb) are:

(Va)

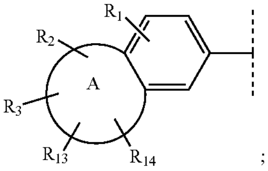

;

(Vb)

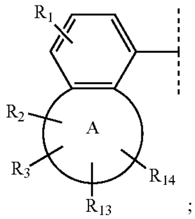

;

wherein:

$R_1$ is H, $C_{1-4}$alkyl, halo, halo$C_{1-4}$alkyl, CN, $C_{1-4}$alkoxy, or halo$C_{1-4}$alkoxy;

$R_2$ is H, $C_{1-4}$alkyl, $C_{3-5}$ spiro carbocyclyl, halo$C_{1-4}$alkyl or halo;

$R_3$ is H, $C_{1-4}$alkyl, halo$C_{1-4}$alkyl, halo; or $R_3$ is absent;

$R_{13}$ is H, $C_{1-4}$alkyl, halo$C_{1-4}$alkyl, halo; or $R_{13}$ is absent;

$R_{14}$ is H, $C_{1-4}$alkyl, halo$C_{1-4}$alkyl, halo; or $R_{14}$ is absent;

A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;

wherein $R_2$ and $R_3$ may be attached to the same or a different ring atom; $R_2$ may be attached to a fused ring atom; and wherein $R_{13}$ and $R_{14}$ may be attached to the same or a different ring atom;

wherein group (Vc) is:

(Vc)

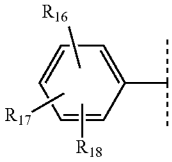

;

wherein:

$R_{16}$ is halo, $C_{1-4}$alkyl, $C_{1-4}$alkoxy, halo$C_{1-4}$alkyl, halo$C_{1-4}$ alkoxy or CN;

$R_{17}$ is H, halo, CN, $C_{1-4}$alkyl, $C_{1-4}$alkoxy or halo$C_{1-4}$ alkoxy;

$R_{13}$ is H, halo, CN, $C_{1-4}$alkyl or $C_{1-4}$alkoxy;

W is N or CH;

X is N or CH;

Y is N or CH;

wherein at least one of W, X and Y is CH, and when one of X and Y is N, the other is CH;

Z is a 5-membered heteroaryl comprising one or two nitrogen atoms, and wherein one of the nitrogen atoms and one of the carbon atoms may be independently optionally substituted by methyl; or Z is a 6-membered heteroaryl comprising one or two nitrogen atoms, wherein one of the carbon atoms may be optionally substituted by methyl; and provided that Z is not

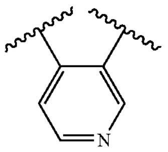 [SMILES: *c1ccncc1*]

wherein one of the carbon atoms may be optionally substituted by methyl;

or a salt and/or solvate and/or derivative thereof.

A compound of formula (I) may be provided in the form of a pharmaceutically acceptable salt and/or solvate and/or derivative thereof, such as a salt and/or solvate thereof, in particular a salt thereof. A compound of formula (I) may be provided in the form of a pharmaceutically acceptable salt and/or solvate thereof. In one embodiment of the invention a compound of formula (I) is provided in the form of a pharmaceutically acceptable salt.

The compounds of formula (I) may be used as medicaments, in particular for use in the prophylaxis or treatment of hearing disorders, including hearing loss and tinnitus, as well as schizophrenia, substance abuse disorders, pain or Fragile X syndrome.

Further, there is provided a method for the prophylaxis or treatment of hearing disorders, including hearing loss and tinnitus, as well as schizophrenia, substance abuse disorders, pain or Fragile X syndrome in a subject, the method comprising administering a compound of formula (I).

Compounds of formula (I) may be used in the manufacture of a medicament for the prophylaxis or treatment of hearing disorders, including hearing loss and tinnitus, as well as schizophrenia, substance abuse disorders, pain or Fragile X syndrome.

The compounds of formula (I) may be used as medicaments in the prophylaxis or treatment of epilepsy, in particular progressive myoclonic epilepsy, including PME associated with mutations in the KCNC1 gene.

Further, there is provided a method for the prophylaxis or treatment of epilepsy, in particular progressive myoclonic epilepsy, including PME associated with mutations in the KCNC1 gene in a subject, the method comprising administering a compound of formula (I).

Compounds of formula (I) may be used in the manufacture of a medicament for the prophylaxis or treatment of epilepsy, in particular progressive myoclonic epilepsy, including PME associated with mutations in the KCNC1 gene.

Also provided are pharmaceutical compositions containing a compound of formula (I) and a pharmaceutically acceptable carrier or excipient.

Also provided are processes for preparing compounds of formula (I) and novel intermediates of use in the preparation of compounds of formula (I).

Additionally provided are prodrug derivatives of the compounds of formula (I).

DETAILED DESCRIPTION OF THE INVENTION

In one embodiment, the invention provides a compound of formula (I):

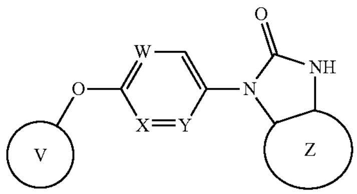

, wherein:

V is group (Va), group (Vb) or group (Vc);

wherein group (Va) and group (Vb) are:

(Va)

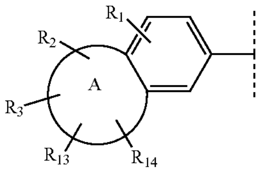

;

(Vb)

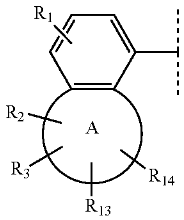

;

wherein:

$R_1$ is H, $C_{1-4}$alkyl, halo, halo$C_{1-4}$alkyl, CN, $C_{1-4}$alkoxy, or halo$C_{1-4}$alkoxy;

$R_2$ is H, $C_{1-4}$alkyl, $C_{3-5}$ spiro carbocyclyl, halo$C_{1-4}$alkyl or halo;

$R_3$ is H, $C_{1-4}$alkyl, halo$C_{1-4}$alkyl, halo; or $R_3$ is absent;

$R_{13}$ is H, $C_{1-4}$alkyl, halo$C_{1-4}$alkyl, halo; or $R_{13}$ is absent;

$R_{14}$ is H, $C_{1-4}$alkyl, halo$C_{1-4}$alkyl, halo; or $R_{14}$ is absent;

A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;

wherein $R_2$ and $R_3$ may be attached to the same or a different ring atom; $R_2$ may be attached to a fused ring atom; and wherein $R_{13}$ and $R_{14}$ may be attached to the same or a different ring atom;

wherein group (Vc) is:

(Vc)

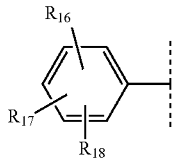

;

wherein:

$R_{16}$ is halo, $C_{1-4}$alkyl, $C_{1-4}$alkoxy, halo$C_{1-4}$alkyl, halo$C_{1-4}$ alkoxy or CN;

$R_{17}$ is H, halo, CN, $C_{1-4}$alkyl, $C_{1-4}$alkoxy or halo$C_{1-4}$ alkoxy;

$R_{13}$ is H, halo, CN, $C_{1-4}$alkyl or $C_{1-4}$alkoxy;

W is N or CH;

X is N or CH;

Y is N or CH;

wherein at least one of W, X and Y is CH, and when one of X and Y is N, the other is CH;

Z is a 5-membered heteroaryl comprising one or two nitrogen atoms, and wherein one of the nitrogen atoms and one of the carbon atoms may be independently optionally substituted by methyl; or Z is a 6-membered heteroaryl comprising one or two nitrogen atoms, wherein one of the carbon atoms may be optionally substituted by methyl; and provided that Z is not

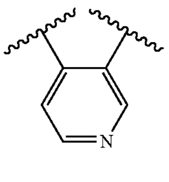 [SMILES: *c1ccncc1*]

wherein one of the carbon atoms may be optionally substituted by methyl.

The invention further provides a salt of a compound of formula (I). The invention further provides a pharmaceutically acceptable salt of a compound of formula (I). The invention further provides a solvate of a compound of formula (I). The invention further provides a pharmaceutically acceptable solvate of a compound of formula (I). The invention further provides a pharmaceutically acceptable salt and/or solvate of a compound of formula (I). The invention further provides a pharmaceutically acceptable salt and solvate of a compound of formula (I) (i.e. a pharmaceutically acceptable solvate of a pharmaceutically acceptable salt).

Embodiments set out below relating to relative stereochemistry and the nature of groups, including V, W, X, Y, Z, A, $R_1$, $R_2$, $R_3$, $R_{13}$, $R_{14}$, $R_{16}$, $R_{17}$, $R_{13}$ and Z are envisaged as being independently, fully combinable with one another where appropriate to the circumstances (i.e. where chemically sensible) to form further embodiments of the invention. Such embodiments apply equally to intermediates which may be of use in the synthesis of a compound of formula (I), such as compounds of formulae (II) and (Ill), (IV), (VI), (IX) and (X), e.g. compounds of formulae (II) and (III).

In one embodiment, V is group (Va). In a second embodiment, V is group (Vb). Groups (Va) and (Vb) both contain ring A and bear substituents $R_1$, $R_2$, $R_{13}$ and $R_{14}$.

In one embodiment, ring A is a 5 membered saturated heterocycle, with at least one O atom; which heterocycle is optionally fused with a cyclopropyl group, or a cyclobutyl group, or a cyclopentyl group to form a tricycle when considered together with the phenyl.

Ring A may be a 5 or 6 membered saturated or unsaturated heterocycle, with at least one O atom, suitably ring A may be a 5 membered saturated heterocycle, with at least one O atom.

In one embodiment, ring A contains one heteroatom which is oxygen. In one embodiment, ring A contains two heteroatoms, e.g. two oxygen atoms or one oxygen atom and one nitrogen atom. In one embodiment ring A is dihydrofuran, isoxazole, dihydropyran, 1,3-dioxolane, 1,3-oxazine or dihydropyran. Suitably, ring A is dihydrofuran or dihydropyran, in particular dihydrofuran.

In one embodiment, ring A is selected from the group consisting of:

1

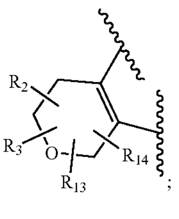

;

2

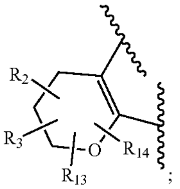

;

3

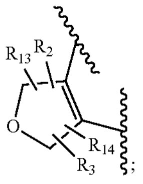

;

-continued
4
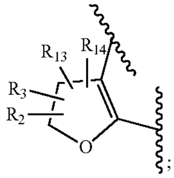;
5
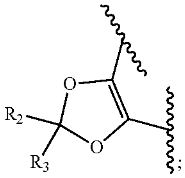;
6
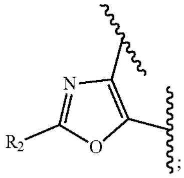;
7
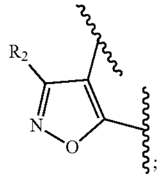;
8
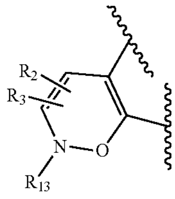;
9
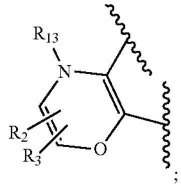;
10
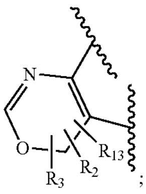; and
11
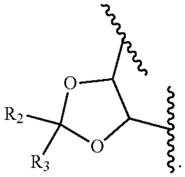.
wherein
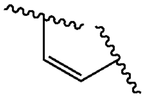
denotes a point at which ring A is fused to the phenyl ring.
In one embodiment, ring A is selected from the group consisting of:
1
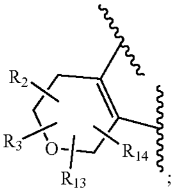;
2
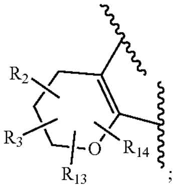;
3
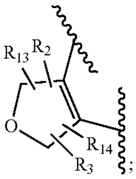;
4
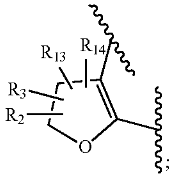;
5
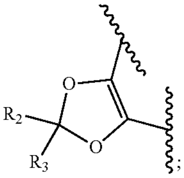;
6
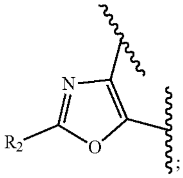;
7
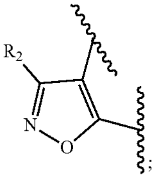;

-continued
8
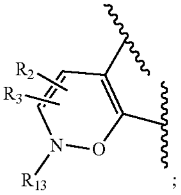
9
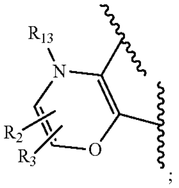
10
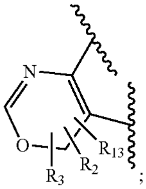
; and
11
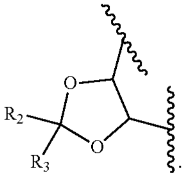
wherein
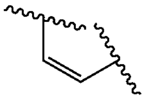 [SMILES: */C=C\*]
denotes a point at which ring A is fused to the phenyl ring.
In one embodiment, ring A is selected from the group consisting of:
1
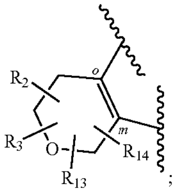
2
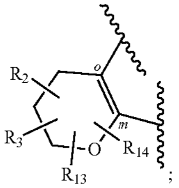
-continued
3
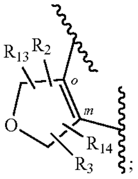
4
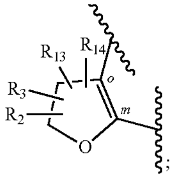
5
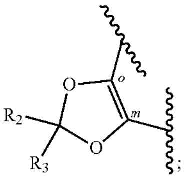
6
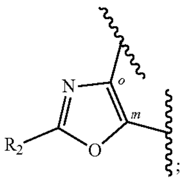
7
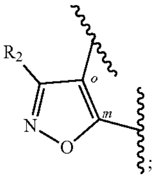
8
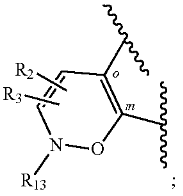
9
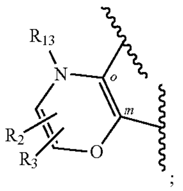
10
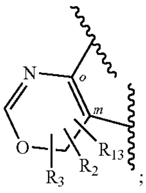
; and -continued

11

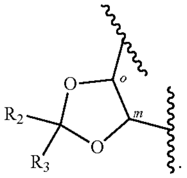

wherein

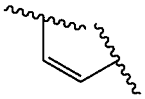 [SMILES: */C=C\*]

denotes a point at which ring A is fused to the phenyl ring, and "o" and "m" indicate the ortho- and meta-positions of the phenyl ring to which group A is fused.

In one embodiment, ring A is selected from the group consisting of:

1

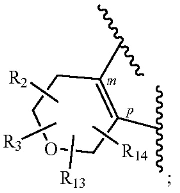

2

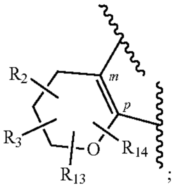

3

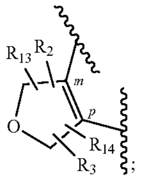

4

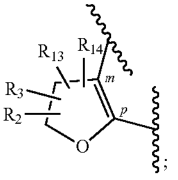

5

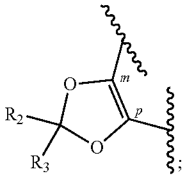

-continued

6

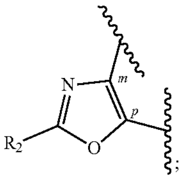

7

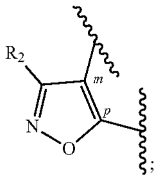

8

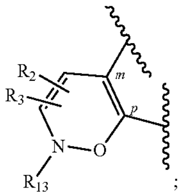

9

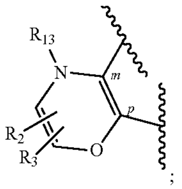

10

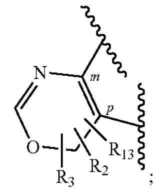

and

11

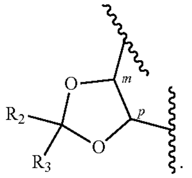

wherein

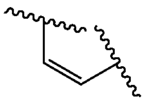

denotes a point at which ring A is fused to the phenyl ring, wherein "m" and "p" indicate the meta- and para-positions of the phenyl ring to which group A is fused.

Suitably, ring A is:
1
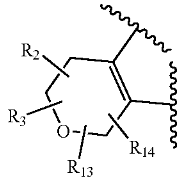
;
2
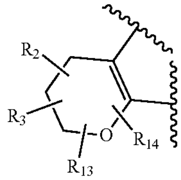
;
3
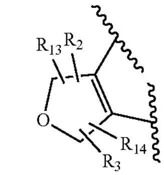
;
4
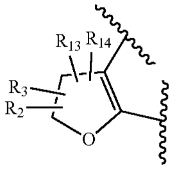
or
11
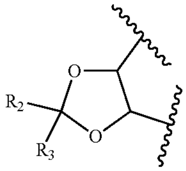
.
Suitably, ring A is:
1
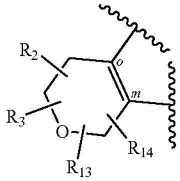
;
2
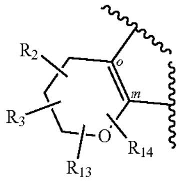
;
-continued
3
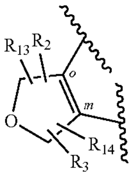
;
4
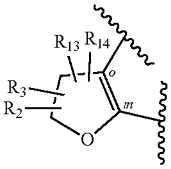
or
11
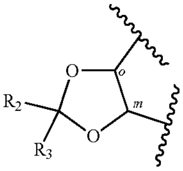
.
Suitably, ring A is:
1
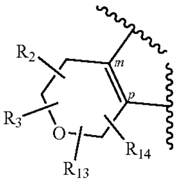
;
2
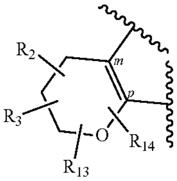
;
3
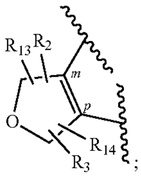
;
4
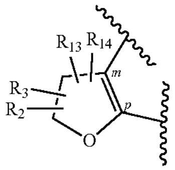
or
11
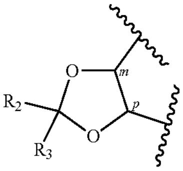
.

In particular, ring A is

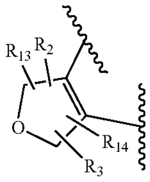

; or

3

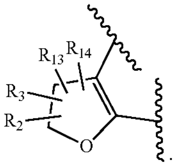

4

In particular, ring A is

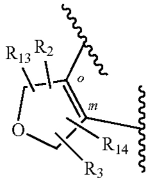

; or

3

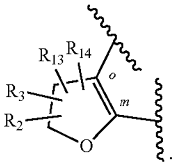

4

In particular, ring A is

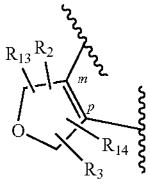

; or

3

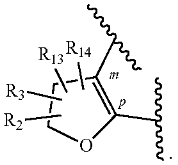

4

In one embodiment, when ring A is a 5 membered heterocycle containing one heteroatom which is oxygen, wherein suitably the oxygen atom is located at the phenolic position relative to the phenyl ring.

In one embodiment, $R_1$ is H, $C_{1-4}$alkyl, halo, halo$C_{1-4}$ alkyl or CN, in particular $C_{1-4}$alkyl such as methyl. In one embodiment, $R_1$ is H or methyl. In one embodiment, $R_1$ is H. In one embodiment, $R_1$ is methyl.

In one embodiment, when V is group (Vb), $R_1$ is at the para position and is H or methyl:

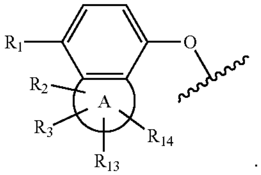

In one embodiment, when V is group (Vb), $R_1$ is in the meta position and is H or methyl:

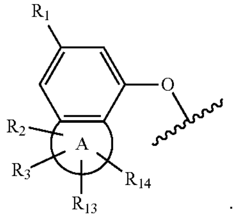

In one embodiment, when V is group (Vb), $R_1$ is in the ortho position and is H or methyl:

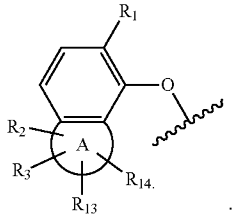

In one embodiment, $R_2$ is H, $C_{1-4}$alkyl, $C_{3-5}$spiro carbocyclyl or halo. In one embodiment, $R_2$ is $C_{1-4}$alkyl such as methyl or ethyl. In one embodiment $R_2$ is $C_{3-5}$spiro carbocyclyl such as $C_3$spiro carbocyclyl. In one embodiment, $R_2$ is methyl. In one embodiment, $R_2$ is halo e.g. fluoro.

In one embodiment $R_3$ is H, $C_{1-4}$alkyl, halo$C_{1-4}$alkyl or halo. In one embodiment, $R_3$ is $C_{1-4}$alkyl such as methyl. In one embodiment, $R_3$ is methyl. In another embodiment $R_3$ is halo e.g. fluoro. In another embodiment $R_3$ is absent.

In one embodiment, $R_2$ and $R_3$ are located on the same ring A atom.

In one embodiment, $R_{13}$ is H or is absent. Suitably, $R_{13}$ is absent.

In one embodiment, $R_{14}$ is H or is absent. Suitably, $R_{14}$ is absent.

V may be selected from the group consisting of:

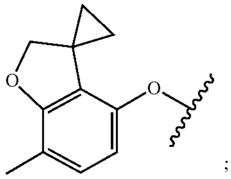 [SMILES: *Oc1ccc(C)c2c1C1(CC1)CO2]

;

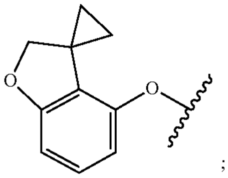

;

-continued

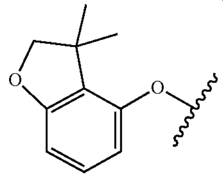
; and
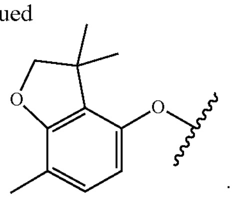
.

In one embodiment, V is

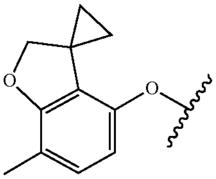
.

In one embodiment, V is

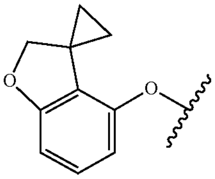
.

In one embodiment, V is

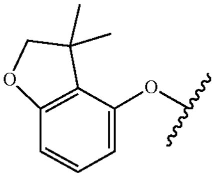
.

In one embodiment, V is

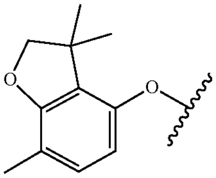
.

Group (Vc) bears substituents $R_{16}$, $R_{17}$ and $R_{18}$.

In one embodiment, $R_{16}$ is not in the para-position. In one embodiment, one of $R_{17}$ and $R_{13}$ is not H. In one embodiment, $R_{16}$ is in the meta-position. In one embodiment, $R_{17}$ is at the para position.

In one embodiment, $R_{16}$ is $C_{1-4}$alkyl, $C_{1-4}$alkoxy, halo$C_{1-4}$ alkyl, halo$C_{1-4}$alkoxy or CN. In one embodiment, $R_{16}$ is $C_{1-4}$alkyl, $C_{1-4}$alkoxy, halo$C_{1-4}$alkyl or halo$C_{1-4}$alkoxy. In one embodiment, $R_{16}$ is $C_{1-4}$alkyl, $C_{1-4}$alkoxy or halo$C_{1-4}$ alkoxy. In one embodiment, $R_{16}$ is halo, $C_{1-4}$alkyl or $C_{1-4}$alkoxy.

In one embodiment, $R_{16}$ is methyl, ethyl, propyl, butyl, cyclopropyl, chloro, fluoro, methoxy, ethoxy, propoxy, trifluoromethyl, trifluoromethoxy or CN. In one embodiment, $R_{16}$ is trifluoromethoxy or methoxy. In one embodiment, $R_{16}$ is trifluoromethoxy. In one embodiment, $R_{16}$ is methoxy.

In one embodiment, $R_{17}$ is H, halo, CN, $C_{1-4}$alkyl or $C_{1-4}$alkoxy. In one embodiment, $R_{17}$ is H, CN, $C_{1-4}$alkyl, $C_{1-4}$alkoxy or halo$C_{1-4}$alkoxy. In one embodiment, $R_{17}$ is $C_{1-4}$alkyl or $C_{1-4}$alkoxy. In one embodiment, $R_{17}$ is H, CN or $C_{1-4}$alkyl. In one embodiment, $R_{17}$ is H, CN or methyl. In one embodiment, $R_{17}$ is methyl, ethyl, propyl, butyl, cyclopropyl, chloro, fluoro, methoxy, ethoxy, propoxy, trifluoromethoxy or CN. In one embodiment, $R_{17}$ is H. In one embodiment, $R_{17}$ is methyl or CN. In one embodiment, $R_{17}$ is methyl. In one embodiment, $R_{17}$ is CN.

In one embodiment, $R_{13}$ is H.

In one embodiment, $R_{17}$ and $R_{13}$ are H. In one embodiment, $R_{16}$ is suitably at the ortho- or meta-position. In this embodiment, when $R_{16}$ is at the ortho position, it is suitably $C_{1-4}$ alkyl, for example methyl, ethyl, n-propyl, isopropyl, cyclopropyl, n-butyl or tert-butyl. In one embodiment, when $R_{16}$ is at the meta position, it is suitably $C_{1-4}$alkyl for example methyl, ethyl, isopropyl or cyclopropyl; $C_{1-4}$alkoxy for example methoxy or ethoxy; or halo$C_{1-4}$alkoxy for example trifluoromethoxy. In one embodiment, $R_{16}$ is trifluoromethoxy at the meta position, and $R_{17}$ and $R_{13}$ are H. In one embodiment, $R_{16}$ is methoxy at the meta position, and $R_{17}$ and $R_{13}$ are H.

In one embodiment, $R_{13}$ is H and $R_{17}$ is not H. In one embodiment one of $R_{16}$ or $R_{17}$ is at the ortho position. In this embodiment, the substituent at the ortho position is suitably $C_{1-4}$ alkyl, for example methyl, ethyl, n-propyl, isopropyl, cyclopropyl, n-butyl or tert-butyl. In another embodiment, one of $R_{16}$ and $R_{17}$ is at the ortho-position, and the other is at the meta-position. In this embodiment, the substituent at the ortho position is suitably $C_{1-4}$ alkyl, for example methyl, ethyl, n-propyl, isopropyl, cyclopropyl, n-butyl or tert-butyl and the substituent at the meta position is suitably $C_{1-4}$alkyl for example methyl, ethyl, isopropyl or cyclopropyl; $C_{1-4}$alkoxy for example methoxy or ethoxy; or halo$C_{1-4}$ alkoxy for example trifluoromethoxy. In one embodiment, one of $R_{16}$ and $R_{17}$ is at the ortho-position, and the other is at the para-position. In one embodiment, one of $R_{16}$ and $R_{17}$ is at position 1-, and the other is at position 4-. In this embodiment, the substituent in the para position is suitably CN, fluoro or methyl. In one embodiment, both of $R_{16}$ and $R_{17}$ are at the ortho-positions. In this embodiment, the substituents at the ortho position are suitably the same, and are suitably $C_{1-4}$ alkyl, for example methyl, ethyl, n-propyl, isopropyl, cyclopropyl, n-butyl or tert-butyl. In one embodiment $R_{16}$ is at the meta-position and $R_{17}$ is at the para-position. Within such an embodiment $R_{16}$ is suitably halo$C_{1-4}$ alkyl, for example trifluoromethoxy, and $R_{17}$ is CN or $C_{1-4}$alkyl, for example, CN, methyl, ethyl, n-propyl, isopropyl, cyclopropyl, n-butyl or tert-butyl, and in particular $R_{17}$ is CN or methyl. In one embodiment, $R_{16}$ is trifluoromethoxy at the meta-position and $R_{17}$ is CN at the para-position. In one embodiment $R_{16}$ is trifluoromethoxy at the meta-position and $R_{17}$ is methyl at the para-position.

References to substituent position numbering and nomenclature are made in respect of the position of the phenyl ring to the oxygen moiety, for example:

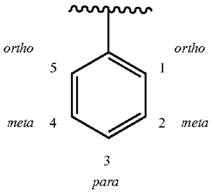 [SMILES: *c1ccccc1]

V may be selected from the group consisting of:

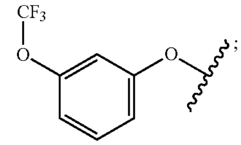;
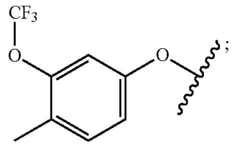;
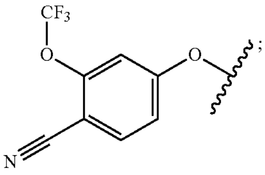; and
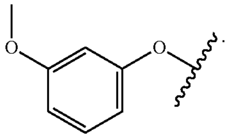.

In one embodiment, V is:

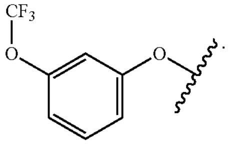 [SMILES: *Oc1cccc(OC(F)(F)F)c1].

In one embodiment, V is:

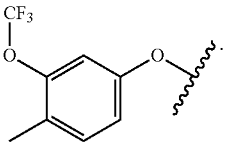 [SMILES: *Oc1ccc(C)c(OC(F)(F)F)c1].

In one embodiment, V is:

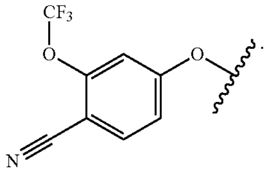 [SMILES: *Oc1ccc(C#N)c(OC(F)(F)F)c1].

In one embodiment, V is

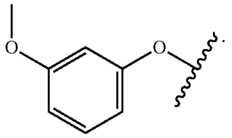 [SMILES: *Oc1cccc(OC)c1].

In one embodiment, W is N. In one embodiment, W is CH.

In one embodiment, X is N. In one embodiment, X is CH.

In one embodiment, Y is N. In one embodiment, Y is CH.

In one embodiment, W is N, and X and Y are CH. In one embodiment, W is N, X is N and Y is CH. In one embodiment, W is N, X is CH and Y is N. In one embodiment, W and X are CH, and Y is N.

In one embodiment, group Z is (Za):

(Za)

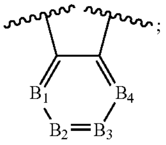;

wherein:

$B_1$, $B_2$, $B_3$ and $B_4$ are each independently selected from N, CH and C(Me);

wherein one or two of $B_1$, $B_2$, $B_3$ and $B_4$ are N, and only one of $B_1$, $B_2$, $B_3$ and $B_4$ may be C(Me);

and wherein when $B_1$, $B_2$ and $B_4$ are CH or C(Me), $B_3$ is not N.

Within such embodiments,

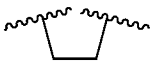

denotes the positions to which Z is fused to the cyclic urea, therefore

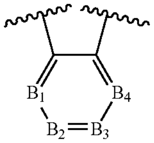

is equivalent to

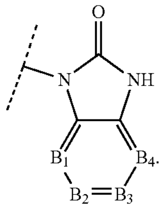.

In one embodiment, $B_1$ is N. In one embodiment, $B_1$ is CH.

In one embodiment, $B_2$ is N. In one embodiment, $B_2$ is CH or C(Me). In one embodiment, $B_2$ is CH. In one embodiment, $B_2$ is C(Me).

In one embodiment, $B_3$ is CH or N. In one embodiment, $B_3$ is N. In one embodiment, $B_3$ is CH. In one embodiment, $B_3$ is C(Me).

In one embodiment, $B_4$ is N. In one embodiment, $B_4$ is CH. In one embodiment, $B_4$ is C(Me).

In one embodiment, $B_1$ is N and $B_2$ is C(Me). In one embodiment, $B_1$ is N and $B_3$ is C(Me). In one embodiment, $B_1$ is N and $B_4$ is C(Me). In one embodiment, $B_1$ is N and $B_2$ is N. In one embodiment, $B_1$ is N and $B_3$ is N. In one embodiment, $B_1$ is N and $B_4$ is N. In one embodiment, $B_1$ and $B_3$ are N and $B_2$ is CH. In one embodiment, $B_1$ and $B_3$ are N and $B_2$ is C(Me). In one embodiment, $B_1$ is N, $B_2$ is C(Me), $B_3$ is N and $B_4$ is CH. In one embodiment, $B_1$ is N and $B_2$, $B_3$ and $B_4$ are each independently CH.

In one embodiment, (Za) is selected from the group consisting of:

Za1

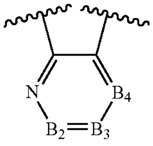

;

Za2

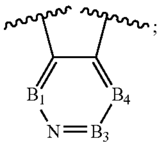

; and

Za3

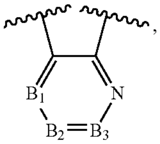

,

In one embodiment, (Za) is selected from the group consisting of:

Za4

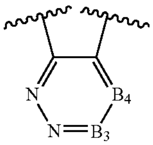

;

Za5

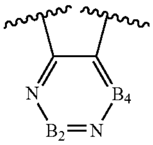

;

Za6

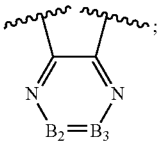

; and

Za7

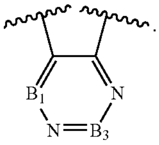

.

In one embodiment, (Za) is selected from the group consisting of:

Za8

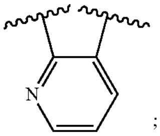

;

Za9

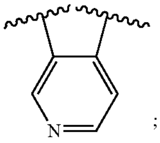

;

Za10

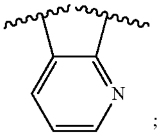

;

Za11

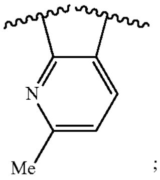

;

Za12

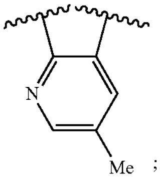

;

Za13

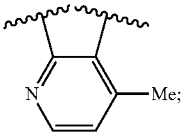

;

Za9-a

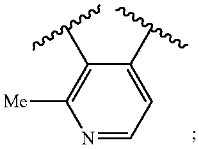

;

Za9-b

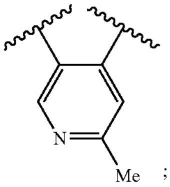

;

Za9-c

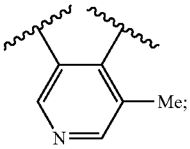

;

-continued
Za18
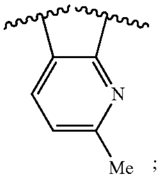
;
Za19
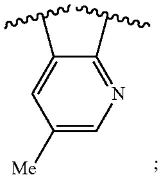
; and
Za20
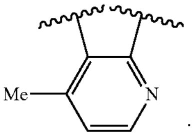
.
In one embodiment, (Za) is selected from the group consisting of:
Za14
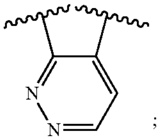
;
Za14-a
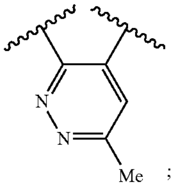
;
Za14-b
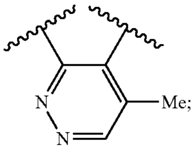
Za15
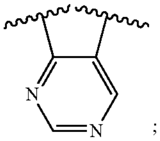
;
Za16
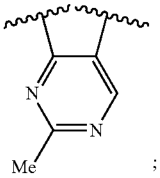
;
-continued
Za16-a
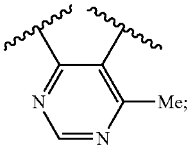
Za17
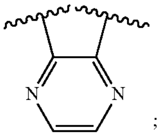
;
Za17-a
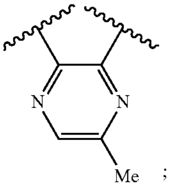
;
Za17-b
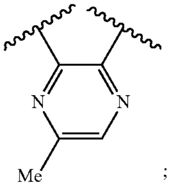
;
Za21
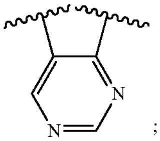
;
Za22
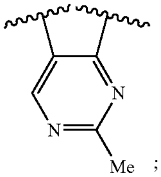
; and
Za22-a
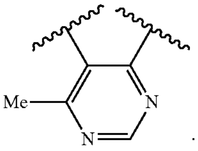
.
In one embodiment, (Za) is selected from the group consisting of:
Za8
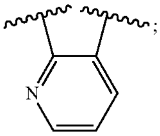
;

-continued

Za9

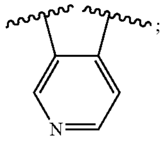

Za10

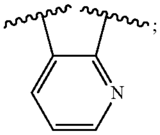

Za11

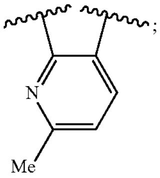

Za12

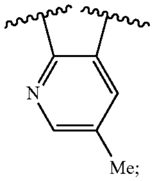

; and

Za13

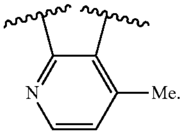

In one embodiment, (Za) is selected from the group consisting of:

Za15

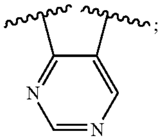

; and

Za16

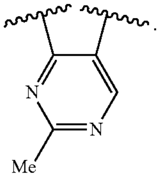

In one embodiment, (Za) is selected from the group consisting of:

Za8

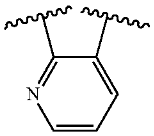

and

-continued

Za16

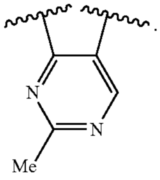

In one embodiment, (Za) is:

Za8

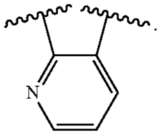

In one embodiment, (Za) is:

Za16

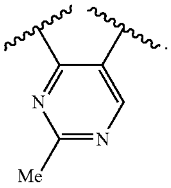

In one embodiment, group Z is group (Zb):

(Zb)

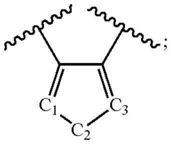

wherein:

$C_1$ and $C_3$ are each independently selected from CH, C(Me) and N; and $C_2$ is NH or N(Me); and wherein when one of $C_1$ and $C_3$ is N, the other is CH or C(Me).

In one embodiment, $C_1$ is CH. In one embodiment, $C_1$ is C(Me). In one embodiment, $C_1$ is N.

In one embodiment, $C_2$ is NH. In one embodiment, $C_2$ is N(Me).

In one embodiment, $C_3$ is CH. In one embodiment, $C_3$ is C(Me). In one embodiment, $C_3$ is N.

Within such embodiments,

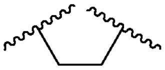

denotes the positions to which Z is fused to the cyclic urea, therefore
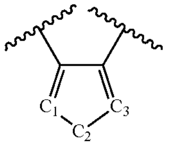
is equivalent to
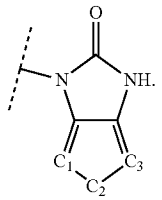
In one embodiment, (Zb) is selected from the group consisting of:
Zb1
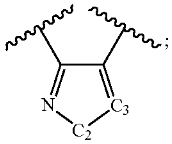;
Zb2
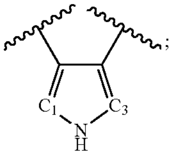;
Zb3
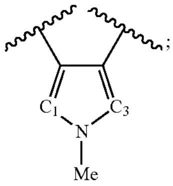; and
Zb4
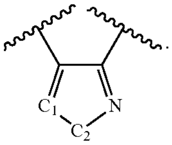.
In one embodiment, (Zb) is selected from the group consisting of:
Zb13
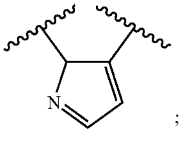;
-continued
Zb14
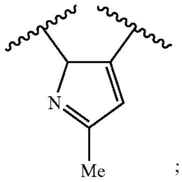;
Zb15
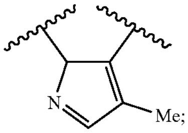;
Zb16
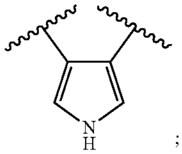;
Zb17
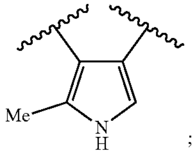;
Zb18
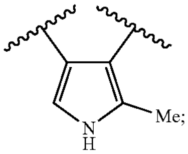;
Zb19
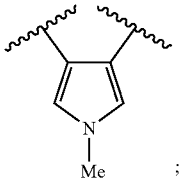;
Zb20
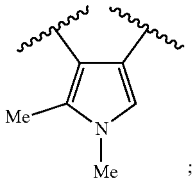;
Zb21
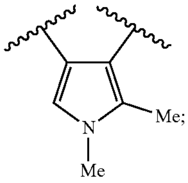;
Zb22
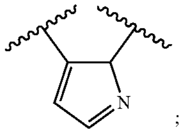;

-continued
Zb23
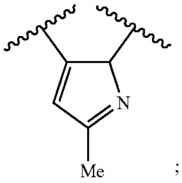
; and
Zb24
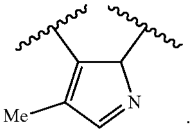
.
In one embodiment, (Zb) is selected from the group consisting of:
Zb5
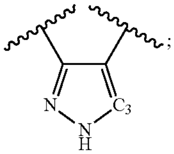
Zb6
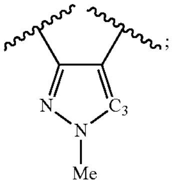
Zb7
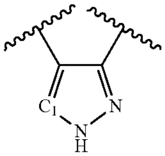
and
Zb8
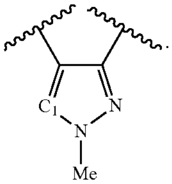
In one embodiment, (Zb) is selected from the group consisting of:
Zb5
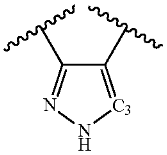
and
-continued
Zb6
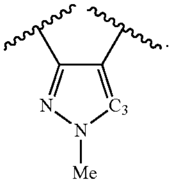
In one embodiment, (Zb) is selected from the group consisting of:
Zb9
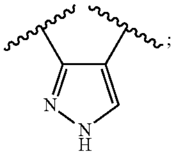
Zb10
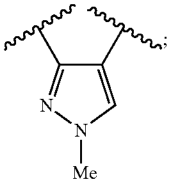
Zb11
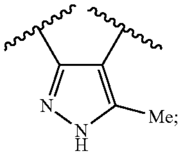
and
Zb12
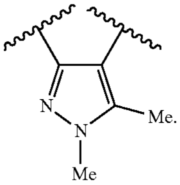
In one embodiment, (Zb) is selected from the group consisting of:
Zb9
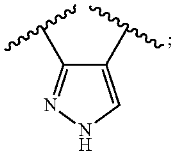
and
Zb10
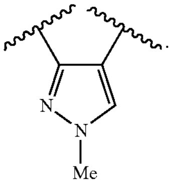

In one embodiment, (Zb) is:

Zb9

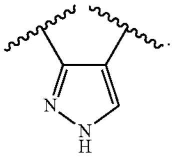

In one embodiment, (Zb) is:

Zb10

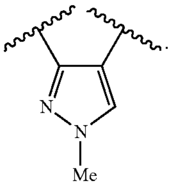

In one embodiment, Z is group (Zc):

Zc

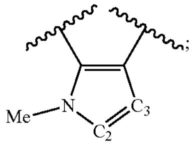

wherein:

$C_2$ is N, CH or C(Me) and $C_3$ is CH or C(Me); wherein when one of $C_2$ or $C_3$ is C(Me), the other is CH. In one embodiment $C_2$ is N. In a second embodiment $C_2$ is CH or C(Me).

Within such embodiments,

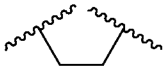 [SMILES: *CC*]

denotes the positions to which Z is fused to the cyclic urea, therefore

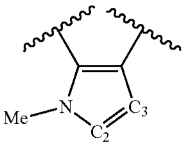

is equivalent to

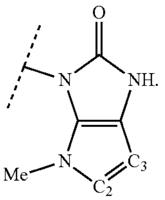

In one embodiment, (Zc) is selected from the group consisting of:

Zc1

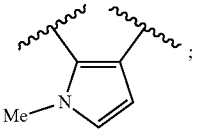

Zc2

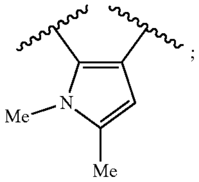

and

Zc3

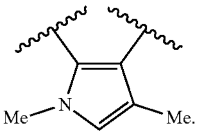

In one embodiment, Z is group (Zd):

Zd

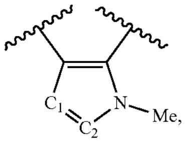

wherein:

$C_1$ is CH or C(Me) and $C_2$ is N, CH or C(Me); wherein when one of $C_1$ or $C_2$ is C(Me), the other is CH. In one embodiment $C_2$ is N. In a second embodiment $C_2$ is CH or C(Me).

Within such embodiments,

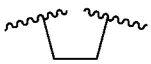

denotes the positions to which Z is fused to the cyclic urea, wherein

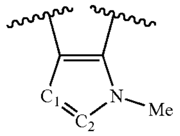

is equivalent to

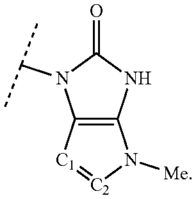

In one embodiment, (Zd) is selected from the group consisting of:

Zd1

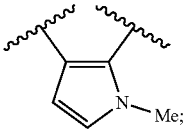

Zd2

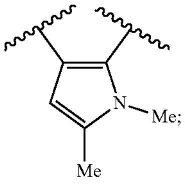

and

Zd3

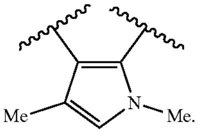

In one embodiment, Z is selected from the group consisting of (Ze-a), (Ze-b) and (Ze-c):

Ze-a

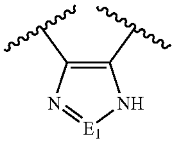

,

Ze-b

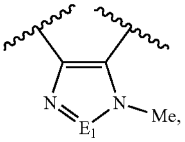

-continued

Ze-c

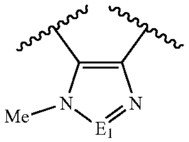

;

wherein:

$E_1$ is CH or C(Me).

Within such embodiments,

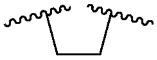 [SMILES: *CC*]

denotes the positions to which Z is fused to the cyclic urea, therefore

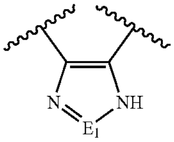

,

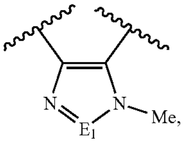

and

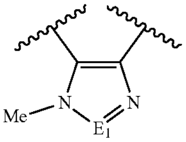

;

are identical to

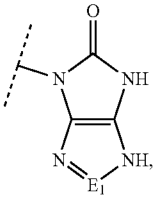

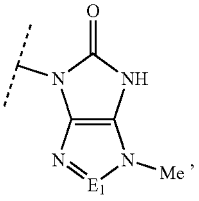

and

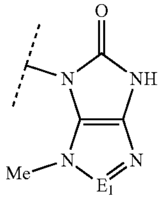

respectively.

In one embodiment, Z is group (Ze-a).

In one embodiment, (Ze-a) is selected from the group consisting of:

Ze-a1

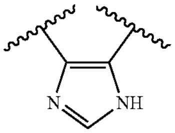

; and

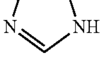

-continued

Ze-a2

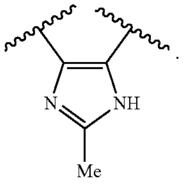

In one embodiment, Z is group (Ze-b).

In one embodiment, (Ze-b) is selected from the group consisting of:

Ze-b1

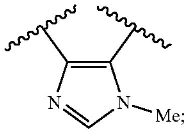

and

Ze-b2

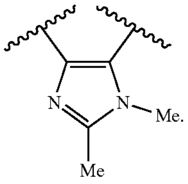

In one embodiment, Z is group (Ze-c).

In one embodiment, (Ze-c) is selected from the group consisting of:

Ze-c1

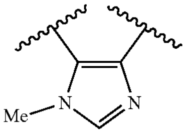

; and

Ze-c2

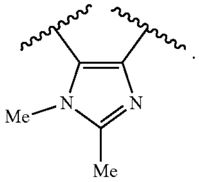

In one embodiment, there is provided a compound of formula (I) which is selected from the group consisting of:

3-[6-(7-methylspiro[2H-benzofuran-3,1'-cyclopropane]-4-yl)oxy-3-pyridyl]-1H-imidazo[4,5-b]pyridin-2-one;
7-methyl-3-[6-(7-methylspiro[2H-benzofuran-3,1'-cyclopropane]-4-yl)oxy-3-pyridyl]-1H-imidazo[4,5-b]pyridin-2-one;
3-(6-spiro[2H-benzofuran-3,1'-cyclopropane]-4-yloxy-3-pyridyl)-1H-imidazo[4,5-b]pyridin-2-one;
3-[6-[4-methyl-3-(trifluoromethoxy)phenoxy]-3-pyridyl]-1H-imidazo[4,5-b]pyridin-2-one;
7-methyl-3-(6-spiro[2H-benzofuran-3,1'-cyclopropane]-4-yloxy-3-pyridyl)-1H-imidazo[4,5-b]pyridin-2-one;
3-(5-spiro[2H-benzofuran-3,1'-cyclopropane]-4-yloxy-2-pyridyl)-1H-imidazo[4,5-b]pyridin-2-one;
3-[6-[3-(trifluoromethoxy)phenoxy]-3-pyridyl]-1H-imidazo[4,5-b]pyridin-2-one;
3-(5-spiro[2H-benzofuran-3,1'-cyclopropane]-4-yloxy-pyrazin-2-yl)-1H-imidazo[4,5-b]pyridin-2-one;
3-[5-[(3,3-dimethyl-2H-benzofuran-4-yl)oxy]pyrazin-2-yl]-1H-imidazo[4,5-b]pyridin-2-one;
3-[5-[3-(trifluoromethoxy)phenoxy]pyrazin-2-yl]-1H-imidazo[4,5-b]pyridin-2-one;
3-[5-(7-methylspiro[2H-benzofuran-3,1'-cyclopropane]-4-yl)oxypyrazin-2-yl]-1H-imidazo[4,5-b]pyridin-2-one;
3-[6-[(3,3-dimethyl-2H-benzofuran-4-yl)oxy]-3-pyridyl]-1H-imidazo[4,5-b]pyridin-2-one;
3-(2-{2H-spiro[1-benzofuran-3,1'-cyclopropane]oxy}pyrimidin-5-yl)-1H,2H,3H-imidazo[4,5-b]pyridin-2-one;
4-[[5-(2-oxo-1H-imidazo[4,5-b]pyridin-3-yl)-2-pyridyl]oxy]-2-(trifluoromethoxy)benzonitrile;
7-methyl-3-(2-spiro[2H-benzofuran-3,1'-cyclopropane]-4-yloxypyrimidin-5-yl)-1H-imidazo[4,5-b]pyridin-2-one;
3-[2-(3-methoxyphenoxy)pyrimidin-5-yl]-1H-imidazo[4,5-b]pyridin-2-one;
3-[2-[3-(trifluoromethoxy)phenoxy]pyrimidin-5-yl]-1H-imidazo[4,5-b]pyridin-2-one;
2-methyl-6-(6-spiro[2H-benzofuran-3,1'-cyclopropane]-4-yloxy-3-pyridyl)-4H-imidazo[4,5-c]pyrazol-5-one;
2-methyl-6-[6-(7-methylspiro[2Hbenzofuran-3,1'-cyclopropane]-4-yl)oxy-3-pyridyl]-4H-imidazo[4,5-c]pyrazol-5-one;
6-[6-[(3,3-dimethyl-2H-benzofuran-4-yl)oxy]-3-pyridyl]-2-methyl-4H-imidazo[4,5-c]pyrazol-5-one;
2-methyl-6-(5-spiro[2H-benzofuran-3,1'-cyclopropane]-4-yloxypyrazin-2-yl)-4H-imidazo[4,5-c]pyrazol-5-one;
2-methyl-6-(2-spiro[2H-benzofuran-3,1'-cyclopropane]-4-yloxypyrimidin-5-yl)-4H-imidazo[4,5-c]pyrazol-5-one;
3-[2-[(3,3-dimethyl-2H-benzofuran-4-yl)oxy]pyrimidin-5-yl]-1H-imidazo[4,5-c]pyridin-2-one;
2-methyl-9-[6-[3-(trifluoromethoxy) phenoxy]-3-pyridyl]-7H-purin-8-one;
2-methyl-9-[6-(7-methylspiro[2H-benzofuran-3,1'-cyclopropane]-4-yl)oxy-3-pyridyl]-7H-purin-8-one;
2-methyl-9-(6-spiro[2H-benzofuran-3,1'-cyclopropane]-4-yloxy-3-pyridyl)-7H-purin-8-one;
2-methyl-9-[6-[4-methyl-3-(trifluoromethoxy)phenoxy]-3-pyridyl]-7H-purin-8-one;
9-[6-(3-methoxyphenoxy)-3-pyridyl]-2-methyl-7H-purin-8-one;
9-[6-(7-methylspiro[2H-benzofuran-3,1'-cyclopropane]-4-yl)oxy-3-pyridyl]-7H-purin-8-one;
9-[6-[(3,3-dimethyl-2H-benzofuran-4-yl)oxy]-3-pyridyl]-2-methyl-7H-purin-8-one;
3-[2-(7-methylspiro[2H-benzofuran-3,1'-cyclopropane]-4-yl)oxypyrimidin-5-yl]-1H-imidazo[4,5-b]pyridine-2-one;
3-[2-[4-methyl-3-(trifluoromethoxy)phenoxy]pyrimidin-5-yl]-1H-imidazo[4,5-b]pyridin-2-one;
3-[2-[(3,3-dimethyl-2H-benzofuran-4-yl)oxy]pyrimidin-5-yl]-1H-imidazo[4,5-b]pyridin-2-one;
6-(6-spiro[2H-benzofuran-3,1'-cyclopropane]-4-yloxy-3-pyridyl)-2,4-dihydroimidazo[4,5-c]pyrazol-5-one;
3-[6-(7-methylspiro[2H-benzofuran-3,1'-cyclopropane]-4-yl)oxy-3-pyridyl]-1H-imidazo[4,5-c]pyridin-2-one;
1-(6-spiro[2H-benzofuran-3,1'-cyclopropane]-4-yloxy-3-pyridyl)-3H-imidazo[4,5-b]pyridin-2-one;
5-methyl-3-(5-spiro[2H-benzofuran-3,1'-cyclopropane]-4-yloxypyrazin-2-yl)-1H-imidazo[4,5-b]pyridin-2-one;
6-methyl-3-(5-spiro[2H-benzofuran-3,1'-cyclopropane]-4-yloxypyrazin-2-yl)-1H-imidazo[4,5-b]pyridin-2-one; and
3-[2-[(3,3,7-trimethyl-2H-benzofuran-4-yl)oxy]pyrimidin-5-yl]-1H-imidazo[4,5-b]pyridin-2-one.

In one embodiment, there is provided a compound of formula (I) which is 2-methyl-9-[6-[3-(trifluoromethoxy)phenoxy]-3-pyridyl]-7H-purin-8-one.

In one embodiment, there is provided a compound of formula (I) which is 3-[2-[3-(trifluoromethoxy)phenoxy]pyrimidin-5-yl]-1H-imidazo[4,5-b]pyridin-2-one.

In one embodiment, there is provided a compound of formula (I) which is 3-(2-{2H-spiro[1-benzofuran-3,1'-cyclopropane]oxy}pyrimidin-5-yl)-1H,2H,3H-imidazo[4,5-b]pyridin-2-one.

In one embodiment, there is provided a compound of formula (I) which is 3-[2-[(3,3-dimethyl-2H-benzofuran-4-yl)oxy]pyrimidin-5-yl]-1H-imidazo[4,5-b]pyridin-2-one.

Such compounds may be provided in the form of a salt and/or solvate thereof and/or derivative thereof, such as a salt and/or solvate thereof. Such compounds may also be provided in the form of a pharmaceutically acceptable salt and/or solvate thereof and/or derivative thereof, such as a pharmaceutically acceptable salt and/or solvate thereof, in particular a pharmaceutically acceptable salt. Suitably, such compounds are not provided in the form of a salt.

The term "5-membered heteroaryl" as used herein refers to a 5-membered aromatic ring including at least one heteroatom e.g. nitrogen. Examples of 5-membered heteroaryl include one nitrogen atom (pyrrole), two nitrogen atoms (imidazole or pyrazole) or three nitrogen atoms (triazole).

The term "6-membered heteroaryl" as used herein refers to a 6-membered aromatic ring including at least one heteroatom e.g. nitrogen. Examples of 6-membered heteroaryl include one nitrogen atom (pyridine) or two nitrogen atoms (pyridazine, pyrimidine or pyrazine).

The term 'halo' or 'halogen' as used herein, refers to a fluorine, chlorine, bromine or iodine atom. Particular examples of halo are fluorine and chlorine, especially fluorine.

When the compound contains a $C_{1-4}$alkyl group, whether alone or forming part of a larger group, e.g. $C_{1-4}$alkoxy, the alkyl group may be straight chain, branched, cyclic, or a combination thereof. Examples of $C_{1-4}$alkyl are methyl, ethyl, n-propyl, isopropyl, cyclopropyl, n-butyl, isobutyl, sec-butyl, tert-butyl, and cyclobutyl. Reference to "propyl" includes n-propyl, isopropyl and cyclopropyl, and reference to "butyl" includes n-butyl, isobutyl, sec-butyl, tert-butyl and cyclobutyl. A particular group of exemplary $C_{1-4}$alkyl groups are methyl, ethyl, n-propyl, isopropyl, cyclopropyl, n-butyl, isobutyl, sec-butyl and tert-butyl. Examples of $C_{1-4}$alkoxy include methoxy, ethoxy, propoxy (which includes n-propoxy, isopropoxy and cyclopropoxy) and butoxy.

The term "$C_{1-4}$alkoxy" also extends to embodiments in which the oxygen atom is located within the alkyl chain, for example —$CH_2CH_2OCH_3$ or —$CH_2OCH_3$. Thus, in one embodiment the alkoxy is linked through carbon to the remainder of the molecule. In one embodiment the alkoxy is linked through oxygen to the remainder of the molecule, for example —$OC_{1-4}$alkyl.

The term 'halo$C_{1-4}$alkyl' as used herein, includes straight chain, branched chain or cyclic alkyl groups containing 1 to 4 carbon atoms substituted by one or more halo atoms, for example fluoromethyl, difluoromethyl and trifluoromethyl. A particular group of exemplary halo$C_{1-4}$ alkyl include methyl and ethyl groups substituted with one to three halo atoms, in particular one to three fluoro atoms, such as trifluoromethyl or 2,2,2-trifluoroethyl.

The term 'halo$C_{1-4}$alkoxy' as used herein, includes straight chain, branched chain or cyclic alkoxy groups containing 1 to 4 carbon atoms substituted by one or more halo atoms, for example fluoromethoxy, difluoromethoxy and trifluoromethoxy. A particular group of exemplary halo$C_{1-4}$ alkyl include methoxy and ethoxy groups substituted with one to three halo atoms, in particular one to three fluoro atoms.

The term '$C_{3-5}$ spiro carbocyclyl' as used herein means a cyclic ring system containing 3 to 5 carbon atoms, for example, a cyclopropyl, cyclobutyl or cyclopentyl group, wherein the cyclic ring system is attached to a secondary carbon via a spirocentre such that the secondary carbon is one of the 3 to 5 carbon atoms in the cyclic ring as follows:

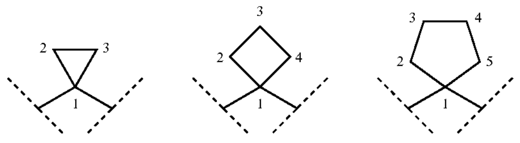

$C_3$ spiro carbocyclyl $C_4$ spiro carbocyclyl $C_5$ spiro carbocyclyl

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge et al. Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Non-pharmaceutically acceptable salts may be used, for example, in the isolation of compounds of formula (I) and are included within the scope of this invention. For example, in one embodiment, there is provided a compound of formula (I) or salt thereof.

Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water).

It will be understood that the invention includes pharmaceutically acceptable derivatives of compounds of formula (I) and that these are included within the scope of the invention.

As used herein "pharmaceutically acceptable derivative" includes any pharmaceutically acceptable ester or salt of such ester of a compound of formula (I) which, upon administration to the recipient is capable of providing (directly or indirectly) a compound of formula (I) or an active metabolite or residue thereof. Pharmaceutically acceptable derivatives include pharmaceutically acceptable prodrugs.

A pharmaceutically acceptable prodrug may be formed by functionalising the secondary nitrogen of the urea, for example with a group "L" as illustrated below (wherein $R_4$ and $R_5$ are as described above):

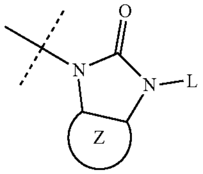

In one embodiment of the invention, a compound of formula (I) is functionalised via the secondary nitrogen of the urea with a group L, wherein L is selected from:

—$PO(OH)O^-·M^+$, wherein $M^+$ is a pharmaceutically acceptable monovalent counterion,

—$PO(O^-)_2.2M^+$,

—$PO(O^-)_2·D^{2+}$, wherein $D^{2+}$ is a pharmaceutically acceptable divalent counterion, —$CH(R^X)$—$PO(OH)O^-·M^+$, wherein $R^X$ is hydrogen or $C_{1-3}$ alkyl,

—$CH(R^X)$—$PO(O^-)_2.2M^+$,

—$CH(R^X)$—$PO(O^-)_2·D^{2+}$, and

—CO—$CH_2CH_2$—$CO_2·M^+$.

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The present disclosure includes all isotopic forms of the compounds of the invention provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exist as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^2H$ or D), carbon-11 ($^{11}C$), carbon-13 ($^{13}C$), carbon-14 ($^{14}C$), nitrogen-13 ($^{13}N$), nitrogen-15 ($^{15}N$), oxygen-15 ($^{15}O$), oxygen-17 ($^{17}O$), oxygen-18 (180), phosphorus-32 ($^{32}P$), sulphur-35 ($^{35}S$), chlorine-36 ($^{36}Cl$), chlorine-37 ($^{37}Cl$), fluorine-18 ($^{18}F$) iodine-123 ($^{123}I$), iodine-125 ($^{125}I$) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Unnatural variant isotopic forms which incorporate deuterium i.e. 2H or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}C$, $^{18}F$, $^{15}O$ and $^{13}N$, and would be useful in Positron Emission Topography (PET) studies for examining substrate receptor occupancy.

In one embodiment, the compounds of the invention are provided in a natural isotopic form.

In one embodiment, the compounds of the invention are provided in an unnatural variant isotopic form. In a specific embodiment, the unnatural variant isotopic form is a form in which deuterium (i.e. $^2H$ or D) is incorporated where hydrogen is specified in the chemical structure in one or more atoms of a compound of the invention. In one embodiment, the atoms of the compounds of the invention are in an isotopic form which is not radioactive. In one embodiment, one or more atoms of the compounds of the invention are in an isotopic form which is radioactive. Suitably radioactive isotopes are stable isotopes. Suitably the unnatural variant isotopic form is a pharmaceutically acceptable form.

In one embodiment, a compound of the invention is provided whereby a single atom of the compound exists in an unnatural variant isotopic form. In another embodiment, a compound of the invention is provided whereby two or more atoms exist in an unnatural variant isotopic form.

Unnatural isotopic variant forms can generally be prepared by conventional techniques known to those skilled in the art or by processes described herein e.g. processes analogous to those described in the accompanying Examples for preparing natural isotopic forms. Thus, unnatural isotopic variant forms could be prepared by using appropriate isotopically variant (or labelled) reagents in place of the normal reagents employed in the Examples. Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

In general, the compounds of formula (I) may be made according to the organic synthesis techniques known to those skilled in this field, as well as by the representative methods set forth below, those in the Examples and modifications thereof.

Patent applications WO2011/069951, WO2012/076877, WO2012/168710, WO2013/175215, WO2013/083994, WO2017/098254, WO2017/103604, WO2018/020263, WO2018/109484 and WO2020/079422 provide methods for the synthesis of intermediates which may be of use in the production of compounds of the present invention.

General Synthesis Schemes

The following schemes detail synthetic routes to compounds of the invention and intermediates in the synthesis of such compounds. In the following schemes reactive groups can be protected with protecting groups and deprotected according to established techniques well known to the skilled person.

Compounds may be prepared by the general methods outlined hereinafter. In the following description, the groups V, W, X, Y and Z have the meanings as previously defined for unless otherwise stated.

Scheme 1a

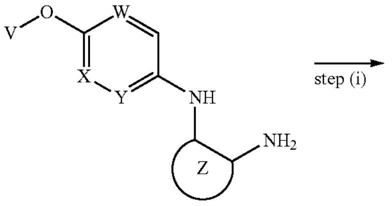

(II)

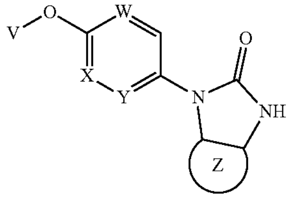

(I)

Compounds of formula (I) can be prepared by cyclization of compounds of formula (II) in a suitable solvent e.g. dichloromethane with a carbonylating agent e.g. triphosgene preferentially prediluted in the same solvent and added in a second time at 0° C. in presence of a suitable base e.g. triethylamine. Alternatively compounds of formula (I) can be prepared by cyclization of compounds of formula (II) using a carbonylating agent such as carbonyldiimidazole in a suitable solvent such as ethyl acetate in presence of a base such as triethylamine or DIPEA.

Scheme 1b

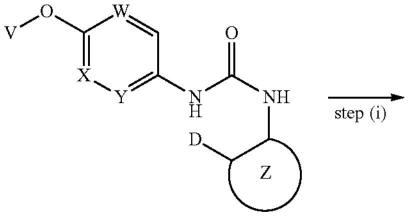

(III)

-continued

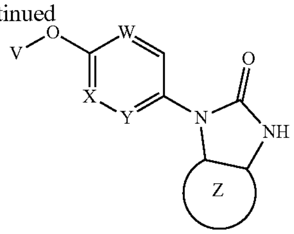

(I)

Compounds of formula (I) can be prepared by metal catalysed cross coupling reactions. In this reaction a aryl-halide derivative of formula (III) wherein typically D=Cl, Br or I is reacted in the presence of a metal catalyst such as diacetoxypalladium (palladium(II) acetate), a suitable ligand such as 5-diphenylphosphanyl-9,9-dimethyl-xanthen-4-yl)-diphenyl-phosphane (Xantphos) and a suitable base such as cesium carbonate in a suitable solvent e.g. in 1,4-dioxane, with conventional heating or microwave heating.

Scheme 1c

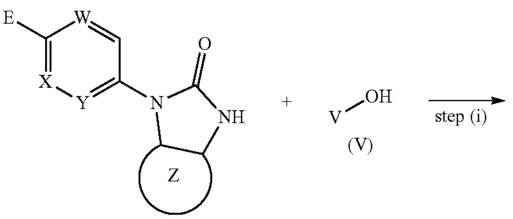

(IV)

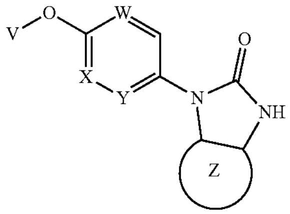

(I)

Compounds of formula (I) can be prepared by nucleophilic aromatic substitution. In this reaction an aryl-halide derivative of formula (IV) wherein typically E=F or Cl and a phenol of formula (V) are reacted in the presence of a suitable base such as potassium carbonate in a suitable solvent, e.g. in N,N-dimethylacetamide, in N,N-dimethylformamide or in dimethyl sulfoxide, with conventional heating or microwave heating.

Scheme 2

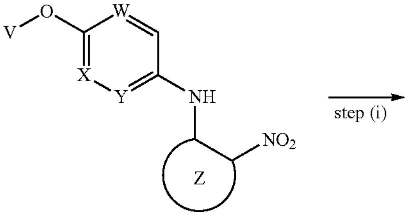

(VI)

-continued

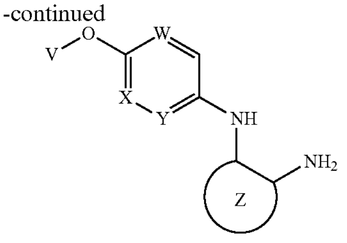

(II)

Anilines of formula (II) can be prepared by the reduction of nitro compounds of formula (VI). Suitable reactions conditions to transform (VI) into (II) are for example reduction in presence of Fe powder and ammonium chloride in a solvent such as a mixture ethanol/water for example at room temperature or with conventional heating.

Scheme 3

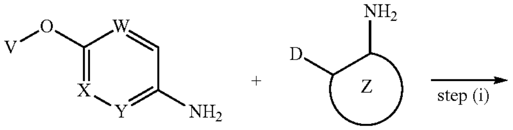

(VII) (VIII)

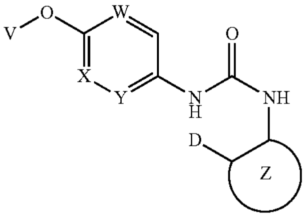

(III)

Ureas of formula (III) can be prepared by reaction of anilines of formula (VII) and anilines of formula (VIII) in a suitable solvent e.g. dichloromethane or ethyl acetate with a carbonylating agent e.g. triphosgene preferentially prediluted in the same solvent in presence of a suitable base e.g. triethylamine or diisopropylethylamine at temperature ranging from 0° C. to room temperature.

Scheme 4a

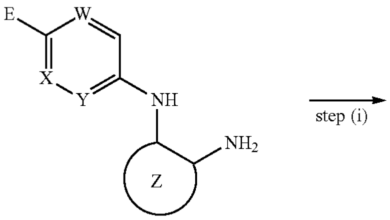

(IX)

-continued

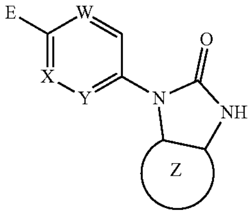

(IV)

Compounds of formula (IV) can be prepared by cyclization of compounds of formula (IX) in a suitable solvent e.g. dichloromethane with a carbonylating agent e.g. triphosgene preferentially prediluted in the same solvent and added in a second time at 0° C. in presence of a suitable base e.g. triethylamine. Alternatively compounds of formula (I) can be prepared by cyclization of compounds of formula (II) using a carbonylating agent such as carbonyldiimidazole in a suitable solvent such as ethyl acetate in presence of a base such as triethylamine or DIPEA.

Scheme 4b

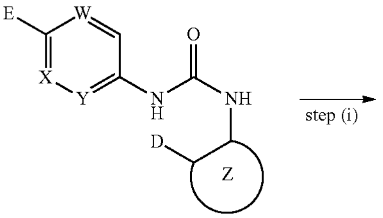

(X)

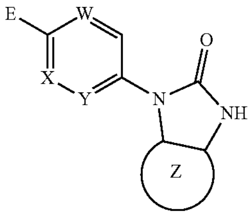

(IV)

Compounds of formula (IV) can be prepared by metal catalysed cross coupling reactions. In this reaction a arylhalide derivative of formula (X) wherein typically D=Cl, Br or I is reacted in the presence of a metal catalyst such as diacetoxypalladium (palladium(II) acetate), a suitable ligand such as 5-diphenylphosphanyl-9,9-dimethyl-xanthen-4-yl)-diphenyl-phosphane (Xantphos) and a suitable base such as cesium carbonate in a suitable solvent e.g. in 1,4-dioxane, with conventional heating or microwave heating.

Scheme 5

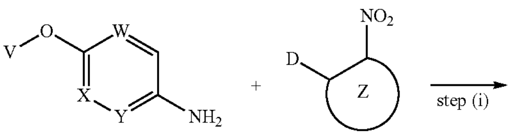

(VII) (XI)

-continued

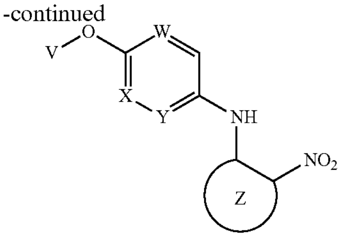

(VI)

Compounds of formula (VI) can be prepared by metal catalysed cross coupling reactions. In this reaction an aniline of formula (VII) and an aryl-halide derivative of formula (XI) wherein typically D=Cl, Br or I are reacted in the presence of a metal catalyst such as diacetoxypalladium (palladium(II) acetate), a suitable ligand such as 5-diphenylphosphanyl-9,9-dimethyl-xanthen-4-yl)-diphenyl-phosphane (Xantphos) and a suitable base such as cesium carbonate in a suitable solvent e.g. in 1,4-dioxane, with conventional heating or microwave heating.

Scheme 6

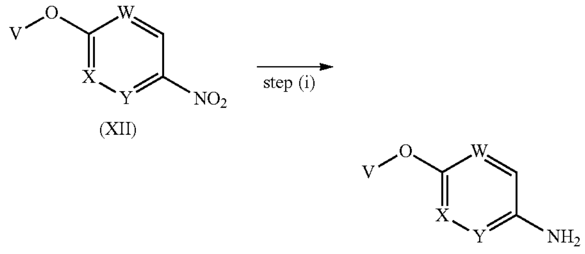

(XII)

(VII)

Anilines of formula (VII) can be prepared by the reduction of nitro compounds of formula (XII) Suitable reactions conditions to transform (XII) into (VII) are for example reduction in presence of Fe powder and ammonium chloride in a solvent such as a mixture ethanol/water for example at room temperature or with conventional heating.

Scheme 7

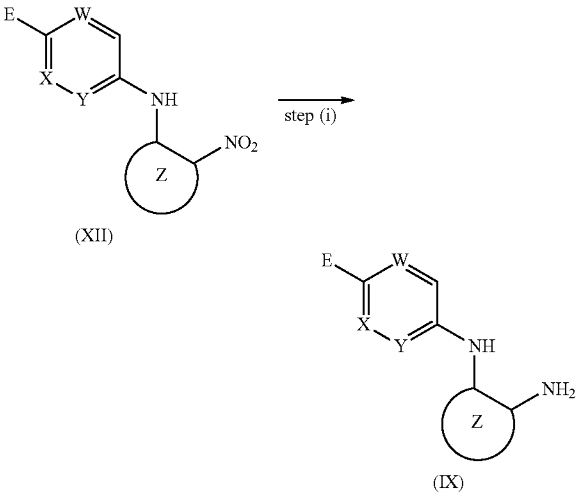

(XII)

(IX)

Anilines of formula (IX) can be prepared by the reduction of nitro compounds of formula (XIII) Suitable reactions conditions to transform (XIII) into (IX) are for example reduction in presence of Fe powder and ammonium chloride in a solvent such as a mixture ethanol/water for example at room temperature or with conventional heating.

Scheme 8

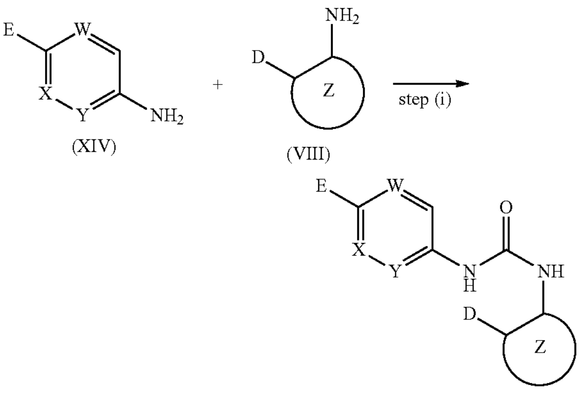

(XIV)

(VIII)

(X)

Ureas of formula (X) can be prepared by reaction of anilines of formula (XIV) and anilines of formula (VIII) in a suitable solvent e.g. dichloromethane or ethyl acetate with a carbonylating agent e.g. triphosgene preferentially prediluted in the same solvent in presence of a suitable base e.g. triethylamine or diisopropylethylamine at temperature ranging from 0° C. to room temperature.

Scheme 9

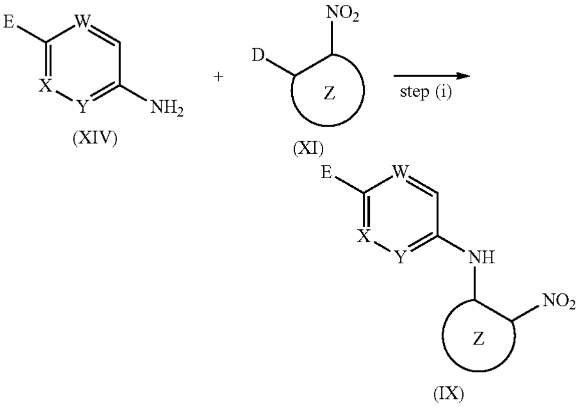

(XIV)

(XI)

(IX)

Compounds of formula (IX) can be prepared by metal catalysed cross coupling reactions. In this reaction an aniline of formula (XIV) and an aryl-halide derivative of formula (XI) wherein typically D=Cl, Br or I are reacted in the presence of a metal catalyst such as diacetoxypalladium (palladium(II) acetate), a suitable ligand such as 5-diphenylphosphanyl-9,9-dimethyl-xanthen-4-yl)-diphenyl-phosphane (Xantphos) and a suitable base such as cesium carbonate in a suitable solvent e.g. in 1,4-dioxane, with conventional heating or microwave heating.

Scheme 10

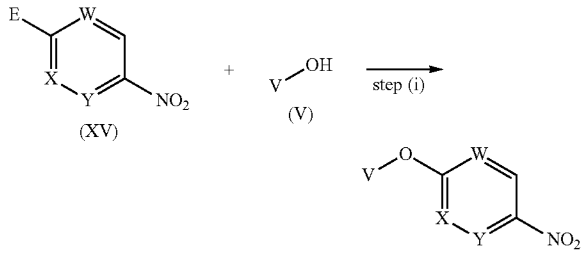

(XV) (V) (XII)

Compounds of formula (XII) can be prepared by nucleophilic aromatic substitution. In this reaction a aryl-halide derivative of formula (XV) wherein typically E=F or Cl and a phenol of formula (V) are reacted in the presence of a suitable base such as potassium carbonate in a suitable solvent, e.g. in N,N-dimethylacetamide, in N,N-dimethylformamide or in dimethyl sulfoxide, with conventional heating or microwave heating.

Scheme 11

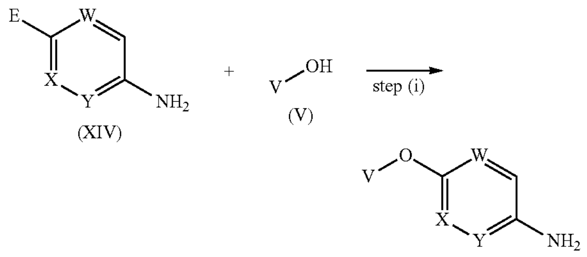

(XIV) (V) (VII)

Compounds of formula (VII) can be prepared by metal catalysed cross coupling reactions. In this reaction an aniline of formula (XIV) wherein typically E=Br or I and a phenol derivative of formula (V) are reacted in the presence of a metal catalyst such as copper(I) iodide, a suitable ligand such as pyridine-2-carboxylic acid and a suitable base such as cesium carbonate in a suitable solvent e.g. in N,N-dimethylacetamide, with conventional heating or microwave heating.

Alternatively, compounds of formula (VII) can be prepared by nucleophilic aromatic substitution. In this reaction an aryl-halide derivative of formula (XIV) wherein typically E=F or Cl and a phenol of formula (V) are reacted in the presence of a suitable base such as cesium carbonate in a suitable solvent, e.g. in dimethyl sulfoxide, with conventional heating or microwave heating.

Processes of the Invention

According to further aspects of the present invention are provided processes for the preparation of compounds of formula (I) or a salt, such as a pharmaceutically acceptable salt, and/or solvate thereof and/or derivative thereof, as well as processes for preparing intermediates or salts thereof in the synthesis of compounds of formula (I).

The processes of the invention are described above and include any individual step of a multi-step scheme.

Intermediates

The present invention also relates to novel intermediates in the synthesis of compounds of formula (I). Such novel intermediates include compounds of formulae (II), (II), (IV), (VI), (IX), (X) and (XIII). Thus, in one embodiment, there is provided a compound selected from the group consisting of:

a compound of formula (II):

(II)

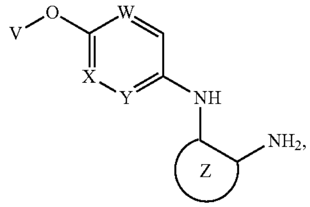

wherein V, W, X, Y and Z are as defined for the compound of formula (I);

a compound of formula (III):

(III)

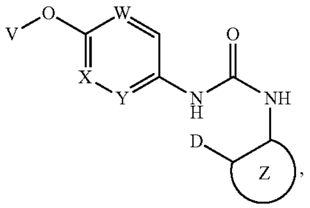

wherein V, W, X, Y and Z are as defined for the compound of formula (I) and D is halo, such as Cl, Br or I;

a compound of formula (IV):

(IV)

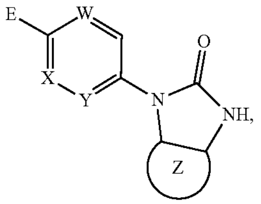

wherein W, X, Y and Z are as defined for the compound of formula (I) and E is halo, such as F or Cl;

a compound of formula (VI):

(VI)

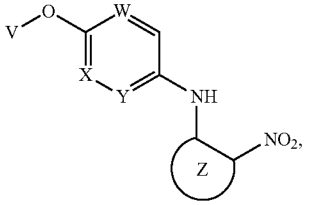

wherein V, W, X, Y and Z are as defined for the compound of formula (I);

a compound of formula (IX):

(IX)

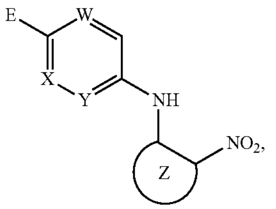

wherein W, X, Y and Z are as defined for the compound of formula (I) and E is halo, such as F or Cl;

a compound of formula (X):

(X)

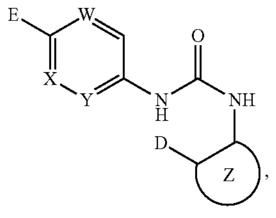

wherein W, X, Y and Z are as defined for the compound of formula (I), E is halo, such as F or $C_1$ and D is halo, such as Cl, Br or I; and a compound of formula (XIII):

(XIII)

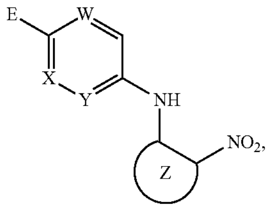

wherein W, X, Y and Z are as defined for the compound of formula (I) and E is halo, such as F or Cl;

Salts, such as pharmaceutically acceptable salts, of such intermediates are also provided by the present invention.

Kv3.1, Kv3.2, Kv3.3 and/or Kv3.4 Modulation

Compounds of formula (I) of the present invention are modulators of Kv3.1. Compounds of formula (I) may also be modulators of Kv3.2, Kv3.3 and/or Kv3.4. Compounds of the invention may be tested in the assay of Biological Example 1 to determine their modulatory properties for Kv3.1 and/or Kv3.2 and/or Kv3.3 and/or Kv3.4 channels.

A ‘modulator’ as used herein refers to a compound which is capable of producing at least 10% potentiation, and suitably at least 20% potentiation of whole-cell currents mediated by human Kv3.1 and/or human Kv3.2 and/or human Kv3.3 and/or human Kv3.4 channels recombinantly expressed in mammalian cells.

The term ‘Kv3.1, Kv3.2, Kv3.3 and/or Kv3.4’ shall be taken to mean the same as ‘Kv3.1 and/or Kv3.2 and/or Kv3.3 and/or Kv3.4’ and may also be referred to as ‘Kv3.1/Kv3.2/Kv3.3/Kv3.4’.

In one embodiment the modulator is capable of producing at least 10% potentiation and suitably at least 20% potentiation of whole-cell currents mediated by human Kv3.1 channels recombinantly expressed in mammalian cells. Suitably the $pEC_{50}$ of the modulator is in the range of 4-8 (such as 5-7.5).

In one embodiment the modulator is capable of producing at least 10% potentiation and suitably at least 20% potentiation of whole-cell currents mediated by human Kv3.2 channels recombinantly expressed in mammalian cells. Suitably the $pEC_{50}$ of the modulator is in the range of 4-8 (such as 5-7.5).

In one embodiment the modulator is capable of producing at least 10% potentiation and suitably at least 20% potentiation of whole-cell currents mediated by human Kv3.3 channels recombinantly expressed in mammalian cells. Suitably the $pEC_{50}$ of the modulator is in the range of 4-8 (such as 5-7.5).

In one embodiment the modulator is capable of producing at least 10% potentiation and suitably at least 20% potentiation of whole-cell currents mediated by human Kv3.4 channels recombinantly expressed in mammalian cells. Suitably the $pEC_{50}$ of the modulator is in the range of 4-8 (such as 5-7.5).

In another embodiment the modulator is capable of producing at least 10% potentiation and suitably at least 20% potentiation of whole-cell currents mediated by human Kv3.1 and Kv3.2 channels recombinantly expressed in mammalian cells.

In another embodiment the modulator is capable of producing at least 10% potentiation and suitably at least 20% potentiation of whole-cell currents mediated by human Kv3.1 and Kv3.3 channels recombinantly expressed in mammalian cells.

In another embodiment the modulator is capable of producing at least 10% potentiation and suitably at least 20% potentiation of whole-cell currents mediated by human Kv3.2 and Kv3.3 channels recombinantly expressed in mammalian cells.

In a further embodiment the modulator is capable of producing at least 10% potentiation and suitably at least 20% potentiation of whole-cell currents mediated by human Kv3.1, Kv3.2 and Kv3.3 channels recombinantly expressed in mammalian cells.

The compounds of formula (I) or their pharmaceutically acceptable salts and/or solvates and/or derivatives may be of use for the treatment or prophylaxis of a disease or disorder where a modulator of the Kv3.1 or Kv3.2 or Kv3.1 and Kv3.2 channels is required. As used herein, a modulator of Kv3.1 or Kv3.2 or Kv3.1 and Kv3.2 is a compound which alters the properties of these channels, either positively or negatively. In a particular aspect of the invention, the compound of formula (I) is a positive modulator. Compounds of the invention may be tested in the assay of Biological Example 1 to determine their modulatory properties.

In one embodiment of the invention the compounds of formula (I) or their pharmaceutically acceptable salts and/or solvates and/or derivatives thereof are selective for modulation of Kv3.1 channels over modulation of Kv3.2 channels. By selective, is meant that compounds demonstrate, for example, at least a 2 fold, 5 fold or 10 fold activity for Kv3.1 channels than for Kv3.2 channels. The activity of a compound is suitably quantified by its potency as indicated by an EC50 value.

In another embodiment of the invention, the compounds of formula (I) or their pharmaceutically acceptable salts and/or solvates and/or derivatives thereof are selective for modulation of Kv3.2 channels over modulation of Kv3.1 channels. Once again, by selective is meant that compounds demonstrate, for example at least a 2 fold, 5 fold or 10 fold activity for Kv3.2 channels than for Kv3.1 channels.

In a particular embodiment of the invention the compounds of formula (I) or their pharmaceutically acceptable salts and/or solvates and/or derivatives thereof demonstrate comparable activity between modulation of Kv3.1 and Kv3.2 channels, for example the activity for one channel is less than 2 fold that for the other channel, such as less than 1.5 fold or less than 1.2 fold.

In certain disorders it may be of benefit to utilise a modulator of Kv3.3 or Kv3.1, or Kv3.3 and Kv3.1 which demonstrates a particular selectivity profile between the two channels. For example a compound may be selective for modulation of Kv3.3 channels over modulation of Kv3.1 channels demonstrating, for example, at least a 2 fold, 5 fold or 10 fold activity for Kv3.3 channels than for Kv3.1 channels.

In another embodiment of the invention, the compounds of formula (I) or their pharmaceutically acceptable salts and/or solvates and/or derivatives thereof are selective for modulation of Kv3.1 channels over modulation of Kv3.3 channels. Once again, by selective is meant that compounds demonstrate, for example at least a 2 fold, 5 fold or 10 fold activity for Kv3.1 channels than for Kv3.3 channels.

In a particular embodiment of the invention, a compound may demonstrate comparable activity between modulation of Kv3.3 and Kv3.1 channels, for example the activity for each channel is less than 2 fold that for the other channel, such as less than 1.5 fold or less than 1.2 fold.

In certain disorders it may be of benefit to utilise a modulator of Kv3.3 or Kv3.2, or Kv3.3 and Kv3.2 which demonstrates a particular selectivity profile between the two channels. A compound may be selective for modulation of Kv3.3 channels over modulation of Kv3.2 channels demonstrating, for example, at least a 2 fold, 5 fold or 10 fold activity for Kv3.3 channels than for Kv3.2 channels.

In another embodiment of the invention, the compounds of formula (I) or their pharmaceutically acceptable salts and/or solvates and/or derivatives thereof are selective for modulation of Kv3.2 channels over modulation of Kv3.3 channels. Once again, by selective is meant that compounds demonstrate, for example at least a 2 fold, 5 fold or 10 fold activity for Kv3.2 channels than for Kv3.3 channels.

In another particular embodiment a compound may demonstrate comparable activity between modulation of Kv3.3 and Kv3.2 channels, for example the activity for each channel is less than 2 fold that for the other channel, such as less than 1.5 fold or less than 1.2 fold.

In a yet further particular embodiment of the invention a compound may demonstrate comparable activity between modulation of Kv3.3, Kv3.2 and Kv3.1 channels, for example the activity for each channel is less than 2 fold that for any other channel, such as less than 1.5 fold or less than 1.2 fold. The activity of a compound is suitably quantified by its potency as indicated by an EC50 value.

Therapeutic Methods

The invention also provides a compound of formula (I), or a pharmaceutically acceptable salt and/or solvate (e.g. salt) and/or derivative thereof, for use in the treatment or prophylaxis of a disease or disorder where a modulator of Kv3.1, Kv3.2, Kv3.3 and/or Kv3.4 is required, for example those diseases and disorders mentioned herein below.

The invention provides a method of treating or preventing a disease or disorder where a modulator of Kv3.1, Kv3.2, Kv3.3 and/or Kv3.4 is required, for example those diseases and disorders mentioned herein below, which comprises administering to a subject a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the treatment or prophylaxis of a disease or disorder where a modulator of Kv3.1, Kv3.2, Kv3.3 and/or Kv3.4 is required, for example those diseases and disorders mentioned herein below.

In one embodiment is provided a compound of formula (I) or a pharmaceutically acceptable salt and/or solvate thereof and/or derivative thereof for use as a medicament.

The term "treatment" or "treating" as used herein includes the control, mitigation, reduction, or modulation of the disease state or its symptoms.

The term "prophylaxis" is used herein to mean preventing symptoms of a disease or disorder in a subject or preventing recurrence of symptoms of a disease or disorder in an afflicted subject and is not limited to complete prevention of an affliction.

A subject will typically be a subject in need of treatment or prophylaxis according to the invention. Suitably the subject is a human.

Diseases or disorders that may be mediated by modulation of Kv3.1 and/or Kv3.2 channels may be selected from the list below. The numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10).

In one embodiment of the invention, the compounds of formula (I) or their pharmaceutically acceptable salts and/or solvates and/or derivatives may be of use for the treatment or prophylaxis of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Ménière's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease.

In one embodiment of the invention, the compounds of formula (I) or their pharmaceutically acceptable salts and/or solvates and/or derivatives may be of use for the treatment or prophylaxis of a disease or disorder selected from the group consisting of hearing disorders including hearing loss and tinnitus, schizophrenia, substance abuse disorders, pain such as neuropathic pain, inflammatory pain and miscellaneous pain, Lewy body dementia and Parkinson's disease.

In one embodiment of the invention, the compounds of formula (I) or their pharmaceutically acceptable salts and/or solvates and/or derivatives may be of use for the treatment or prophylaxis of a disease or disorder selected from the group consisting of Fragile-X, Rett's Disorder and Alzheimer's disease.

The invention provides a method for the prophylaxis or treatment of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Ménière's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease, which comprises administering to a subject a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative thereof, in the manufacture of a medicament for the treatment or prophylaxis of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Ménière's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease.

In a particular embodiment of the invention, there is provided a compound of formula (I) or their pharmaceutically acceptable salts and/or solvates (e.g. salts) and/or derivatives thereof for use in the treatment of prophylaxis of hearing disorders. Hearing disorders include auditory neuropathy, auditory processing disorder, hearing loss, which includes sudden hearing loss, noise induced hearing loss, substance-induced hearing loss, and hearing loss in adults over 60, over 65, over 70 or over 75 years of age (presbycusis), and tinnitus.

The compounds of formula (I) or their pharmaceutically acceptable salts and/or solvates (e.g. salts) and/or derivatives thereof may be of use for the treatment or prophylaxis of Ménière's disease, disorders of balance, and disorders of the inner ear.

In a particular embodiment of the invention, there is provided a compound of formula (I) or their pharmaceutically acceptable salts and/or solvates (e.g. salts) and/or derivatives thereof for use in the treatment or prophylaxis of schizophrenia. Schizophrenia includes the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The compounds of formula (I) or their pharmaceutically acceptable salts and/or solvates (e.g. salts) and/or derivatives thereof may be of use for the treatment or prophylaxis of depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90); Seasonal affective disorder.

The compounds of formula (I) or their pharmaceutically acceptable salts and/or solvates (e.g. salts) and/or derivatives thereof may be of use for the treatment or prophylaxis of Epilepsy, (including, but not limited to, localization-related epilepsies, generalized epilepsies, epilepsies with both generalized and local seizures, and the like), seizures associated with Lennox-Gastaut syndrome, seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, fever, infection, and the like), essential tremor, restless limb syndrome, partial and generalised seizures (including tonic, clonic, tonic-clonic, atonic, myoclonic, absence seizures), secondarily generalized seizures, temporal lobe epilepsy, absence epilepsies (including childhood, juvenile, myoclonic, photo- and pattern-induced), severe epileptic encephalopathies (including hypoxia-related and Rasmussen's syndrome), febrile convulsions, epilepsy partialis continua, progressive myoclonus epilepsies (including Unverricht-Lundborg disease and Lafora's disease), post-traumatic seizures/epilepsy including those related to head injury, simple reflex epilepsies (including photosensive, somatosensory and proprioceptive, audiogenic and vestibular), metabolic disorders commonly associated with epilepsy such as pyridoxine-dependent epilepsy, Menkes' kinky hair disease, Krabbe's disease, epilepsy due to alcohol and drug abuse (e.g. cocaine), cortical malformations associated with epilepsy (e.g. double cortex syndrome or subcortical band heterotopia), chromosomal anomalies associated with seizures or epilepsy such as Partial monosomy (15Q)/Angelman syndrome).

The compounds of formula (I) or their pharmaceutically acceptable salts and/or solvates (e.g. salts) and/or derivatives thereof may be of use for the treatment or prophylaxis of substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); *Cannabis*-Related Disorders such as *Cannabis* Dependence (304.30), *Cannabis* Abuse (305.20), *Cannabis* Intoxication (292.89), *Cannabis* Intoxication Delirium, *Cannabis*-Induced Psychotic Disorder, *Cannabis*-Induced Anxiety Disorder and *Cannabis*-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

The compounds of formula (I) or their pharmaceutically acceptable salts and/or solvates (e.g. salts) and/or derivatives thereof may be of use for the treatment or prophylaxis of anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00).

The compounds of formula (I) or their pharmaceutically acceptable salts and/or solvates (e.g. salts) and/or derivatives thereof may be of use for the treatment or prophylaxis of sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome.

The compounds of formula (I) or their pharmaceutically acceptable salts and/or solvates (e.g. salts) and/or derivatives thereof may be of use for the treatment or prophylaxis of hyperacusis and disturbances of loudness perception, including Fragile-X syndrome and autism.

The compounds of formula (I) or their pharmaceutically acceptable salts and/or solvates (e.g. salts) and/or derivatives thereof may be of use for the treatment or prophylaxis of Impulse control disorder including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

The compounds of formula (I) or their pharmaceutically acceptable salts and/or solvates (e.g. salts) and/or derivatives thereof may be of use for the treatment or prophylaxis of Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

The compounds of formula (I) or their pharmaceutically acceptable salts and/or solvates (e.g. salts) and/or derivatives thereof may be of use for the treatment or prophylaxis of Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9).

The compounds of formula (I) or their pharmaceutically acceptable salts and/or solvates (e.g. salts) and/or derivatives thereof may be of use for the treatment or prophylaxis of Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

The compounds of formula (I) or their pharmaceutically acceptable salts and/or solvates (e.g. salts) and/or derivatives thereof may be of use for the treatment or prophylaxis of Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

The compounds of formula (I) or their pharmaceutically acceptable salts and/or solvates (e.g. salts) and/or derivatives thereof may be of use for the treatment or prophylaxis of eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50).

The compounds of formula (I) or their pharmaceutically acceptable salts and/or solvates (e.g. salts) and/or derivatives thereof may be of use for the enhancement of cognition including the treatment of cognition impairment in other diseases such as schizophrenia, bipolar disorder, depression, other psychiatric disorders and psychotic conditions associated with cognitive impairment, e.g. Alzheimer's disease. Alternatively, the compounds of formula (I) or their pharmaceutically acceptable salts and/or solvates thereof may be of use for the prophylaxis of cognition impairment, such as may be associated with in diseases such as schizophrenia, bipolar disorder, depression, other psychiatric disorders and psychotic conditions associated with cognitive impairment, e.g. Alzheimer's disease.

The compounds of formula (I) or their pharmaceutically acceptable salts and/or solvates (e.g. salts) and/or derivatives thereof may be of use for the treatment or prophylaxis of ataxia including ataxia, in particular spinocerebellar ataxia, especially ataxia associated with R420H, R423H or F448L mutations.

The compounds of formula (I) or their pharmaceutically acceptable salts and/or solvates (e.g. salts) and/or derivatives thereof may be of use for the treatment or prophylaxis of pain including nociceptive, neuropathic, inflammatory or miscellaneous pain.

Nociceptive pain represents the normal response to noxious insult or injury of tissues such as skin, muscles, visceral organs, joints, tendons, or bones. Examples of nociceptive pain which form part of the invention include somatic pain: musculoskeletal (joint pain, myofascial pain) or cutaneous, which is often well localized; or visceral pain: hollow organs or smooth muscle.

Neuropathic pain is pain initiated or caused by a primary lesion or disease in the somatosensory nervous system. Sensory abnormalities range from deficits perceived as paraesthesia (numbness) to hypersensitivity (hyperalgesia or allodynia), and dysaesthesia (tingling and other sensations). Examples of neuropathic pain which form part of the invention include, but are not limited to, diabetic neuropathy, post-herpetic neuralgia, spinal cord injury pain, phantom limb (post-amputation) pain, and post-stroke central pain. Other causes of neuropathic pain include trauma, chemotherapy and heavy metal exposure.

Inflammatory pain occurs as a result of activation and sensitization of the nociceptive pain pathway by a variety of mediators released at a site of tissue inflammation. Mediators that have been implicated as key players in inflammatory pain are pro-inflammatory cytokines such IL-1-alpha, IL-1-beta, IL-6 and TNF-alpha, chemokines, reactive oxygen species, vasoactive amines, lipids, ATP, acid, and other factors released by infiltrating leukocytes, vascular endothelial cells, or tissue resident mast cells. Examples causes of inflammatory pain which form part of the invention include appendicitis, rheumatoid arthritis, inflammatory bowel disease, and herpes zoster.

Miscellaneous pain refers to pain conditions or disorders which are not easily classifiable. The current understanding of their underlying mechanisms is still rudimentary though specific therapies for those disorders are well known; they include cancer pain, migraine and other primary headaches and wide-spread pain of the fibromyalgia type.

Suitably, specific pain indications that may be mediated by a modulator of Kv3.1 and/or Kv3.2 and/or Kv3.3 and/or Kv3.4 channels are neuropathic pain and/or inflammatory pain.

Pain is a subjective condition and in a clinical setting tends to be measured by a patient's self-assessment. Therefore it can be difficult to measure and quantify pain threshold. For chronic pain, typically a subjective 11-point rating scale is used where 0 is no pain and 10 is the worst pain imaginable. Subjects generally record their worst pain over a given period, usually a day. A minimum mean baseline score is also recorded and response to the medication is measured relative to the baseline, for example, a reduction of at least 10%, 20%, 30%, 40% or 50% in pain from the baseline score may be observed.

Since individual responses to medicaments may vary, not all individuals may experience a reduction in pain from the baseline score. Consequently, suitably a reduction is observed in at least at least 10%, 20%, 30%, 40%, 50%, 60%, 70%, 80%, 90% or all individuals tested.

Therefore, in one embodiment of the invention, a reduction of at least 10%, 20%, 30%, 40% or 50% in pain from the baseline score is observed upon administration of a compound of formula (I) or a pharmaceutically acceptable salt, solvate and/or derivative thereof to a subject.

Administration can occur before an anticipated onset of pain or after the onset of pain. In cases where it is anticipated that development of a disease or disorder may lead to an increase in pain experienced by the subject, a compound of formula (I) or a pharmaceutically acceptable salt, solvate and/or derivative thereof can be administered. In cases where a subject is already experiencing pain a compound of formula (I) or a pharmaceutically acceptable salt, solvate and/or derivative thereof may be administered to a subject.

Treatment of the subject may continue for as long as treatment is required, for example, 1 day, 1 week, 2 weeks, 3 weeks, 1 month, 6 months, 1 year, more than 1 year more than 2 years, more than 5 years or more than 10 years. Therefore in one embodiment of the invention a compound of formula (I) or a pharmaceutically acceptable salt, solvate and/or derivative thereof, is administered to a subject for 1 day to 1 month, 1 week to 3 months, 1 month to 6 months, 3 months to 1 year or more than 1 year.

Reduction in pain in a subject can be measured by assessing the response to an external stimuli such as mechanical or thermal (e.g. cold) stimuli (such as described in the Experimental section). The reduction can either be considered as a percentage reversal (calculated by measuring the pre- and post-dose thresholds of the affected pain site with a non-affected pain site, such as described in more detail under Data Analysis in the Experimental Section) or by measuring withdrawal thresholds of the affected pain site. Preferably, the percentage reversal calculation is used.

Therefore, in one embodiment of the invention, the sensitivity to pain (such as neuropathic pain or inflammatory pain) is reversed by more than 20%, more than 30%, more than 40%, more than 50%, more than 60%, more than 70%, more than 80% or more than 90%, upon administration of a compound of formula (I) or a pharmaceutically acceptable salt, solvate and/or derivative thereof. Suitably, the sensitivity to pain is reversed by more than 80% or more than 90%.

Subjects may experience secondary benefits, such as one or more of improved function, mood, sleep, quality of life, reduced time off work.

In a particular embodiment, the compounds of formula (I) or their pharmaceutically acceptable salts and/or solvates (e.g. salts) and/or derivatives thereof may be of use for the treatment or prophylaxis of neuropathic pain.

In a particular embodiment, the compounds of formula (I) or their pharmaceutically acceptable salts and/or solvates (e.g. salts) and/or derivatives thereof may be of use for the treatment or prophylaxis of inflammatory pain.

In a particular embodiment, the compounds of formula (I) or their pharmaceutically acceptable salts and/or solvates (e.g. salts) and/or derivatives thereof may be of use for the treatment or prophylaxis of miscellaneous pain.

In some embodiments the pain is chronic pain.

In one embodiment is provided a compound of formula (I) for use in the prophylaxis of acute noise-induced hearing loss.

In one embodiment is provided a method for the prophylaxis of acute noise-induced hearing loss, comprising administering to a subject a compound of formula (I).

In one embodiment is provided the use of a compound of formula (I) in the manufacture of a medicament for the prophylaxis of acute noise-induced hearing loss.

Acute noise-induced hearing loss may be caused by events such as exposure to loud noise or a blast. In these cases, where it is anticipated that a future event may result in acute noise-induced hearing loss, the compound of formula (I) or a pharmaceutically acceptable salt, solvate and/or derivative thereof may be administered before the event in order to prevent or reduce acute noise-induced hearing loss. The administration of compound (1) or a pharmaceutically acceptable salt, solvate and/or derivative thereof may prevent any acute noise-induced hearing loss, or may reduce the severity of the acute noise-induced hearing loss or may mitigate other symptoms arising from acute noise-induced hearing loss, such as tinnitus.

"Acute hearing loss" is defined as hearing loss which occurs rapidly over a period of hours or days. For example, hearing loss may occur over a period of minutes, hours or days (for example over a period of up to 1 day, such as up to 2 days, 3 days, 4 days, 5 days, 6 days or 7 days).

Acute hearing loss will typically be caused by exposure to loud sound or blast. Hearing loss caused by exposure to loud sound or blast is referred to herein as "noise-induced induced hearing loss". "Acute noise induced hearing loss" is therefore hearing loss which occurs rapidly over a period of hours or days caused by exposure to loud sound or blast. Important symptoms of acute hearing loss include:

1. a shift in the auditory threshold, i.e. an increase in the minimum sound level of a pure tone that can be heard with no other sound present;
2. tinnitus; and
3. degradation in central auditory processing, for example impaired auditory temporal processing and/or speech understanding.

A "loud" noise or blast may be at least 90 dB, for example, at least 100 dB, at least 110 dB, at least 120 dB or at least 130 dB.

In one embodiment, administration of the compound of formula (I) or a pharmaceutically acceptable salt, solvate and/or derivative thereof is initiated before an event which is anticipated to cause noise-induced acute hearing loss. For example, administration of the compound of formula (I) or a pharmaceutically acceptable salt, solvate and/or derivative thereof may be initiated up to 2 weeks in advance, such as up to 1 week, 6 days, 5 days, 4 days, 3 days, 2 days, 24 h, 12 h, 6 h, 5 h, 4 h, 3 h, 2 h, 1 h, 30 minutes or up to 15 minutes in advance of an event which is anticipated to cause noise-induced acute hearing loss. The compound of formula (I) or a pharmaceutically acceptable salt, solvate and/or derivative thereof may be administered on multiple occasions before event which is anticipated to cause noise-induced acute hearing loss.

In one embodiment, a compound of formula (I) or a pharmaceutically acceptable salt, solvate and/or derivative thereof is administered in advance of potential exposure to a noise or blast which is anticipated to cause acute noise-induced hearing loss, for preventing or reducing the development of permanent tinnitus; for preventing or reducing the development of a permanent shift in auditory thresholds; or for preventing or reducing the development of permanently degraded central auditory processing, including for example auditory temporal processing and/or speech understanding.

It will be appreciated that administration in advance may be in circumstances where the subject is considered to be at risk of exposure to a noise or blast which is anticipated to cause acute noise-induced hearing loss and is not limited to those circumstances where such exposure ultimately occurs.

In one embodiment, administration of the compound of formula (I) or a pharmaceutically acceptable salt, solvate and/or derivative thereof is initiated during an event which is anticipated to cause noise-induced acute hearing loss. The compound of formula (I) or a pharmaceutically acceptable salt, solvate and/or derivative thereof may be administered on multiple occasions during an event which is anticipated to cause noise-induced acute hearing loss.

In one embodiment, a compound of formula (I) or a pharmaceutically acceptable salt, solvate and/or derivative thereof is initially administered during a noise or blast which is anticipated to cause acute noise-induced hearing loss, for preventing or reducing the development of permanent tinnitus; for preventing or reducing the development of a permanent shift in the auditory threshold; or for preventing or reducing the development of permanently degraded central auditory processing, including for example auditory temporal processing and/or speech understanding.

In one embodiment, administration of the compound of formula (I) or a pharmaceutically acceptable salt, solvate and/or derivative thereof is initiated after an event which is anticipated to cause acute noise-induced hearing loss.

Thus, in one embodiment, a compound of formula (I) or a pharmaceutically acceptable salt, solvate and/or derivative thereof is initially administered after a noise or blast which is anticipated to cause acute noise-induced hearing loss, for preventing or reducing the development of permanent tinnitus; for preventing or reducing the development of a permanent shift in the auditory threshold; or for preventing or reducing the development of permanently degraded central auditory processing, including for example auditory temporal processing and/or speech understanding.

When the compound of formula (I) is administered after an event which is anticipated to cause acute noise-induced hearing loss, such administration is normally undertaken during the "acute phase" i.e. before the hearing loss has become established.

In one embodiment, administration of the compound of formula (I) or a pharmaceutically acceptable salt, solvate and/or derivative thereof may be initiated up to 2 months after an event which is anticipated to cause noise-induced acute hearing loss, such as up to 1 month, 2 weeks, 1 week, 6 days, 5 days, 4 days, 3 days, 2 days, 24 h, 12 h, 6 h, 5 h, 4 h, 3 h, 2 h, 1 h, 30 minutes or up to 15 minutes after an event which is anticipated to cause acute noise-induced hearing loss.

The compound of formula (I) or a pharmaceutically acceptable salt, solvate and/or derivative thereof may be administered on multiple occasions after an event which is anticipated to cause noise-induced acute hearing loss.

The compound of formula (I) or a pharmaceutically acceptable salt, solvate and/or derivative thereof may be administered over a period of up to 7 days (for example, up to 1 day, up to 2 days, up to 3 days, up to 4 days, up to 5 days, up to 6 days or up to 7 days), for 1-2 weeks (for example, 7-8 days, 7-9 days, 7-10 days, 7-11 days, 7-12 days, 7-13 days or 7-14 days), for 2-4 weeks (for example, 2-3 weeks or 2-4 weeks) or for 1-2 months (for example, 4-6 weeks or 4-8 weeks).

The compound of formula (I) or a pharmaceutically acceptable salt, solvate and/or derivative thereof may initially be administered up to 1 day in advance, such as up to 2 days in advance, up to 3 days in advance, up to 5 days in advance, up to 1 week in advance, up to 2 weeks in advance or up to 1 month in advance of a noise or blast which is anticipated to cause acute noise-induced hearing loss, administration which is initiated at any point in advance exposure to a noise or blast which is anticipated to cause acute noise-induced hearing loss will typically continue for up to 2 months after exposure to the noise or blast which is anticipated to cause acute noise-induced hearing loss, such as for up to 1 month after, up to 3 weeks after, up to two weeks after, up to 1 week after, up to 5 days after, up to 3 days after, up to 2 days after, or up to 1 day after.

In one embodiment is provided a compound of formula (I) or a pharmaceutically acceptable salt, solvate and/or derivative thereof for use in preventing or reducing the development of a permanent shift in the auditory threshold, wherein the permanent shift in auditory threshold is reduced by at least 10 dB, such as at least 15 dB, at least 20 dB, at least 30 dB, at least 40 dB, or completely.

Pharmaceutical Compositions

For use in therapy the compounds of the invention are usually administered as a pharmaceutical composition. The invention also provides a pharmaceutical composition comprising a compound of formula (I), or a pharmaceutically acceptable salt and/or solvate (e.g. salt) and/or derivative thereof, and a pharmaceutically acceptable carrier or excipient.

In one embodiment, there is provided a pharmaceutical composition comprising a compound of formula (I), or a pharmaceutically acceptable salt and/or solvate (e.g. salt) and/or derivative thereof, for use in the treatment or prevention of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Mniere's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease.

In a further embodiment, there is provided a method for the prophylaxis or treatment of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Ménière's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease, which comprises administering to a subject a pharmaceutical composition comprising a compound of formula (I) or a pharmaceutically acceptable salt and/or solvate (e.g. salt) and/or derivative thereof.

The invention also provides the use of a pharmaceutical composition comprising a compound of formula (I), or a pharmaceutically acceptable salt and/or solvate thereof (e.g.

salt) and/or derivative thereof, in the manufacture of a medicament for the treatment or prophylaxis of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Ménière's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease.

The compounds of formula (I) or their pharmaceutically acceptable salts and/or solvates and/or derivatives thereof may be administered by any convenient method, e.g. by oral, parenteral, buccal, sublingual, nasal, rectal ortransdermal administration, and the pharmaceutical compositions adapted accordingly. Other possible routes of administration include intratympanic and intracochlear.

The compounds of formula (I) or their pharmaceutically acceptable salts and/or solvates and/or derivatives thereof which are active when given orally can be formulated as liquids or solids, e.g. as syrups, suspensions, emulsions, tablets, capsules or lozenges.

A liquid formulation will generally consist of a suspension or solution of the active ingredient (such as a compound of formula (I) or a pharmaceutically acceptable salt and/or solvate (e.g. salt) and/or derivative thereof) in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient (such as a compound of formula (I) or a pharmaceutically acceptable salt and/or solvate (e.g. salt) and/or derivative thereof) can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient (such as a compound of formula (I) or a pharmaceutically acceptable salt and/or solvate (e.g. salt) and/or derivative thereof) in a sterile aqueous carrier or parenterally acceptable oil, e.g. polyethylene glycol, polyvinyl pyrrolidone, lecithin, *arachis* oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively, the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches. In one embodiment the composition is in unit dose form such as a tablet, capsule or ampoule.

The composition may contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 mg to 1000 mg, more suitably 1.0 mg to 500 mg, and such unit doses may be administered more than once a day, for example two or three a day. Such therapy may extend for a number of weeks or months.

The dose provided to a subject will typically be a safe and effective dose, i.e. an amount providing an acceptable balance of desired benefits and undesired side effects. A "safe and effective amount" is intended to include an amount of a compound that is effective to achieve a desirable effect in treatment and/or prophylaxis of a disease-state. A desirable effect is typically clinically significant and/or measurable, for instance in the context of (a) preventing the disease-state from occurring in a mammal, in particular, when such mammal is predisposed to the disease-state but has not yet been diagnosed as having it; (b) inhibiting the disease-state, i.e., slowing or arresting its development; and/or (c) relieving the disease-state, i.e., causing regression of the disease state or a reduction in associated symptoms. The safe and effective amount may be one that is sufficient to achieve the desirable effect either when the compound is administered alone, or alternatively when it is administered in combination with one or more further APIs, which either are further compounds for use of the invention or are different from the compounds for use of the invention.

For avoidance of doubt, a "safe and effective amount" as recited herein can be achieved by any suitable dosage regimen, including but not limited to exemplary dosage regimens described elsewhere herein. Hence, for example, references herein to administering a safe and effective amount of a compound, such as by a particular administration route, include achieving the safe and effective amount via a single dose or by plural doses, such as administered by the specified administration route. For instance, orally administering a safe and effective amount includes both orally administering a single dose and orally administering any plural number of doses, provided that a safe and effective amount is thereby achieved by oral administration.

The invention provides, in a further aspect, a combination comprising a compound of formula (I) or a pharmaceutically acceptable, salt, solvate and/or derivative thereof (e.g. a combination comprising a compound of formula (I) or a pharmaceutically acceptable derivative thereof) together with a further pharmaceutically acceptable active ingredient or ingredients.

The invention provides a compound of formula (I), for use in combination with a further pharmaceutically acceptable active ingredient or ingredients.

When the compounds are used in combination with other therapeutic agents, the compounds may be administered either sequentially or simultaneously by any convenient route. Alternatively, the compounds may be administered separately.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations. The individual components of combinations may also be administered separately, through the same or different routes.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

Suitably, a compound of formula (I) or a pharmaceutically acceptable, salt, solvate and/or derivative thereof is administered orally.

Suitably, a compound of formula (I) or a pharmaceutically acceptable, salt, solvate and/or derivative thereof is administered at 2 to 400 mg per day, such as 2 to 300 mg per day, especially 5 to 250 mg per day.

Suitably, a compound of formula (I) or a pharmaceutically acceptable, salt, solvate and/or derivative thereof is administered once or twice per day.

Suitably, a compound of formula (I) or a pharmaceutically acceptable, salt, solvate and/or derivative thereof is administered for a period of at least three months.

Desirably, a compound of formula (I) or a pharmaceutically acceptable, salt, solvate and/or derivative thereof is administered orally, once or twice per day, at 2 to 400 mg per day, such as 2 to 300 mg per day, especially 5 to 250 mg per day.

A human subject may be an adult, such as aged 18 to 65. Alternatively, a human subject may be 66 years old or older. A compound of formula (I) or a pharmaceutically acceptable, salt, solvate and/or derivative thereof may be administered to a human subject of less than 18 years of age, such as 4 to 17 years old. Administration to a human subject of less than 18 years of age may be of particular relevance in the context of progressive myoclonic epilepsy and Fragile X syndrome.

For convenience and to assist with patient compliance, delivery technologies such as patches or implants may be used to deliver a compound of formula (I) or a pharmaceutically acceptable, salt, solvate and/or derivative thereof over a sustained period of time e.g. at least one week or at least 4 weeks.

Experimental

The invention is illustrated by the compounds described below. The following examples describe the laboratory synthesis of specific compounds of the invention and are not meant to limit the scope of the invention in any way with respect to compounds or processes. It is understood that, although specific reagents, solvents, temperatures and time periods are used, there are many possible equivalent alternatives that can be used to produce similar results. This invention is meant to include such equivalents.

Analytical Equipment

Starting materials, reagents and solvents were obtained from commercial suppliers and used without further purification unless otherwise stated. Unless otherwise stated, all compounds with chiral centres are racemic. Where reactions are described as having been carried out in a similar manner to earlier, more completely described reactions, the general reaction conditions used were essentially the same. Work up conditions used were of the types standard in the art, but may have been adapted from one reaction to another. The starting material may not necessarily have been prepared from the batch referred to. Compounds synthesised may have various purities, ranging from for example 85% to 99%. Calculations of number of moles and yield are in some cases adjusted for this.

HPLC-Mass spectra (HPLC-MS) were taken on an Agilent 1100 Series LC/MSD Mass Spectrometer coupled with HPLC instrument Agilent 1100 Series, operating in positive electrospray ionization mode and in acidic gradient conditions.

Quality Control (3 minutes method): LC/MS-ES+ under acidic conditions was performed on a Zorbax SB C18 column (1.8 μm 3×50 mm). Mobile phase: A: (H2O+0.05% TFA by vol.)/B: (CH3CN+0.05% TFA by vol). Gradient: t=0 min 0% (B), from 0 to 95% (B) in 2.5 min, 95% (B) for 0.2 min, from 95 to 100% (B) in 0.2 min, 100% (B) for 0.4 min, from 100% to 0% (B) in 0.1 min. Stop time 4 min. Column T=60° C. Flow rate: 1.5 ml/min. Mass range ES+: (100-1000 amu, F=60). UV detection wavelengths: DAD 1A=220.8, DAD 1B=254.8. The use of this methodology is indicated by "QC_3_MIN" in the analytic characterization of the described compounds.

It will be appreciated that retention times observed during chromatography can vary from preparation to preparation due to factors such as the age of column.

Chiral control: LC/MS-ES+ under acidic conditions was performed on a CHIRALCEL® OD-H (250×4.6 mm-5 um). Mobile phase: A: ($H_2O$+0.05% TFA by vol.)/B: (CH3CN+0.05% TFA by vol). Gradient: t=0-6 min 35% (B), t=6-40 min from 35% to 50% (B), t=40-45 min from 50% to 70% (B), t=45-50 min from 70% to 35% (B), t=50-55 min 35% (B). Stop time 60 min. Column T=40° C. Flow rate: 1.0 ml/min. UV detection wavelengths: DAD 1A=220.8, DAD 1B=254.8.

Proton Magnetic Resonance (NMR) spectra were recorded either on Varian instruments at 300, 400, 500 or 600 MHz, or on Bruker instruments at 400 MHz. Chemical shifts are reported in ppm (δ) using the residual solvent line as internal standard. Splitting patterns are designed as s (singlet), br.s (broad singlet), d (doublet), t (triplet), q (quartet), dd (doublet of doublets), dt (doublet of triplets) and m (multiplet). The NMR spectra were recorded at temperatures ranging from 25 to 60° C.

2D NMR NOESY experiments were acquired with a mixing time of 500 ms using a spectral width of 3355 Hz in both f1 and f2. A total of 256 increments were collected, processed to 1 K with linear prediction, 8 scans each. Data were processed with sine bell shift in both dimensions and with lb=0.3 Hz in f1. In a number of preparations, purification was performed using Biotage automatic flash chromatography (SP1 and SP4) or Flash Master Personal systems.

Flash chromatographies were carried out on silica gel 230-400 mesh (supplied by Merck AG Darmstadt, Germany) or on silica gel 300-400 mesh (supplied by Sinopharm Chemical Reagent Co., Ltd.), Varian Mega Be-Si pre-packed cartridges, pre-packed Biotage silica cartridges (e.g. Biotage SNAP cartridge), pre-packed Modus silica cartridges.

Abbreviations

ACN acetonitrile
aq aqueous
Boc tert-Butyloxycarbonyl
DCM dichloromethane
DIPEA N,N-diisopropylethylamine
EtOAc ethyl acetate
g gram(s)
h(rs) hour(s)
HATU (O-7-azabenzotriazol-1-yl)-N,N,N',N'-tetramethyluroniumhexafluoro phosphate)
HCl hydrogen chloride
LC/MS Liquid Chromatography-Mass Spectrometry
Me methyl
mg milligram(s)
min minute(s)
mL millilitre(s)
mmol millimole
m/z mass to charge ratio
NMR Nuclear Magnetic Resonance
MTBE methyl tert-butyl ether
rt room temperature
T temperature
T3P propanephosphonic acid anhydride
TBTU benzotriazol-1-yl-N,N,N',N'-tetramethyluronium tetrafluoroborate
TEA triethylamine
TFA trifluoroacetic acid
vol volume
wt. weight Experimental Procedures Intermediate 1

2-[(3,3-dimethyl-2H-benzofuran-4-yl)oxy]-5-nitro-pyridine

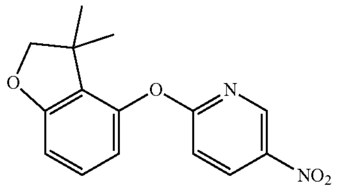 [SMILES: CC1(C)COc2cccc(Oc3ccc([N+](=O)[O-])cn3)c21]

A mixture of 2-chloro-5-nitropyridine (60 mg, 0.38 mmol), 3,3-dimethyl-2H-benzofuran-4-ol (Intermediate 50 WO2012/076877, 8 mg, 0.42 mmol) and dipotassium carbonate (potassium carbonate) (79 mg, 0.58 mmol) in N,N-dimethylacetamide (1.5 mL) was stirred at 120° C. for 1 hour. The mixture was then diluted with water and extracted with ethyl acetate (3×20 mL). The combined organic layers were washed with brine (30 mL), separated, dried over sodium sulfate, filtered and concentrated under vacuum to afford the title compound 2-[(3,3-dimethyl-2H-benzofuran-4-yl)oxy]-5-nitro-pyridine (105 mg) as a raw brown semi-solid.

LC/MS: QC_3_MIN: Rt=2.54 min m/z 287 [M+H]+

Intermediate 2

5-nitro-2-[3-(trifluoromethoxy)phenoxy]pyridine

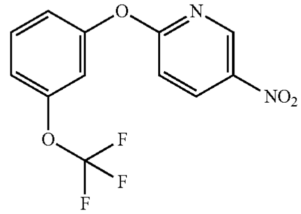

Intermediate 2 was prepared using the methodology already described for Intermediate 1 replacing 3,3-dimethyl-2H-benzofuran-4-ol (Intermediate 50 WO2012/076877) with 3-(trifluoromethoxy)phenol.

LC/MS: QC_3_MIN: Rt=2.54 min m/z 301 [M+H]+

Intermediate 3

5-nitro-2-{2H-spiro[1-benzofuran-3,1'-cyclopropane]oxy}pyrimidine

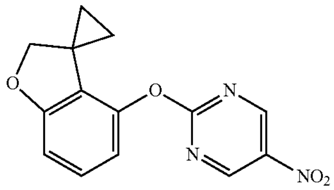

To a solution of 2-chloro-5-nitropyrimidine (250 mg, 1.57 mmol) in acetonitrile (2.5 mL), 2H-spiro[1-benzofuran-3,1'-cyclopropan]-4-ol (Intermediate 85 WO2012/076877, 280 mg, 1.73 mmol) and potassium carbonate (325 mg, 2.36 mmol) were added, and the mixture was stirred for 1 hour at 80° C. The reaction crude was diluted with ethyl acetate (20 mL) and washed with brine (20 mL). The organic layer was dried over sodium sulphate, filtered and evaporated to dryness, affording the title compound 5-nitro-2-{2H-spiro[1-benzofuran-3,1'-cyclopropane]oxy}pyrimidine (430 mg) as a brown solid.

LC/MS: QC_3_MIN: Rt=2.27 min m/z 286 [M+H]+

Intermediate 4

5-nitro-2-[3-(methoxy)phenoxy]pyrimidine

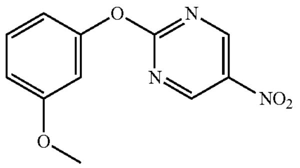 [SMILES: COc1cccc(Oc2ncc([N+](=O)[O-])cn2)c1]

Intermediate 4 was prepared using the methodology already described for Intermediate 3 replacing 2H-spiro[1-benzofuran-3,1'-cyclopropan]-4-ol (Intermediate 85 WO2012/076877) with 3-methoxy phenol.

LC/MS: QC_3_MIN: Rt=2.16 min m/z 248 [M+H]+

Intermediate 5

5-nitro-2-[3-(trifluoromethoxy)phenoxy]pyrimidine

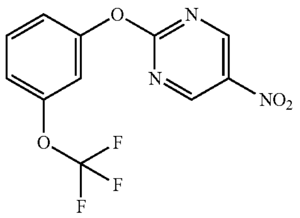 [SMILES: O=[N+]([O-])c1cnc(Oc2cccc(OC(F)(F)F)c2)nc1]

A mixture of 3-(trifluoromethoxy)phenol (2.4562 g, 13.791 mmol), 2-chloro-5-nitropyrimidine (2 g, 12.537 mmol) and dipotassium carbonate (potassium carbonate) (2.5991 g, 18.805 mmol) in acetonitrile (10 mL) was stirred at rt for 5 h. The mixture was diluted with ethyl acetate (40 ml) and washed with brine (40 ml). Phases were separated and the organic layer was dried over $Na_2SO_4$, filtered and evaporated affording 5-nitro-2-[3-(trifluoromethoxy)phenoxy]pyrimidine (3.1 g) that was used in the next step without further purification.

LC/MS: QC_3_MIN: Rt=2.71 min m/z 302 [M+H]+

Intermediate 6

6-[(3,3-dimethyl-2H-benzofuran-4-yl)oxy]pyridin-3-amine

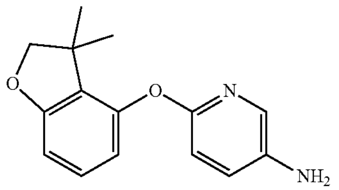

To a suspension of 2-[(3,3-dimethyl-2H-benzofuran-4-yl)oxy]-5-nitro-pyridine (Intermediate 1, 105 mg, 0.37 mmol) in ethanol (1.6 mL)/water (0.4 mL), iron (82 mg, 1.47 mmol) and ammonium chloride (79 mg, 1.47 mmol) were added and the reaction mixture was stirred at 80° C. for 1 h. The solids were filtered off and the filtrate was concentrated under vacuum. The residue was dissolved in ethyl acetate (20 mL) and washed with brine (20 mL). The organic layer was dried over sodium sulfate, filtered and evaporated. The residue was purified by flash chromatography (Biotage System) on silica gel using a SFAR 5 g as column and cyclohexane/ethyl acetate from 80:20 to 30:70 as eluent affording 6-[(3,3-dimethyl-2H-benzofuran-4-yl)oxy]pyridin-3-amine (60 mg) as a yellow solid.

LC/MS: QC_3_MIN: Rt=1.95 min m/z 257[M+H]+

Intermediate 6 may also be prepared as described for WO2012076877 Intermediate 59.

The following compounds were prepared using analogous methods to the foregoing methodology, replacing 2-[(3,3-dimethyl-2H-benzofuran-4-yl)oxy]-5-nitro-pyridine (Intermediate 1) with the appropriate nitro derivative. The reactions in the table were performed at room temperature (rt) with reaction times ranging from 16 h to 24 h. The conditions for each case are specified in the table. Final products were purified by flash-chromatography (Silica cartridge using Cyclohexane/EtOAc or DCM/Methanol as eluent or C-18 cartridge using water/acetonitrile as eluent).

| Int. | Structure | Name | Nitro Derivative | T(° C.)/ h | LC-MS |
|---|---|---|---|---|---|
| 7 | 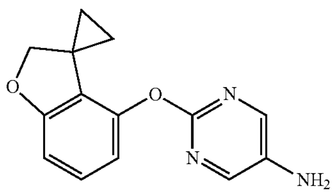 [SMILES: Nc1cnc(Oc2cccc3c2C2(CC2)CO3)nc1] | 2-{2H-spiro[1-benzofuran-3,1'-cyclopropane]oxy}pyrimidin-5-amine | 5-nitro-2-{2H-spiro[1-benzofuran-3,1'-cyclopropane]oxy}pyrimidine (Intermediate 3) | rt for 24 h | LC/MS: QC_3_MIN: Rt = 1.93 min m/z 256 [M + H]$^+$ |
| 8 | 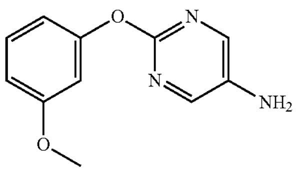 [SMILES: COc1cccc(Oc2ncc(N)cn2)c1] | 2-(3-methoxyphenoxy)pyrimidin-5-amine | 2-(3-methoxyphenoxy)-5-nitro-pyrimidine (Intermediate 4) | rt for 18 h | LC/MS: QC_3_MIN: Rt = 1.73 min m/z 218 [M + H]$^+$ |

-continued

| Int. | Structure | Name | Nitro Derivative | T(° C.)/ h | LC-MS |
|---|---|---|---|---|---|
| 9 | 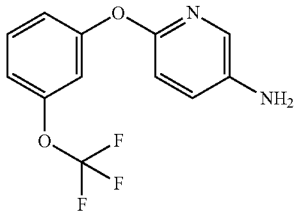 [SMILES: Nc1ccc(Oc2cccc(OC(F)(F)F)c2)nc1] | 6-[3-(trifluoromethoxy) phenoxy]pyridin-3-amine | 5-nitro-2-[3-(trifluoromethoxy) phenoxy]pyridine (Intermediate 2) | rt for 24 h | LC/MS: QC_3_MIN: Rt = 2.13 min m/z 271 M + H]+ |
| 10 | 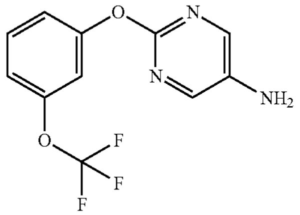 [SMILES: Nc1cnc(Oc2cccc(OC(F)(F)F)c2)nc1] | 6-[3-(trifluoromethoxy) phenoxy]pyrimidin-3-amine | 5-nitro-2-[3-(trifluoromethoxy) phenoxy]pyrimidine (Intermediate 5) | rt for 16 h | LC/MS: QC_3_MIN: Rt = 2.13 min m/z 272 [M + H]+ |

Intermediate 10 (Alternative Route

6-[3-(trifluoromethoxy)phenoxy]pyrimidin-3-amine

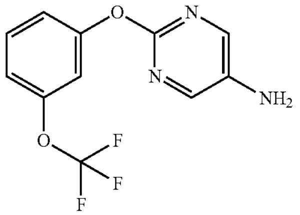 [SMILES: Nc1cnc(Oc2cccc(OC(F)(F)F)c2)nc1]

A mixture of 2-chloro-5-aminopyrimidine (48 mg, 0.3705 mmol), 3-(Trifluoromethoxy)phenol (103.42 mg, 0.5807 mmol) (0.075 mL), cesium carbonate (250 mg, 0.7673 mmol) and dimethyl sulfoxide (1 mL) was stirred at 120° C. for 16 h. The reaction mixture was partitioned between saturated aqueous $NaHCO_3$ (30 mL) and ethyl acetate (50 mL). The organic layer was separated, washed with brine (10 mL), dried over anhydrous magnesium sulfate, filtered, then concentrated in vacuo. The residue was purified by flash chromatography (Biotage System) on silica gel using a MODUS 12 g as column and Cyclohexane: Ethyl acetate (0-100%) as eluent. The appropriate fractions were combined and evaporated to dryness. The residues were purified by reverse phase chromatography using a SNAP C-18 12 g column, eluting with water and acetonitrile from 95:5 to 5:95. The appropriate fractions were combined and evaporated to dryness, producing 2-[3-(trifluoromethoxy)phenoxy]pyrimidin-5-amine (26 mg) as a colourless oil.

LC/MS: QC_3_MIN: Rt=2.13 min m/z 272 [M+H]+

Intermediate 11

5-spiro[2H-benzofuran-3,1'-cyclopropane]-4-yloxy-pyrazin-2-amine

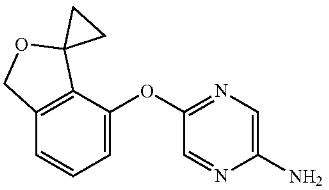 [SMILES: Nc1cnc(Oc2cccc3c2C2(CC2)OC3)cn1]

5-bromopyrazin-2-amine (600 mg, 3.45 mmol), spiro[2H-benzofuran-3,1'-cyclopropane]-4-ol (Intermediate 85 WO2012076877, 559 mg, 3.45 mmol), caesium carbonate (2.25 g, 6.90 mmol), copper(I) iodide (131 mg, 0.69 mmol) and pyridine-2-carboxylic acid (254 mg, 2.07 mmol) were mixed in N,N-dimethylacetamide (7 mL). The reaction mixture was split into two different vials and each vial was submitted to an argon-vacuum cycle and stirred at 120° C. for 2 hours. The reaction mixtures were diluted with ethyl acetate (20 mL each) and filtered over cellulose. The filtrate was washed twice with a $NH_4Cl$ saturated solution (20 mL), brine (20 mL), dried over sodium sulfate and evaporated to dryness. The residue was purified by flash chromatography (Biotage System) on silica gel using a SFAR 10 g as column and cyclohexane/ethyl acetate from 80:20 to 40:60 as eluent, affording the title compound 5-spiro[2H-benzofuran-3,1'-cyclopropane]-4-yloxypyrazin-2-amine (245 mg) as a brown powder.

LC/MS: QC_3_MIN: Rt=2.08 min m/z 256[M+H]+

The following compounds were prepared using analogous methods to the foregoing methodology, replacing spiro[2H-benzofuran-3,1'-cyclopropane]-4-ol (Intermediate 85 WO2012076877) with the appropriate phenol. Final products were purified by flash-chromatography (Silica cartridge using Cyclohexane/EtOAc or DCM/Methanol as eluent or C-18 cartridge using water/acetonitrile as eluent).

| Int. | Structure | Name | Phenol Derivative | LC-MS |
|---|---|---|---|---|
| 12 | 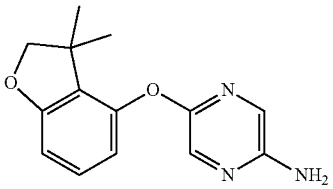 | 5-[(3,3-dimethyl-2H-benzofuran-4-yl)oxy]pyrazin-2-amine | 3,3-dimethyl-2H-benzofuran-4-ol (Intermediate 50 WO2012/076877) | LC/MS: QC_3_MIN: Rt = 2.15 min m/z 258 [M + H]+ |
| 13 | 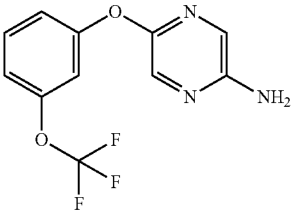 [SMILES: Nc1cnc(Oc2cccc(OC(F)(F)F)c2)cn1] | 5-[3-(trifluoromethoxy)phenoxy]pyrazin-2-amine | 3-trifluoromethoxy phenol | LC/MS: QC_3_MIN: Rt = 2.19 min m/z 272 [M + H]+ |
| 14 | 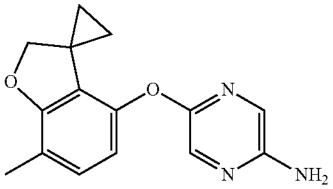 [SMILES: Cc1ccc(Oc2cnc(N)cn2)c2c1OCC21CC1] | 5-(7-methylspiro[2H-benzofuran-3,1'-cyclopropane]-4-yl)oxypyrazin-2-amine | 7-methylspiro[2H-benzofuran-3,1'-cyclopropane]-4-ol (Intermediate 156 WO2012/076877) | LC/MS: QC_3_MIN: Rt = 2.12 min m/z 270 [M + H]+ |

Intermediate 15

N-[6-(7-methylspiro[2H-benzofuran-3,1'-cyclopropane]-4-yl)oxy-3-pyridyl]-3-nitro-pyridin-2-amine

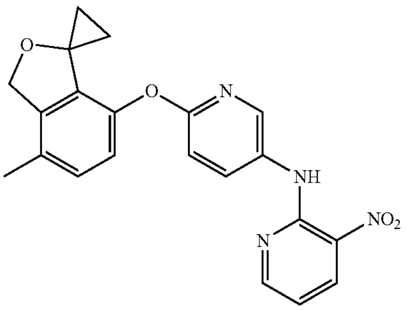 [SMILES: Cc1ccc(Oc2ccc(Nc3ncccc3[N+](=O)[O-])cn2)c2c1COC21CC1]

6-(7-methylspiro[2H-benzofuran-3,1'-cyclopropane]-4-yl)oxypyridin-3-amine (WO2012/076877 Intermediate 158, 50 mg, 0.19 mmol), caesium carbonate (122 mg, 0.37 mmol) and 2-chloro-3-nitro-pyridine (30 mg, 0.17 mmol) were dissolved in 1,4-dioxane (2 mL) and diacetoxypalladium (palladium(II) acetate) (42 mg, 0.19 mmol) and (5-diphenylphosphanyl-9,9-dimethyl-xanthen-4-yl)-diphenyl-phosphane (Xantphos) (9 mg, 0.01 mmol) were added. A vacuum-argon cycle was applied three times and then, the mixture was stirred at 95° C. for 2 hours. After cooling, the reaction was diluted with EtOAc (20 mL) and washed with an $NH_4Cl$ saturated solution (20 mL). The two layers were separated and the organic one washed with brine (20 mL), dried over $Na_2SO_4$, filtered and evaporated under vacuum affording the title compound N-[6-(7-methylspiro[2H-benzofuran-3,1'-cyclopropane]-4-yl)oxy-3-pyridyl]-3-nitro-pyridin-2-amine (82 mg) as a brown solid. The raw material was used in the next step without further purification.

LC/MS: QC_3_MIN: Rt=2.67 min m/z 391[M+H]+

The following compounds were prepared using analogous methods to the foregoing methodology, replacing 6-(7-methylspiro[2H-benzofuran-3,1'-cyclopropane]-4-yl)oxy-pyridin-3-amine (WO2012/076877 Intermediate 158) with the appropriate aniline and 2-chloro-3-nitro-pyridine with the appropriate nitro derivative. This methodology can also be employed using nitrogen instead of argon.

| Int. | Structure | Name | Aniline | Nitro derivative | LC-MS |
|---|---|---|---|---|---|
| 16 | 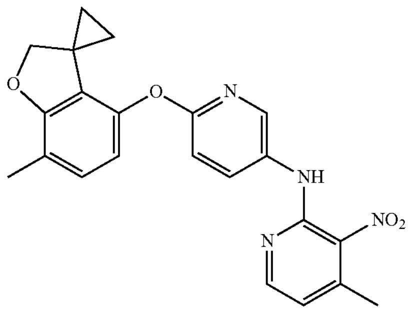 | 4-methyl-N-[6-(7-methylspiro[2H-benzofuran-3,1'-cyclopropane]-4-yl)oxy-3-pyridyl]-3-nitro-pyridin-2-amine | 6-(7-methylspiro[2H-benzofuran-3,1'-cyclopropane]-4-yl)oxypyridin-3-amine (WO2012/076877 Intermediate 158) | 2-chloro-6-methyl-3-nitro-pyridine | LC/MS: QC_3_MIN: Rt = 2.71 min; m/z 405 [M + H]+. |
| 17 | 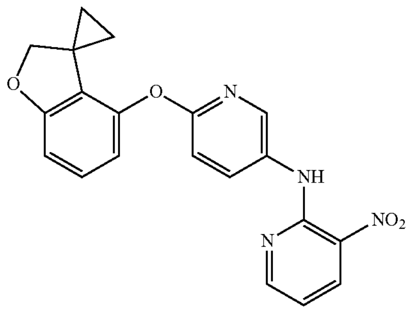 | 3-nitro-N-(6-spiro [2H-benzofuran-3,1'-cyclopropane]-4-yloxy-3-pyridyl)pyridin-2-amine | 6-spiro[2H-benzofuran-3,1'-cyclopropane]-4-yloxypyridin-3-amine (WO2012/076877 Intermediate 87) | 2-chloro-3-nitro-pyridine | LC/MS: QC_3_MIN: Rt = 2.55 min; m/z 377 [M + H]+. |
| 18 | 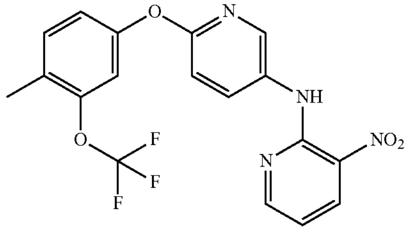 [SMILES: Cc1ccc(Oc2ccc(Nc3ncccc3[N+](=O)[O-])cn2)cc1OC(F)(F)F] | N-[6-[4-methyl-3-(trifluoromethoxy) phenoxy]-3-pyridyl]-3-nitro-pyridin-2-amine | 6-[4-methyl-3-(trifluoromethoxy) phenoxy]pyridin-3-amine (WO2011/069951 Intermediate 147) | 2-chloro-3-nitro-pyridine | LC/MS: QC_3_MIN: Rt = 2.74 min; m/z 407 [M + H]+. |

-continued

| Int. | Structure | Name | Aniline | Nitro derivative | LC-MS |
|---|---|---|---|---|---|
| 19 | 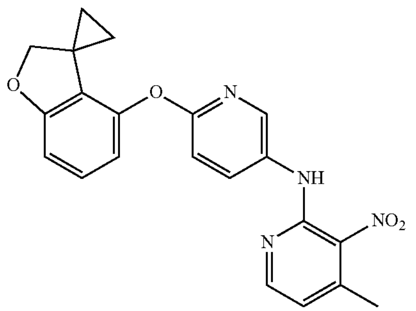 | 4-methyl-3-nitro-N-(6-spiro[2H-benzofuran-3,1'-cyclopropane]-4-yloxy-3-pyridyl)pyridin-2-amine | 6-spiro[2H-benzofuran-3,1'-cyclopropane]-4-yloxypyridin-3-amine (WO2012/076877 Intermediate 87) | 2-chloro-6-methyl-3-nitro-pyridine | LC/MS: QC_3_MIN: Rt = 2.59 min; m/z 391 [M + H]+. |
| 20 | 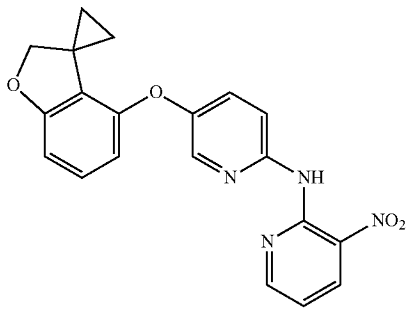 [SMILES: O=[N+]([O-])c1cccnc1Nc1ccc(Oc2cccc3c2C2(CC2)CO3)cn1] | 3-nitro-N-(5-spiro [2H-benzofuran-3,1'-cyclopropane]-4-yloxy-2-pyridyl)pyridin-2-amine | 5-spiro[2H-benzofuran-3,1'-cyclopropane]-4-yloxypyridin-2-amine (WO2017/103604 intermediate 24) | 2-chloro-3-nitro-pyridine | LC/MS: QC_3_MIN: Rt = 2.53 min; m/z 377 [M + H]+. |
| 21 | 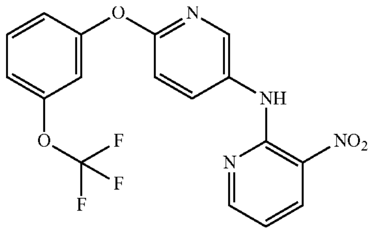 [SMILES: O=[N+]([O-])c1cccnc1Nc1ccc(Oc2cccc(OC(F)(F)F)c2)nc1] | 3-nitro-N-[6-[3-(trifluoromethoxy) phenoxy]-3-pyridyl]pyridin-2-amine | 6-[3-(trifluoromethoxy) phenoxy]pyridin-3-amine (Intermediate 9) | 2-chloro-3-nitro-pyridine | LC/MS: QC_3_MIN: Rt = 2.66 min; m/z 393 [M + H]+. |

-continued

| Int. | Structure | Name | Aniline | Nitro derivative | LC-MS |
|---|---|---|---|---|---|
| 22 | 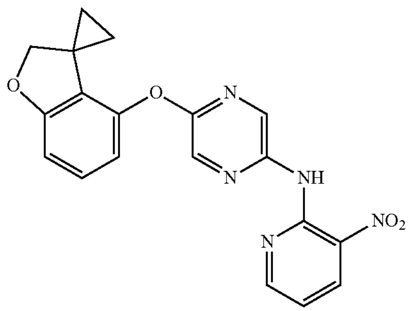 [SMILES: O=[N+]([O-])c1cccnc1Nc1cnc(Oc2cccc3c2C2(CC2)CO3)cn1] | N-(3-nitro-2-pyridyl)-5-spiro[2H-benzofuran-3,1'-cyclopropane]-4-yloxy-pyrazin-2-amine | 5-spiro[2H-benzofuran-3,1'-cyclopropane]-4-yloxypyrazin-2-amine (Intermediate 11) | 2-chloro-3-nitro-pyridine | LC/MS: QC_3_MIN: Rt = 2.61 min; m/z 378 [M + H]+. |
| 23 | 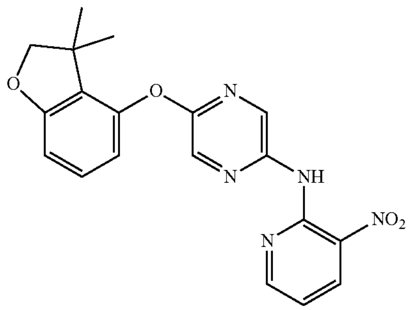 | 5-[(3,3-dimethyl-2H-benzofuran-4-yl)oxy]-N-(3-nitro-2-pyridyl)pyrazin-2-amine | 5-[(3,3-dimethyl-2H-benzofuran-4-yl)oxy]pyrazin-2-amine (Intermediate 12) | 2-chloro-3-nitro-pyridine | LC/MS: QC_3_MIN: Rt = 2.76 min; m/z 380 [M + H]+. |
| 24 | 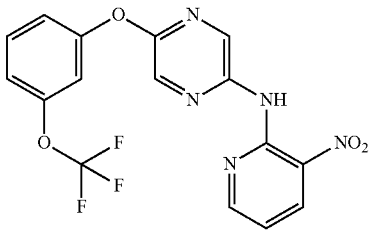 [SMILES: O=[N+]([O-])c1cccnc1Nc1cnc(Oc2cccc(OC(F)(F)F)c2)cn1] | N-(3-nitro-2-pyridyl)-5-[3-(trifluoromethoxy)phenoxy]pyrazin-2-amine | 5-[3-(trifluoromethoxy)phenoxy]pyrazin-2-amine (Intermediate 13) | 2-chloro-3-nitro-pyridine | LC/MS: QC_3_MIN: Rt = 2.85 min; m/z 394 [M + H]+. |

-continued

| Int. | Structure | Name | Aniline | Nitro derivative | LC-MS |
|---|---|---|---|---|---|
| 25 | 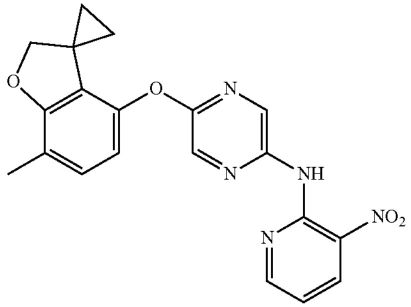 | 5-(7-methylspiro[2H-benzofuran-3,1'-cyclopropane]-4-yl)oxy-N-(3-nitro-2-pyridyl)pyrazin-2-amine | 5-(7-methylspiro[2H-benzofuran-3,1'-cyclopropane]-4-yl)oxypyrazin-2-amine (Intermediate 14) | 2-chloro-3-nitro-pyridine | LC/MS: QC_3_MIN: Rt = 2.74 min; m/z 392 [M + H]+. |
| 26 | 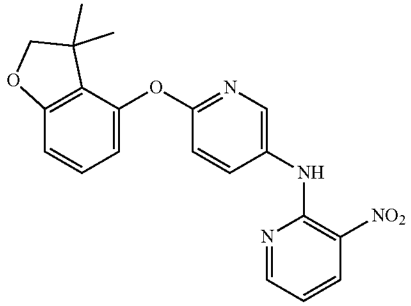 [SMILES: CC1(C)COc2cccc(Oc3ccc(Nc4ncccc4[N+](=O)[O-])cn3)c21] | N-[6-[(3,3-dimethyl-2H-benzofuran-4-yl)oxy]-3-pyridyl]-3-nitro-pyridin-2-amine | 6-[(3,3-dimethyl-2H-benzofuran-4-yl)oxy]pyridin-3-amine (Intermediate 6) | 2-chloro-3-nitro-pyridine | LC/MS: QC_3_MIN: Rt = 2.66 min; m/z 379 [M + H]+. |
| 27 | 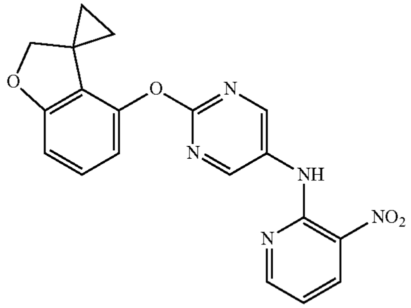 [SMILES: O=[N+]([O-])c1cccnc1Nc1cnc(Oc2cccc3c2C2(CC2)CO3)nc1] | N-(3-nitropyridin-2-yl)-2-{2H-spiro[1-benzofuran-3,1'-cyclopropane]oxy}pyrimidin-5-amine | 2-{2H-spiro[1-benzofuran-3,1'-cyclopropane]oxy}pyrimidin-5-amine (Intermediate 7) | 2-chloro-3-nitropyridine | LC/MS: QC_3_MIN: Rt = 2.40 min; m/z 378 [M + H]+. |

-continued

| Int. | Structure | Name | Aniline | Nitro derivative | LC-MS |
|---|---|---|---|---|---|
| 28 | 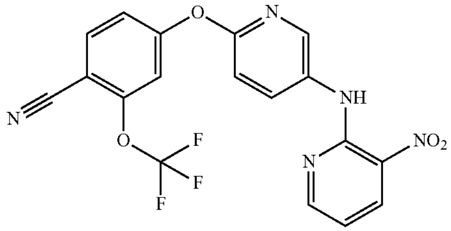 [SMILES: N#Cc1ccc(Oc2ccc(Nc3ncccc3[N+](=O)[O-])cn2)cc1OC(F)(F)F] | 4-[5-[(3-nitro-2-pyridyl)amino]-2-pyridyl]oxy]-2-(trifluoromethoxy) benzonitrile | 4-[(5-amino-2-pyridyl)oxy]-2-(trifluoromethoxy) benzonitrile (WO2011/069951 Intermediate 161) | 2-chloro-3-nitro-pyridine | LC/MS: QC_3_MIN: Rt = 2.56 min; m/z 418 [M + H]+. |
| 29 | 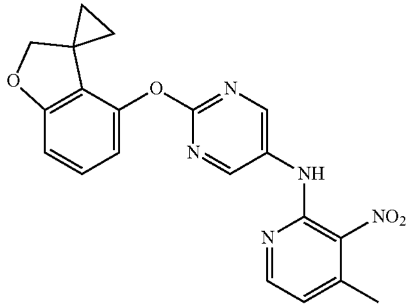 [SMILES: Cc1ccnc(Nc2cnc(Oc3cccc4c3C3(CC3)CO4)nc2)c1[N+](=O)[O-]] | N-(4-methyl-3-nitro-2-pyridyl)-2-spiro[2H-benzofuran-3,1'-cyclopropane]-4-yloxy-pyrimidin-5-amine | 2-spiro [2H-benzofuran-3,1'-cyclopropane]-4-yloxypyrimidin-5-amine (Intermediate 7) | 2-chloro-4-methyl-3-nitro-pyridine | LC/MS: QC_3_MIN: Rt = 2.46 min; m/z 392 [M + H]+. |
| 30 | 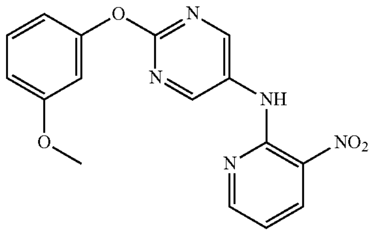 [SMILES: COc1cccc(Oc2ncc(Nc3ncccc3[N+](=O)[O-])cn2)c1] | 2-(3-methoxyphenoxy)-N-(3-nitro-2-pyridyl)pyrimidin-5-amine | 2-(3-methoxyphenoxy) pyrimidin-5-amine (Intermediate 8) | 2-chloro-3-nitro-pyridine | LC/MS: QC_3_MIN: Rt = 2.31 min; m/z 340 [M + H]+. |
| 31 | 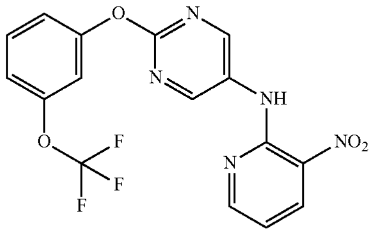 [SMILES: O=[N+]([O-])c1cccnc1Nc1cnc(Oc2cccc(OC(F)(F)F)c2)nc1] | N-(3-nitro-2-pyridyl)-2-[3-(trifluoromethoxy) phenoxy] pyrimidin-5-amine | 6-[3-(trifluoromethoxy) phenoxy]pyrimidin-3-amine (Intermediate 10) | 2-chloro-3-nitro-pyridine | LC/MS: QC_3_MIN: Rt = 2.61 min m/z 394 [M + H]+ |

Intermediate 32

N2-[6-(7-methylspiro[2H-benzofuran-3,1'-cyclopropane]-4-yl)oxy-3-pyridyl]pyridine-2,3-diamine

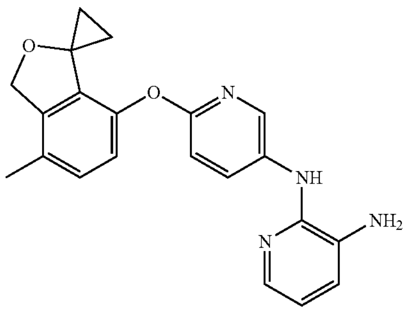

Iron (59 mg, 1.05 mmol), ammonium chloride (56 mg, 1.05 mmol) and N-[6-(7-methylspiro[2H-benzofuran-3,1'-cyclopropane]-4-yl)oxy-3-pyridyl]-3-nitro-pyridin-2-amine (Intermediate 15, 82 mg, 0.21 mmol) were suspended in a mixture ethanol (4 mL)/water (1 mL). The mixture was refluxed at 80° C. for 1 h. After cooling, the solids were filtered off and the filtrate was diluted with EtOAc (30 mL) and washed with brine (30 mL). The residue was purified by flash chromatography (Biotage System) on silica gel using a SFAR 10 g as column and Cyclohexane/Ethyl acetate from 80:20 to 30:70 as eluent, affording the title compound N2-[6-(7-methylspiro[2H-benzofuran-3,1'-cyclopropane]-4-yl)oxy-3-pyridyl]pyridine-2,3-diamine (42 mg) as a white solid.

LC/MS: QC_3_MIN: Rt=2.01 min m/z 361 [M+H]+

The following compounds were prepared using analogous methods to the foregoing methodology, replacing N-[6-(7-methylspiro[2H-benzofuran-3,1'-cyclopropane]-4-yl)oxy-3-pyridyl]-3-nitro-pyridin-2-amine (Intermediate 15) with the appropriate nitro derivative. The reactions were performed with temperatures ranging from room temperature (rt) to 80° C. The conditions for each case are specified in the table. Final products were purified by flash-chromatography (Silica cartridge; Cyclohexane/EtOAc or other appropriate solvent system) and/or reverse chromatography (C-18 cartridge; water/acetonitrile or other appropriate solvent system).

| Int | Structure | Name | Nitro derivative | T (°C) / h | LC-MS |
|---|---|---|---|---|---|
| 33 | 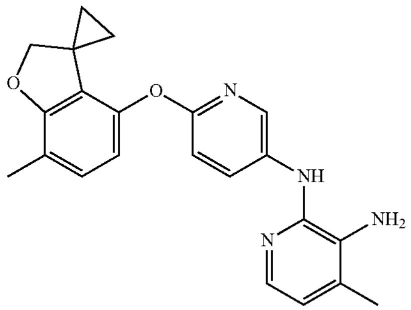 | 4-methyl-N2-[6-(7-methylspiro[2H-benzofuran-3,1'-cyclopropane]-4-yl)oxy-3-pyridyl]pyridine-2,3-diamine | 4-methyl-N-[6-(7-methylspiro[2H-benzofuran-3,1'-cyclopropane]-4-yl)oxy-3-pyridyl]-3-nitro-pyridin-2-amine (Intermediate 16) | 80° C. for 1 h | LC/MS: QC_3_MIN: Rt = 2.06 min [M + H]+ = 375 |
| 34 | 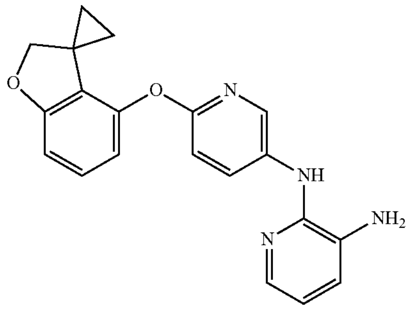 [SMILES: Nc1cccnc1Nc1ccc(Oc2cccc3c2C2(CC2)CO3)nc1] | N2-(6-spiro[2H-benzofuran-3,1'-cyclopropane]-4-yloxy-3-pyridyl)pyridine-2,3-diamine | 3-nitro-N-(6-spiro[2H-benzofuran-3,1'-cyclopropane]-4-yloxy-3-pyridyl)pyridin-2-amine (Intermediate 17) | 80° C. for 1 h | LC/MS: QC_3_MIN: Rt = 1.89 min [M + H]+ = 347 |
| 35 | 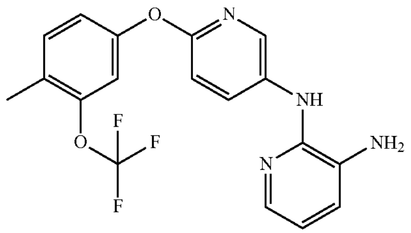 [SMILES: Cc1ccc(Oc2ccc(Nc3ncccc3N)cn2)cc1OC(F)(F)F] | N2-[6-[4-methyl-3-(trifluoromethoxy)phenoxy]-3-pyridyl]pyridine-2,3-diamine | N-[6-[4-methyl-3-(trifluoromethoxy)phenoxy]-3-pyridyl]-3-nitro-pyridin-2-amine (Intermediate 18) | 80° C. for 1 h | LC/MS: QC_3_MIN: Rt = 2.11 min [M + H]+ = 377 |

-continued

| Int | Structure | Name | Nitro derivative | T (°C) / h | LC-MS |
|---|---|---|---|---|---|
| 36 | 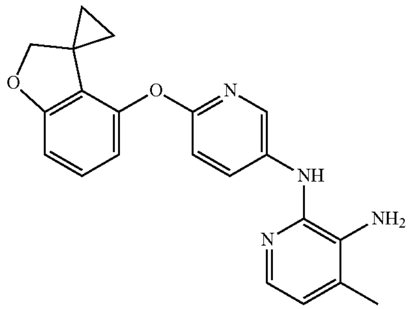 [SMILES: Cc1ccnc(Nc2ccc(Oc3cccc4c3C3(CC3)CO4)nc2)c1N] | 4-methyl-N2-(6-spiro[2H-benzofuran-3,1'-cyclopropane]-4-yloxy-3-pyridyl)pyridine-2,3-diamine | 4-methyl-3-nitro-N-(6-spiro[2H-benzofuran-3,1'-cyclopropane]-4-yloxy-3-pyridyl)pyridin-2-amine (Intermediate 19) | 80° C. for 1 h | LC/MS: QC_3_MIN: Rt = 1.95 min [M + H]+ = 361 |
| 37 | 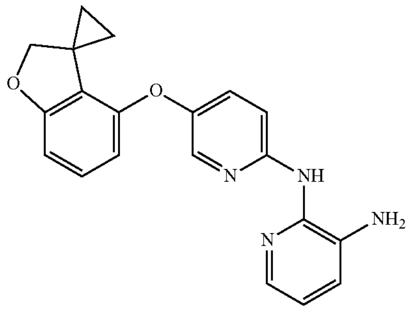 | N2-(5-spiro[2H-benzofuran-3,1'-cyclopropane]-4-yloxy-2-pyridyl)pyridine-2,3-diamine | 3-nitro-N-(5-spiro[2H-benzofuran-3,1'-cyclopropane]-4-yloxy-2-pyridyl)pyridin-2-amine (Intermediate 20) | 80° C. for 2 h | LC/MS: QC_3_MIN: Rt = 2.13 min [M + H]+ = 347 |
| 38 | 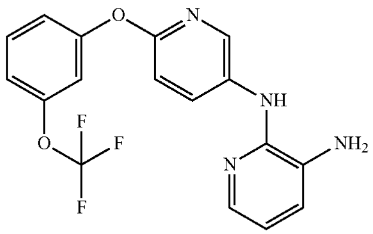 | N2-[6-[3-(trifluoromethoxy) phenoxy]-3-pyridyl]pyridine-2,3-diamine | 3-nitro-N-[6-[3-(trifluoromethoxy) phenoxy]-3-pyridyl]pyridin-2-amine (Intermediate 21) | 80° C. for 1 h | LC/MS: QC_3_MIN: Rt = 1.99 [M + H]+ = 363 |

-continued

| Int | Structure | Name | Nitro derivative | T (°C) / h | LC-MS |
|---|---|---|---|---|---|
| 39 | 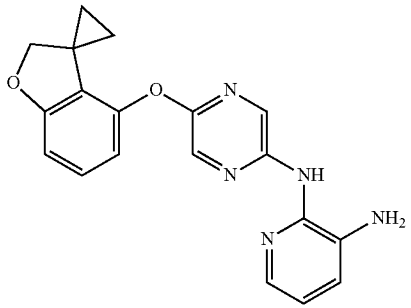 | N2-(5-spiro[2H-benzofuran-3,1'-cyclopropane]-4-yloxypyrazin-2-yl)pyridine-2,3-diamine | N-(3-nitro-2-pyridyl)-5-spiro[2H-benzofuran-3,1'-cyclopropane]-4-yloxy-pyrazin-2-amine (Intermediate 22) | rt for 18 h | LC/MS: QC_3_MIN: Rt = 1.98 min [M + H]+ = 348 |
| 40 | 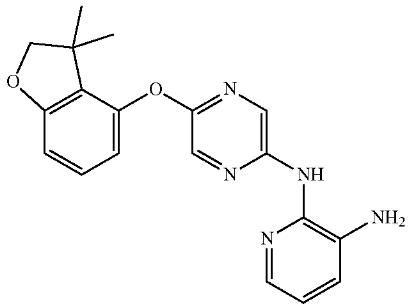 | N2-[5-[(3,3-dimethyl-2H-benzofuran-4-yl)oxy]pyrazin-2-yl]pyridine-2,3-diamine | 5-[(3,3-dimethyl-2H-benzofuran-4-yl)oxy]-N-(3-nitro-2-pyridyl)pyrazin-2-amine (Intermediate 23) | rt for 18 h | LC/MS: QC_3_MIN: Rt = 2.05 min [M + H]+ = 350 |
| 41 | 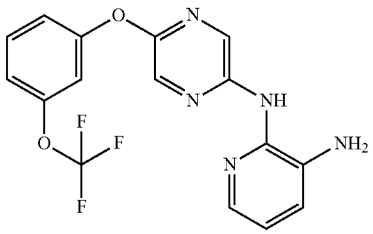 [SMILES: Nc1cccnc1Nc1cnc(Oc2cccc(OC(F)(F)F)c2)cn1] | N2-[5-[3-(trifluoromethoxy)phenoxy]pyrazin-2-yl]pyridine-2,3-diamine | N-(3-nitro-2-pyridyl)-5-[3-(trifluoromethoxy)phenoxy]pyrazin-2-amine (Intermediate 24) | rt for 18 h | LC/MS: QC_3_MIN: Rt = 2.10 min [M + H]+ = 364 |

-continued

| Int | Structure | Name | Nitro derivative | T (°C) / h | LC-MS |
|---|---|---|---|---|---|
| 42 | 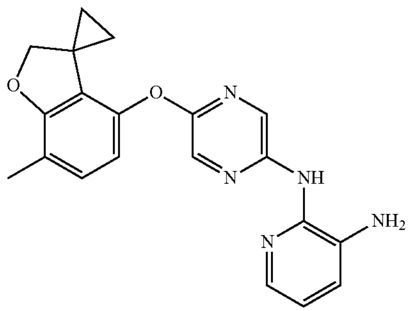 [SMILES: Cc1ccc(Oc2cnc(Nc3ncccc3N)cn2)c2c1OCC21CC1] | N2-[5-(7-methylspiro[2H-benzofuran-3,1'-cyclopropane]-4-yl)oxypyrazin-2-yl]pyridine-2,3-diamine | 5-(7-methylspiro[2H-benzofuran-3,1'-cyclopropane]-4-yl)oxy-N-(3-nitro-2-pyridyl)pyrazin-2-amine (Intermediate 25) | rt for 18 h | LC/MS: QC_3_MIN: Rt = 2.10 min [M + H]+ = 362 |
| 43 | 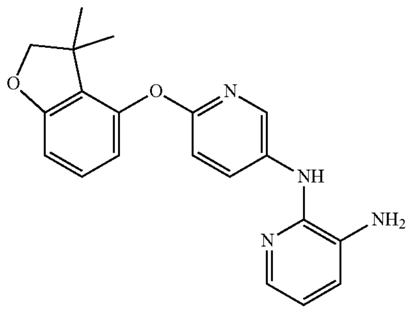 | N2-[6-[(3,3-dimethyl-2H-benzofuran-4-yl)oxy]-3-pyridyl]pyridine-2,3-diamine | N-[6-[(3,3-dimethyl-2H-benzofuran-4-yl)oxy]-3-pyridyl]-3-nitro-pyridin-2-amine (Intermediate 26) | 80° C. for 1 h | LC/MS: QC_3_MIN: Rt = 1.94 min [M + H]+ = 349 |
| 44 | 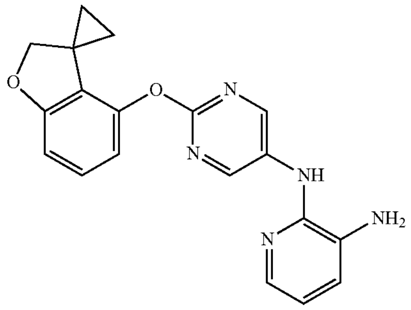 | N2-(2-spiro[2H-benzofuran-3,1'-cyclopropane]-4-yloxypyrimidin-5-yl)pyridine-2,3-diamine | N-(3-nitropyridin-2-yl)-2-{2H-spiro[1-benzofuran-3,1'-cyclopropane]oxy}pyrimidin-5-amine (Intermediate 27) | rt overnight | LC/MS: QC_3_MIN: Rt = 1.74 min [M + H]+ = 348 |

-continued

| Int | Structure | Name | Nitro derivative | T (°C) / h | LC-MS |
|---|---|---|---|---|---|
| 45 | 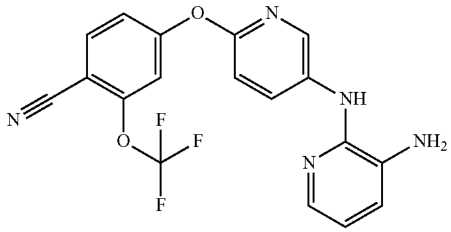 [SMILES: N#Cc1ccc(Oc2ccc(Nc3ncccc3N)cn2)cc1OC(F)(F)F] | 4-[[5-[(3-amino-2-pyridyl)amino]-2-pyridyl]oxy]-2-(trifluoromethoxy) benzonitrile | 4-[5-[(3-nitro-2-pyridyl)amino]-2-pyridyl]oxy]-2-(trifluoromethoxy) benzonitrile (Intermediate 28) | 80° C. for 1 h | LC/MS: QC_3_MIN: Rt = 1.97 min [M + H]+ = 388 |
| 46 | 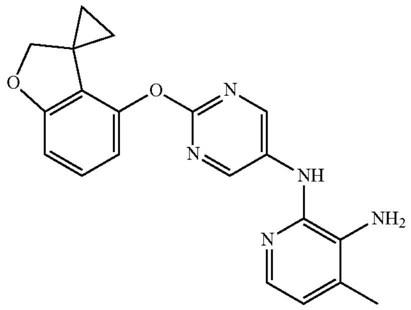 [SMILES: Cc1ccnc(Nc2cnc(Oc3cccc4c3C3(CC3)CO4)nc2)c1N] | 4-methyl-N2-(2-spiro [2H-benzofuran-3,1'-cyclopropane]-4-yloxypyrimidin-5-yl)pyridine-2,3-diamine | N-(4-methyl-3-nitro-2-pyridyl)-2-spiro[2H-benzofuran-3,1'-cyclopropane]-4-yloxy-pyrimidin-5-amine (Intermediate 29) | rt for 18 h | LC/MS: QC_3_MIN: Rt = 1.84 min [M + H]+ = 362 |
| 47 | 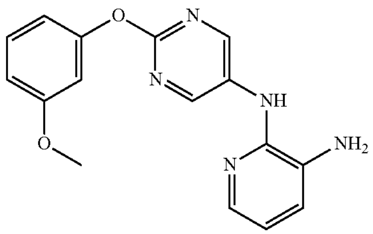 | N2-[2-(3-methoxyphenoxy) pyrimidin-5-yl]pyridine-2,3-diamine | 2-(3-methoxyphenoxy)-N-(3-nitro-2-pyridyl)pyrimidin-5-amine (Intermediate 30) | rt for 16h, then 50° C. for 1 h and then 60° C. for 1 h | LC/MS: QC_3_MIN: Rt = 1.70 min [M + H]+ = 310 |
| 48 | 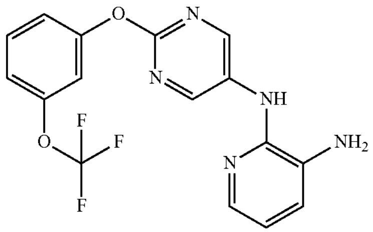 [SMILES: Nc1cccnc1Nc1cnc(Oc2cccc(OC(F)(F)F)c2)nc1] | N2-[2-(3-trifluoromethoxy phenoxy)pyrimidin-5-yl]pyridine-2,3-diamine | N-(3-nitro-2-pyridyl)-2-[3-(trifluoromethoxy) phenoxy]pyrimidin-5-amine (Intermediate 31) | rt for 16 h | LC/MS: QC_3_MIN: Rt = 2.36 min [M + H]+ = 364 |

Intermediate 49

1-(4-chloro-2-methyl-pyrimidin-5-yl)-3-[6-[3-(trifluoromethoxy)phenoxy]-3-pyridyl]urea

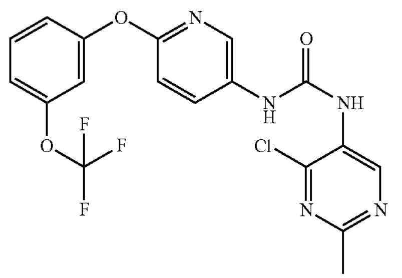 [SMILES: Cc1ncc(NC(=O)Nc2ccc(Oc3cccc(OC(F)(F)F)c3)nc2)c(Cl)n1]

Method 1:

A mixture of bis(trichloromethyl) carbonate (90 mg, 0.3033 mmol) in dichloromethane (2 mL) was cooled to 0° C. A solution of 6-[3-(trifluoromethoxy)phenoxy]pyridin-3-amine (intermediate 9, 200 mg, 0.7402 mmol) and N,N-diisopropylethylamine (371 mg, 2.8706 mmol) (0.50 mL) in dichloromethane (3 mL) was then added dropwise and the reaction mixture was left to stir at 0° C. for 30 minutes. Vacuum was applied for several minutes to remove excess phosgene and then a solution of 4-(dimethylamino)pyridine (100 mg, 0.8185 mmol) in dichloromethane (1 mL) was added dropwise and the reaction mixture was left to stir at 0° C. for 5 minutes. 4-chloro-2-methyl-pyrimidin-5-amine (115 mg, 0.8010 mmol) was added and the reaction mixture was left to stir at 0° C. for 1 hour. The reaction mixture was diluted with DCM (15 mL) and washed with a 0.4 M aqueous solution of HCl (10 mL) and brine (15 mL). The organic layer was separated, dried over $Na_2SO_4$, filtered and concentrated under vacuum. The crude material was then purified by Reverse Phase flash chromatography (Biotage System) on silica gel using a SNAP C-18 12 g column eluting Water:Acetonitrile from 95:5 to 5:95. The desired fractions were collected and concentrated under vacuum to afford the title compound 1-(4-chloro-2-methyl-pyrimidin-5-yl)-3-[6-[3-(trifluoromethoxy)phenoxy]-3-pyridyl]urea (74 mg) as a white solid.

LC/MS: QC_3_MIN: Rt=2.42 min; m/z 440 & 442 [M+H]+.

The following compounds were prepared using analogous methods to the foregoing methodology, replacing 6-[3-(trifluoromethoxy)phenoxy]pyridin-3-amine (intermediate 9) with the appropriate amine intermediate. Final products were purified by flash-chromatography (Silica cartridge; Cyclohexane/EtOAc or other appropriate solvent system) and/or reverse chromatography (C-18 cartridge; water/acetonitrile or other appropriate solvent system).

| Int. | Structure | Name | Amine intermediate | LCMS |
|---|---|---|---|---|
| 50 | 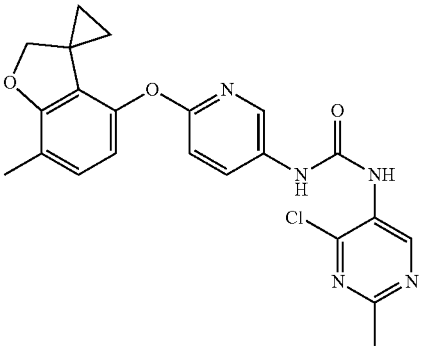 [SMILES: Cc1ncc(NC(=O)Nc2ccc(Oc3ccc(C)c4c3C3(CC3)CO4)nc2)c(Cl)n1] | 1-(4-chloro-2-methyl-pyrimidin-5-yl)-3-[6-(7-methylspiro[2H-benzofuran-3,1'-cyclopropane]-4-yl)oxy-3-pyridyl]urea | 6-(7-methylspiro[2H-benzofuran-3,1'-cyclopropane]-4-yl)oxypyridin-3-amine (WO2012/076877 Intermediate 158) | LC/MS: QC_3_MIN: Rt = 2.22 min; m/z 438, 440 [M + H]+. |
| 51 | 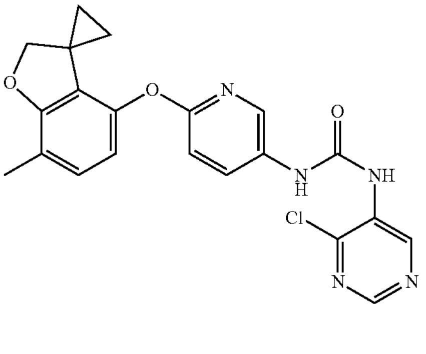 [SMILES: Cc1ccc(Oc2ccc(NC(=O)Nc3cncnc3Cl)cn2)c2c1OCC21CC1] | 1-(4-chloropyrimidin-5-yl)-3-[6-(7-methylspiro[2H-benzofuran-3,1'-cyclopropane]-4-yl)oxy-3-pyridyl]urea | 6-(7-methylspiro[2H-benzofuran-3,1'-cyclopropane]-4-yl)oxypyridin-3-amine (WO2012/076877 Intermediate 158) | LC/MS: QC_3_MIN: Rt = 2.48 min; m/z 424 & 426 [M + H]+. |

-continued

| Int. | Structure | Name | Amine intermediate | LCMS |
|---|---|---|---|---|
| 52 | 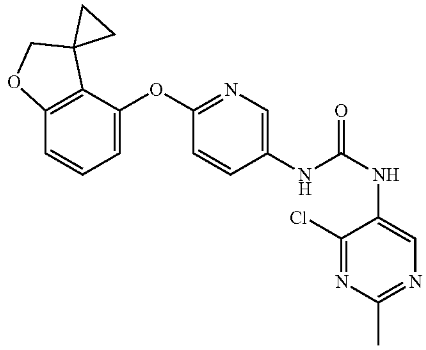 [SMILES: Cc1ncc(NC(=O)Nc2ccc(Oc3cccc4c3C3(CC3)CO4)nc2)c(Cl)n1] | 1-(4-chloro-2-methyl-pyrimidin-5-yl)-3-(6-spiro[2H-benzofuran-3,1'-cyclopropane]-4-yloxy-3-pyridyl)urea | 6-spiro[2H-benzofuran-3,1'-cyclopropane]-4-yloxypyridin-3-amine (WO2012/076877 Intermediate 87) | LC/MS: QC_3_MIN: Rt = 2.10 min; m/z 424 & 426 [M + H]+. |
| 53 | 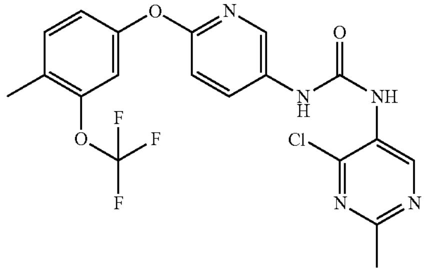 [SMILES: Cc1ncc(NC(=O)Nc2ccc(Oc3ccc(C)c(OC(F)(F)F)c3)nc2)c(Cl)n1] | 1-(4-chloro-2-methyl-pyrimidin-5-yl)-3-[6-[4-methyl-3-(trifluoromethoxy) phenoxy]-3-pyridyl] urea | 6-[4-methyl-3-(trifluoromethoxy) phenoxy]pyridin-3-amine (WO2011/069951 Intermediate 147) | LC/MS: QC_3_MIN: Rt = 2.53 min; m/z 454 & 456 [M + H]+. |
| 54 | 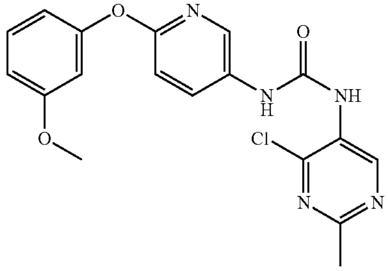 | 1-(4-chloro-2-methyl-pyrimidin-5-yl)-3-[6-(3-methoxyphenoxy)-3-pyridyl]urea | 6-[3-(trifluoromethoxy) phenoxy]pyridin-3-amine | LC/MS: QC_3_MIN: Rt = 2.53 min; m/z 440 & 442 [M + H]+. |

Intermediate 49

1-(4-chloro-2-methyl-pyrimidin-5-yl)-3-[6-[3-(trifluoromethoxy)phenoxy]-3-pyridyl]urea

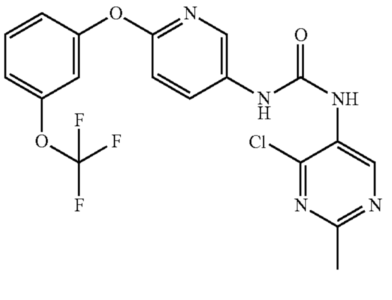 [SMILES: Cc1ncc(NC(=O)Nc2ccc(Oc3cccc(OC(F)(F)F)c3)nc2)c(Cl)n1]

Method 2:

A mixture of bis(trichloromethyl) carbonate (58 mg, 0.1955 mmol) in ethyl acetate (3 mL) was cooled to 0° C. A solution of 6-[3-(trifluoromethoxy)phenoxy]pyridin-3-amine (Intermediate 9, 105 mg, 0.3886 mmol) and N,N-diisopropylethylamine (148.4 mg, 1.1483 mmol) (0.2 mL) in ethyl acetate (3 mL) was added dropwise and the reaction mixture was left to stir at 0° C. for 15 minutes. Vacuum was applied for several minutes to remove excess phosgene and then 4-(dimethylamino)pyridine (48 mg, 0.3929 mmol) in ethyl acetate (0.5 mL) and dichloromethane (0.5 mL) was added and stirred at 0° C. for 5 minutes. 4-chloro-2-methyl-pyrimidin-5-amine (62 mg, 0.4318 mmol) was added and the reaction mixture was left to stir at room temperature for 1 hour. The reaction mixture was then quenched with 0.2 N HCl (20 mL) and extracted with ethyl acetate (20 mL). The organic layer was dried over $Na_2SO_4$, filtered then concentrated in vacuo. The residue was purified using Flash column chromatography (Biotage system) using a MODUS 12 g column and cyclohexane:ethyl acetate from 90:10 to 50:50 as eluent, followed by reverse phase chromatography using a C-18 12 g column and water:acetonitrile from 95:5 to 15:85 as eluent to afford the title compound 1-(4-chloro-2-methyl-pyrimidin-5-yl)-3-[6-[3-(trifluoromethoxy)phenoxy]-3-pyridyl]urea (25 mg) as a white solid.

LC/MS: QC_3_MIN: Rt=2.53 min; m/z 440 & 442 [M+H]+.

The following compounds were prepared using analogous methods to the foregoing methodology, replacing 6-[3-(trifluoromethoxy)phenoxy]pyridin-3-amine (Intermediate 9) with the appropriate amine intermediate. Final products were purified by flash-chromatography (Silica cartridge; Cyclohexane/EtOAc or other appropriate solvent system) and/or reverse chromatography (C-18 cartridge; water/acetonitrile or other appropriate solvent system).

| Int. | Structure | Name | Amine intermediate | LCMS |
|---|---|---|---|---|
| 52 | 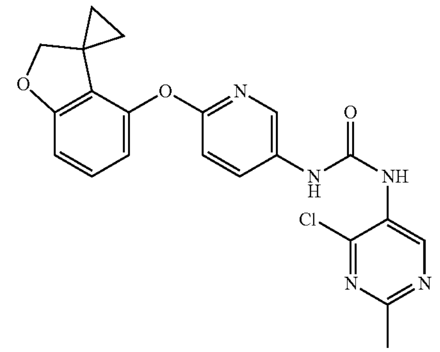 [SMILES: Cc1ncc(NC(=O)Nc2ccc(Oc3cccc4c3C3(CC3)CO4)nc2)c(Cl)n1] | 1-(4-chloro-2-methyl-pyrimidin-5-yl)-3-(6-spiro[2H-benzofuran-3,1'-cyclopropane]-4-yloxy-3-pyridyl)urea | 6-spiro[2H-benzofuran-3,1'-cyclopropane]-4-yloxypyridin-3-amine (WO2012/076877 Intermediate 87) | LC/MS: QC_3_MIN: Rt = 2.37 min; m/z 424 & 426 [M + H]+. |

Intermediate 55

1-(4-chloro-2-methyl-pyrimidin-5-yl)-3-(6-fluoro-3-pyridyl)urea

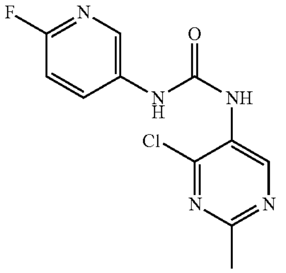 [SMILES: Cc1ncc(NC(=O)Nc2ccc(F)nc2)c(Cl)n1]

A mixture of bis(trichloromethyl) carbonate (260 mg, 0.8762 mmol) in dichloromethane (4 mL) was cooled to 0° C. A solution of 5-amino-2-fluoropyridine (190 mg, 1.6948 mmol) and N,N-diisopropylethylamine (742 mg, 5.7413 mmol) (1 mL) in dichloromethane (4 mL) was added dropwise and the reaction mixture was left to stir at 0° C. for 15 minutes. Vacuum was applied for several minutes to remove excess phosgene and then 4-(dimethylamino)pyridine (214 mg, 1.7517 mmol) in dichloromethane (1 mL) was added and stirred at 0° C. for 5 minutes. 4-chloro-2-methyl-pyrimidin-5-amine (242 mg, 1.68 mmol) in dichloromethane (2 mL) was added portionwise and the reaction mixture was left to stir at room temperature for 1.5 hours. The reaction mixture was then quenched with 0.2 N HCl (20 mL) and extracted with ethyl acetate (20 mL). The organic layer was dried over $Na_2SO_4$, filtered then concentrated in vacuo. The residue was purified reverse phase chromatography using a C-18 12 g column and water: acetonitrile from 95:5 to 60:40 as eluent to afford the title compound (isolated in two batches) 1-(4-chloro-2-methyl-pyrimidin-5-yl)-3-(6-fluoro-3-pyridyl)urea (94 mg) as a yellow solid and 1-(4-chloro-2-methyl-pyrimidin-5-yl)-3-(6-fluoro-3-pyridyl)urea (180 mg) as a white solid.

LC/MS: QC_3_MIN: Rt=1.83 min; m/z 281 & 283 [M+H]+

Intermediate 56

9-(6-fluoro-3-pyridyl)-2-methyl-7H-purin-8-one

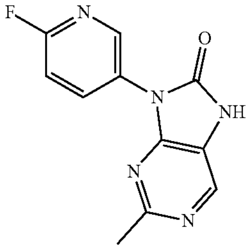 [SMILES: Cc1ncc2[nH]c(=O)n(-c3ccc(F)nc3)c2n1]

A mixture of 1-(4-chloro-2-methyl-pyrimidin-5-yl)-3-(6-fluoro-3-pyridyl)urea (Intermediate 55, 94 mg, 0.3337 mmol), cesium carbonate (215 mg, 0.66 mmol), (5-diphenylphosphanyl-9,9-dimethyl-xanthen-4-yl)-diphenyl-phosphane (Xantphos) (22 mg, 0.038 mmol), and diacetoxypalladium (palladium(II) acetate) (7 mg, 0.0312 mmol) in 1,4-dioxane (5 mL) was put under a vacuum-nitrogen flush and stirred at 95° C. for 2 hours. The reaction was filtered and concentrated in vacuo then purified by reverse phase chromatography (Biotage system) using a C-18 25 g column and water:acetonitrile from 95:5 to 80:20 as eluent to afford the title compound 9-(6-fluoro-3-pyridyl)-2-methyl-7H-purin-8-one (12 mg) as a white solid.

LC/MS: QC_3_MIN: Rt=1.45 min; m/z 245 [M]

Intermediate 57

4-bromo-1-[(4-methoxyphenyl)methyl]-3-nitro-pyrazole

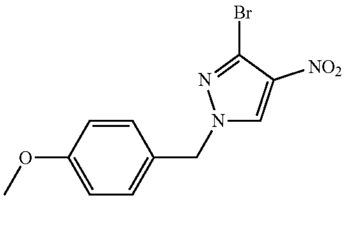 [SMILES: COc1ccc(Cn2cc([N+](=O)[O-])c(Br)n2)cc1]

4-bromo-3-nitro-1H-pyrazole (135 mg, 0.70 mmol) was dissolved in N,N-dimethylformamide (2 mL). sodium hydride 60% dispersion in mineral oil (34 mg, 0.84 mmol) and 1-(bromomethyl)-4-methoxy-benzene (156 mg, 0.77 mmol) were added. The reaction mixture was stirred at rt for 2 h. The reaction was quenched with water (15 mL) and diluted with ethyl acetate (20 mL). The two phases were separated and the organic one washed with brine (20 mL), dried over sodium sulfate and evaporated to dryness. The residue was purified by flash chromatography (Biotage System) on silica gel using a SFAR 5 g as column and cyclohexane/ethyl acetate from 100:0 to 70:30 as eluent, affording the title compound 4-bromo-1-[(4-methoxyphenyl)methyl]-3-nitro-pyrazole (197 mg) as a yellow oil.

LC/MS: QC_3_MIN: Rt=2.30 min; m/z

Intermediate 58

N-(1-methyl-4-nitro-pyrazol-3-yl)-6-spiro[2H-benzofuran-3,1'-cyclopropane]-4-yloxy-pyridin-3-amine

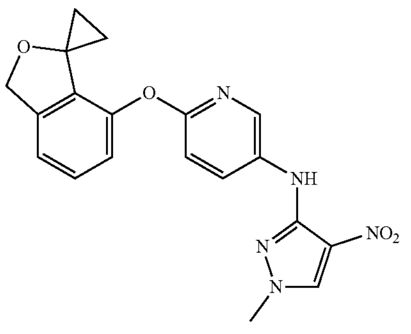

6-spiro[2H-benzofuran-3,1'-cyclopropane]-4-yloxypyridin-3-amine (WO2012/076877 Intermediate 87, 394 mg, 1.55 mmol), cesium carbonate (1.01 g, 3.09 mmol), 3-chloro-1-methyl-4-nitropyrazole (250 mg, 1.55 mmol) were dissolved in 1,4-dioxane (5 mL), Xantphos (67 mg, 0.12 mmol) and $Pd(OAc)_2$ (17 mg, 0.08 mmol) were added. Three times cycle Argon-vacuum was applied and the mixture was stirred at 110° C. for 7 h. Then, further Xanthphos (35 mg) and $Pd(OAc)_2$ (10 mg) were added and the reaction mixture was stirred at 110 C for further 2 h. The reaction was quenched with $NH_4Cl$ (50 ml) and EtOAc (50 ml) was added. the two layers were shaken, separated and the organic one was collected, washed with Brine (50 ml), dried with $Na_2SO_4$, filtered and evaporated. The crude was suspended in MTBE (10 Volumes), and the mixture was stirred 1 h at 50° C. and 3 h at RT. The solid was filtered under vacuum affording N-(1-methyl-4-nitro-pyrazol-3-yl)-6-spiro[2H-benzofuran-3,1'-cyclopropane]-4-yloxy-pyridin-3-amine (1 g) as brown solid used in the next step without further purification.

LC/MS: QC_3_MIN: Rt=2.49 min; m/z 380 [M+H]+.

The following compounds were prepared using analogous methods to the foregoing methodology, replacing 6-spiro[2H-benzofuran-3,1'-cyclopropane]-4-yloxypyridin-3-amine (WO2012/076877 Intermediate 87) with the appropriate amine intermediate. Products were either isolated crude or were purified by flash-chromatography (Silica cartridge; Cyclohexane/EtOAc or other appropriate solvent system) and/or reverse chromatography (C-18 cartridge; water/acetonitrile or other appropriate solvent system).

| Int. | Structure | Name | Amine intermediate | LCMS |
|---|---|---|---|---|
| 59 | 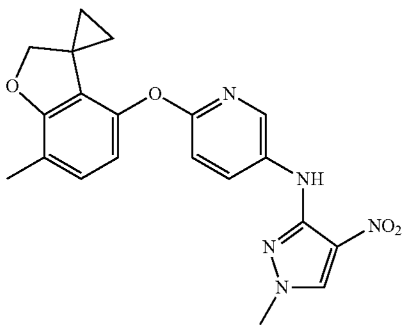 | N-(1-methyl-4-nitro-pyrazol-3-yl)-6-(7-methylspiro[2H-benzofuran-3,1'-cyclopropane]-4-yl)oxy-pyridin-3-amine | 6-(7-methylspiro[2H-benzofuran-3,1'-cyclopropane]-4-yl)oxypyridin-3-amine (WO2012/076877 Intermediate 158). | LC/MS: QC_3_MIN: Rt = 2.54 min; m/z 394 [M + H]+, 809 [2M + Na]+ |
| 60 | 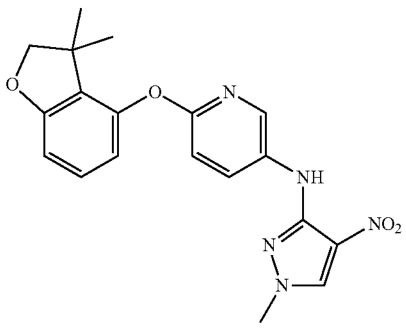 | 6-[(3,3-dimethyl-2H-benzofuran-4-yl)oxy]-N-(1-methyl-4-nitropyrazol-3-yl)pyridin-3-amine | 6-[(3,3-dimethyl-2H-benzofuran-4-yl)oxy]pyridin-3-amine (Intermediate 6) | LC/MS: QC_3_MIN: Rt = 2.49 min; m/z 382 [M + H]+ |

-continued

| Int. | Structure | Name | Amine intermediate | LCMS |
|---|---|---|---|---|
| 61 | 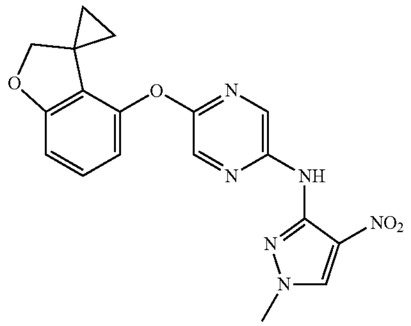 | N-(1-methyl-4-nitro-pyrazol-3-yl)-5-spiro[2H-benzofuran-3,1'-cyclopropane]-4-yloxypyrazin-2-amine | 5-spiro[2H-benzofuran-3,1'-cyclopropane]-4-yloxypyrazin-2-amine (Intermediate 11) | LC/MS: QC_3_MIN: Rt = 2.55 min; m/z 381 [M + H]+ |
| 62 | 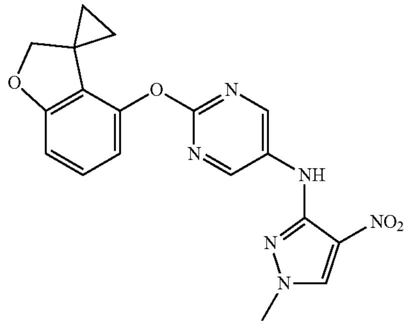 | N-(1-methyl-4-nitro-pyrazol-3-yl)-2-spiro[2H-benzofuran-3,1'-cyclopropane]-4-yloxy-pyrimidin-5-amine | N-(4-methyl-3-nitro-2-pyridyl)-2-spiro[2H-benzofuran-3,1'-cyclopropane]-4-yloxy-pyrimidin-5-amine (Intermediate 29) | LC/MS: QC_3_MIN: Rt = 2.36 min; m/z 381 [M + H]+, 783 [2M + Na]+ |

Intermediate 63

N-[1-[(4-methoxyphenyl)methyl]-4-nitro-pyrazol-3-yl]-6-spiro[2H-benzofuran-3,1'-cyclopropane]-4-yloxy-pyridin-3-amine

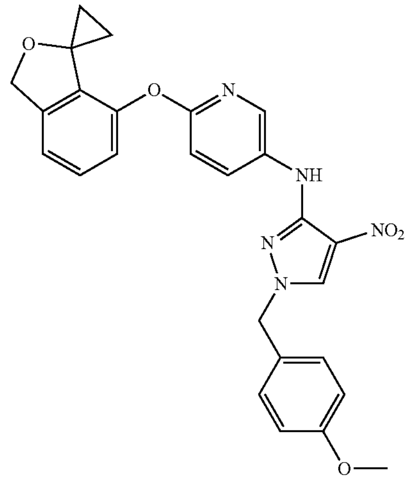

Intermediate 59 was prepared using the same methodology described for the synthesis of Intermediate 55 replacing 3-chloro-1-methyl-4-nitropyrazole with 4-bromo-1-[(4-methoxyphenyl)methyl]-3-nitro-pyrazole (intermediate 57).

LC/MS: QC_3_MIN: Rt=2.71 min; m/z 486 [M+H]+.

Intermediate 64

1-methyl-N3-(6-spiro[2H-benzofuran-3,1'-cyclopropane]-4-yloxy-3-pyridyl)pyrazole-3,4-diamine

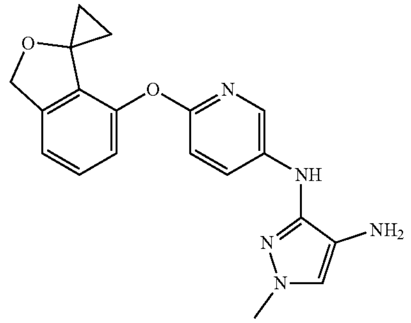 [SMILES: Cn1cc([N+](=O)[O-])c(Nc2ccc(Oc3cccc4c3C3(CC3)OC4)nc2)n1]

Iron (74 mg, 1.32 mmol), ammonium chloride (70 mg, 1.32 mmol) and N-(1-methyl-4-nitro-pyrazol-3-yl)-6-spiro[2H-benzofuran-3,1'-cyclopropane]-4-yloxy-pyridin-3-amine (Intermediate 58, 100 mg, 0.26 mmol) were suspended on a mixture ethanol (2 mL) water (0,5000 mL). The mixture was refluxed at 80° C. for 1 h. After cooling, the solids were filtered and the mixture was diluted with EtOAc (30 mL) and washed with brine (50 mL). The residue was purified by flash chromatography (Biotage System) on silica gel using a SFAR 10 g as column and DCM/MeOH from 99/1: to 90/10 as eluent, affording the title compound 1-methyl-N3-(6-spiro[2H-benzofuran-3,1'-cyclopropane]-4-yloxy-3-pyridyl)pyrazole-3,4-diamine (40 mg) as a white solid. LC/MS: QC_3_MIN: Rt=1.92 min; m/z 350 [M+H]+, 722 [2M+Na]+

The following compounds were prepared using analogous methods to the foregoing methodology, replacing N-(1-methyl-4-nitro-pyrazol-3-yl)-6-spiro[2H-benzofuran-3,1'-cyclopropane]-4-yloxy-pyridin-3-amine (Intermediate 58) with the appropriate nitro derivative intermediate. The reactions were performed with temperatures ranging from room temperature (rt) to 80° C. and reaction times ranging from 1 h to 64 h. The conditions for each case are specified in the table. Final products were purified by flash-chromatography (Silica cartridge; Cyclohexane/EtOAc or other appropriate solvent system) and/or reverse chromatography (C-18 cartridge; water/acetonitrile or other appropriate solvent system).

| Int. | Structure | Name | Nitro derivative intermediate | T (° C.)/h | LCMS |
|---|---|---|---|---|---|
| 65 | 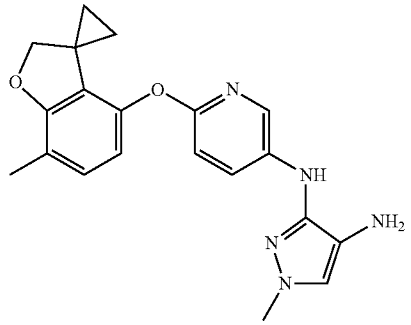 | 1-methyl-N3-[6-(7-methylspiro[2H-benzofuran-3,1'-cyclopropane]-4-yl)oxy-3-pyridyl]pyrazole-3,4-diamine | N-(1-methyl-4-nitro-pyrazol-3-yl)-6-(7-methylspiro[2H-benzofuran-3,1'-cyclopropane]-4-yl)oxy-pyridin-3-amine (Intermediate 59) | 80° C. for 1 h | LC/MS: QC_3_MIN: Rt = 2.00 min; m/z 364 [M + H]+. |
| 66 | 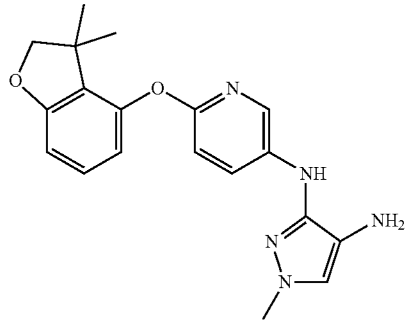 | N3-[6-[(3,3-dimethyl-2H-benzofuran-4-yl)oxy]-3-pyridyl]-1-methyl-pyrazole-3,4-diamine | 6-[(3,3-dimethyl-2H-benzofuran-4-yl)oxy]-N-(1-methyl-4-nitropyrazol-3-yl)pyridin-3-amine (Intermediate 60) | rt for 18 h | LC/MS: QC_3_MIN: Rt = 1.94 min; m/z 352 [M + H]+ |
| 67 | 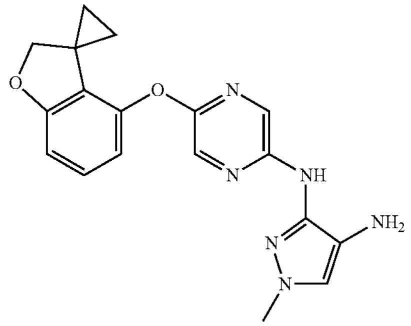 | 1-methyl-N3-(5-spiro[2H-benzofuran-3,1'-cyclopropane]-4-yloxypyrazin-2-yl)pyrazole-3,4-diamine | N-(1-methyl-4-nitro-pyrazol-3-yl)-5-spiro[2H-benzofuran-3,1'-cyclopropane]-4-yloxypyrazin-2-amine (intermediate 61) | rt for 64 h | LC/MS: QC_3_MIN: Rt = 1.86 min; m/z 351 [M + H]+ |
| 68 | 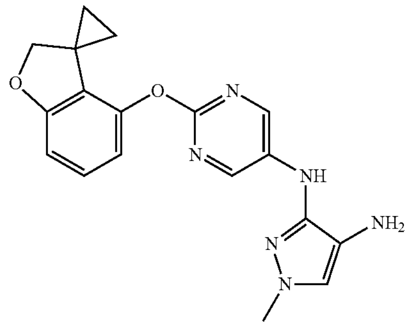 | 1-methyl-N3-(2-spiro[2H-benzofuran-3,1'-cyclopropane]-4-yloxypyrimidin-5-yl)pyrazole-3,4-diamine | N-(1-methyl-4-nitro-pyrazol-3-yl)-2-spiro[2H-benzofuran-3,1'-cyclopropane]-4-yloxy-pyrimidin-5-amine (Intermediate 62) | 50° C. for 4 h | LC/MS: QC_3_MIN: Rt = 1.84 min; m/z 351 [M + H]+, 723 [2M + Na]+ |

-continued

| Int. | Structure | Name | Nitro derivative intermediate | T (° C.)/h | LCMS |
|---|---|---|---|---|---|
| 69 | 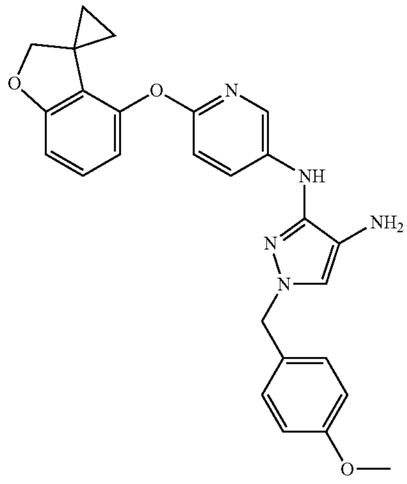 [SMILES: COc1ccc(Cn2cc(N)c(Nc3ccc(Oc4cccc5c4C4(CC4)CO5)nc3)n2)cc1] | 1-[(4-methoxyphenyl) methyl]-N3-(6-spiro[2H-benzofuran-3,1'-cyclopropane]-4-yloxy-3-pyridyl)pyrazole-3,4-diamine | N-[1-[(4-methoxyphenyl) methyl]-4-nitro-pyrazol-3-yl]-6-spiro[2H-benzofuran-3,1'-cyclopropane]-4-yloxy-pyridin-3-amine (Intermediate 63) | rt for 18 h and then 60° C. for 1 h | LC/MS: QC_3_MIN: Rt = 2.19 min; m/z 456 [M + H]+ |

Intermediate 70

2-[(4-methoxyphenyl)methyl]-6-(6-spiro[2H-benzofuran-3,1'-cyclopropane]-4-yloxy-3-pyridyl)-4H-imidazo[4,5-c]pyrazol-5-one

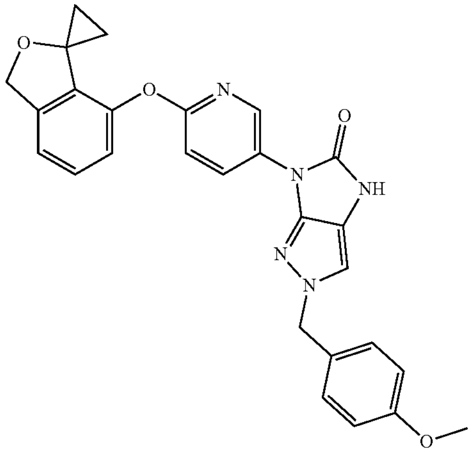 [SMILES: COc1ccc(Cn2cc3[nH]c(=O)n(-c4ccc(Oc5cccc6c5C5(CC5)OC6)nc4)c3n2)cc1]

To a solution of 1-[(4-methoxyphenyl)methyl]-N3-(6-spiro[2H-benzofuran-3,1'-cyclopropane]-4-yloxy-3-pyridyl)pyrazole-3,4-diamine (Intermediate 69, 20 mg, 0.044 mmol) and triethylamine (0.008 mL, 0.058 mmol) in ethyl acetate (4 mL), 1-1'-carbonyldiimidazole (10 mg, 0.064 mmol) was added and the reaction mixture was stirred at room temperature for 2 h. The reaction was diluted with ethyl acetate (30 mL) and washed with HCl 0.2M solution (20 mL). The two phases were separated and the organic one was collected, washed with brine (20 mL), dried over sodium sulphate, filtered and evaporated to dryness. The residue was purified by flash chromatography (Biotage System) on silica gel using a SFAR 5 g as column and Cyclohexane/Ethyl acetate from 60:40 to 10:90 as eluent, affording the title compound 2-[(4-methoxyphenyl)methyl]-6-(6-spiro[2H-benzofuran-3,1'-cyclopropane]-4-yloxy-3-pyridyl)-4H-imidazo[4,5-c]pyrazol-5-one (7 mg) as a red oil.

LC/MS: QC_3_MIN: Rt=2.48 min m/z 482 [M+H]+

Intermediate 71

2-chloro-N-(3-nitro-2-pyridyl)pyrimidin-5-amine

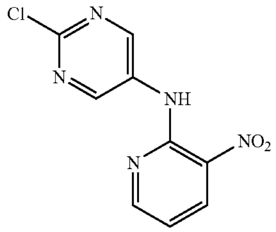

To a solution of 2-chloropyrimidin-5-amine (800 mg, 6.20 mmol) in dry dioxane (20 mL), 2-chloro-3-nitropyridine (1.96 g, 12.40 mmol), cesium carbonate (4.04 g, 12.4 mmol), 4,5-Bis(diphenylphosphino)-9,9-dimethylxanthene (270 mg, 0.47 mmol) and Palladium (II) acetate (69 mg, 0.31 mmol) were added and an argon-vacuum cycle was applied 3 times. The reaction mixture was stirred for 1 hour at 80° C. The mixture was diluted with ethyl acetate (30 mL) and the solids were filtered off. The resulting liquid phase was washed with water (20 mL) and brine (20 mL), dried over sodium sulphate, filtered and evaporated to dryness affording the title compound 2-chloro-N-(3-nitro-2-pyridyl)pyrimidin-5-amine (1.56 g) as a red-brown solid.

LC/MS: QC_3_MIN: Rt=2.09 min m/z 252 [M+H]+

Intermediate 72

N2-(2-chloropyrimidin-5-yl)pyridine-2,3-diamine

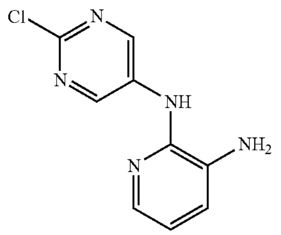 [SMILES: O=[N+]([O-])c1cccnc1Nc1cnc(Cl)nc1]

To a solution of 2-chloro-N-(3-nitropyridin-2-yl)pyrimidin-5-amine (Intermediate 71, 1.56 g, 5.49 mmol) in absolute ethanol (20 mL) and water (5 mL), ammonium chloride (588 mg, 11 mmol) and Iron Powder (615 mg, 11 mmol) were added and the reaction mixture was stirred for 16 hours at room temperature. The solids were filtered off and the filtrate was concentrated under vacuum. The residue was dissolved in ethyl acetate (30 mL) and washed with brine (50 mL). The organic layer was dried over $Na_2SO_4$, filtered and evaporated to dryness. The residue was purified by flash chromatography (Biotage System) on silica gel using a SFAR 25 g as column and Cyclohexane/Ethyl acetate from 80:20 to 20:80 as eluent affording the title compound N2-(2-chloropyrimidin-5-yl)pyridine-2,3-diamine (800 mg) as a brown solid.

LC/MS: QC_3_MIN: Rt=1.29 min m/z 222 [M+H]+

Intermediate 73

3-(2-chloropyrimidin-5-yl)-1H-imidazo[4,5-b]pyridin-2-one

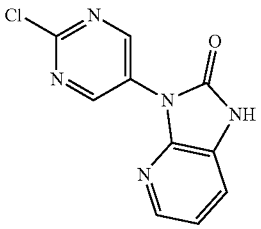 [SMILES: O=c1[nH]c2cccnc2n1-c1cnc(Cl)nc1]

To a solution of N2-(2-chloropyrimidin-5-yl)pyridine-2,3-diamine (Intermediate 72, 800 mg, 3.62 mmol) in dichloromethane (20 mL), triethylamine (1.32 mL, 7.24 mmol) was added, and the mixture was cooled to 0° C. Triphosgene (429 mg, 1.45 mmol) was added dropwise as a dichloromethane (15 mL) solution. The mixture was stirred at 0° C. for 10 minutes. The mixture was diluted with dichloromethane (30 mL) and washed with HCl 0.2 M solution (20 mL) and brine (5 mL). The organic layer was dried over sodium sulphate, filtered and evaporated to dryness affording an insoluble solid that was suspended in ethyl acetate (15 mL) and stirred overnight. After filtration, the solid was collected and dried affording the title compound 3-(2-chloropyrimidin-5-yl)-1H-imidazo[4,5-b]pyridin-2-one (140 mg) as light brown solid.

LC/MS: QC_3_MIN: Rt=1.75 min m/z 248 [M+H]+

Intermediate 74

2-[(3,3-dimethyl-2H-benzofuran-4-yl)oxy]-N-(4-nitro-3-pyridyl)pyrimidin-5-amine

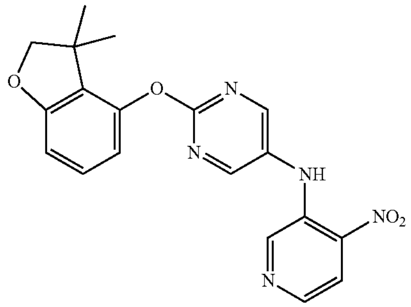 [SMILES: CC1(C)COc2cccc(Oc3ncc(Nc4cnccc4[N+](=O)[O-])cn3)c21]

A mixture of 2-[(3,3-dimethyl-2H-benzofuran-4-yl)oxy]pyrimidin-5-amine (WO2012/076877 Intermediate 65, 50 mg, 0.19 mmol), 3-bromo-4-nitro-pyridine (43 mg, 0.21 mmol), Xantphos (17 mg, 0.03 mmol), cesium carbonate (127 mg, 0.39 mmol) and $Pd(OAc)_2$ (4 mg, 0.02 mmol) in 1,4-dioxane (2 mL) was put under a vacuum-nitrogen flush and stirred at 95° C. for 1.5 hours. The mixture was then diluted in EtOAc (15 mL) and washed with water (20 mL) and then brine (20 mL). The organic layer was separated, dried over $Na_2SO_4$, filtered and concentrated under vacuum affording the title compound 2-[(3,3-dimethyl-2H-benzofuran-4-yl)oxy]-N-(4-nitro-3-pyridyl)pyrimidin-5-amine (104 mg) which was used in the next step without further purifications.

LC/MS: QC_3_MIN: Rt=2.47 min m/z 380 [M+H]+

The following compounds were prepared using analogous methods to the foregoing methodology, replacing 2-[(3,3-dimethyl-2H-benzofuran-4-yl)oxy]pyrimidin-5-amine (WO2012/076877 Intermediate 65) with the appropriate aniline and 3-bromo-4-nitro-pyridine with the appropriate nitro derivative. Reactions were heated at 95° C. for 1.5 to 2 h. Products were either isolated crude or were purified by flash-chromatography (Silica cartridge; Cyclohexane/EtOAc or other appropriate solvent system) and/or reverse chromatography (C-18 cartridge; water/acetonitrile or other appropriate solvent system).

| Int. | Structure | Name | Aniline | Nitro derivative | LC-MS |
|---|---|---|---|---|---|
| 75 | 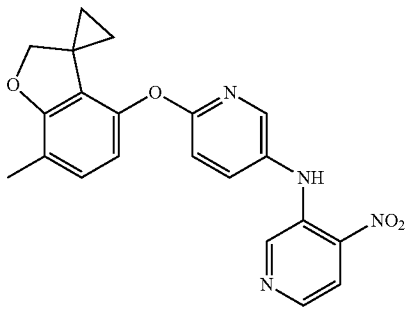 | 6-(7-methylspiro[2H-benzofuran-3,1'-cyclopropane]-4-yl)oxy-N-(4-nitro-3-pyridyl)pyridin-3-amine | 6-(7-methylspiro[2H-benzofuran-3,1'-cyclopropane]-4-yl)oxypyridin-3-amine (WO2012/076877 Intermediate 158) | 3-bromo-4-nitro-pyridine | LC/MS not available. |
| 76 | 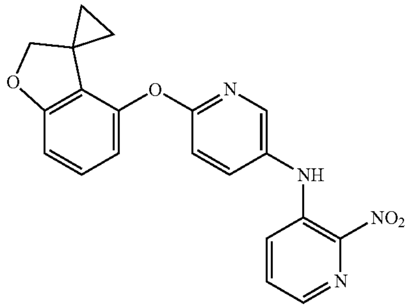 [SMILES: O=[N+]([O-])c1ncccc1Nc1ccc(Oc2cccc3c2C2(CC2)CO3)nc1] | 2-nitro-N-(6-spiro[2H-benzofuran-3,1'-cyclopropane]-4-yloxy-3-pyridyl)pyridin-3-amine | 6-spiro[2H-benzofuran-3,1'-cyclopropane]-4-yloxypyridin-3-amine (WO2012/076877 Intermediate 87) | 3-bromo-2-nitro-pyridine | LC/MS not available. |
| 77 | 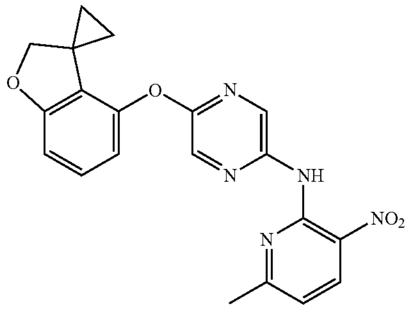 | N-(6-methyl-3-nitro-2-pyridyl)-5-spiro[2H-benzofuran-3,1'-cyclopropane]-4-yloxy-pyrazin-2-amine | 5-spiro[2H-benzofuran-3,1'-cyclopropane]-4-yloxypyrazin-2-amine (Intermediate 11) | 2-chloro-6-methyl-3-nitro-pyridine | LC/MS not available. |
| 78 | 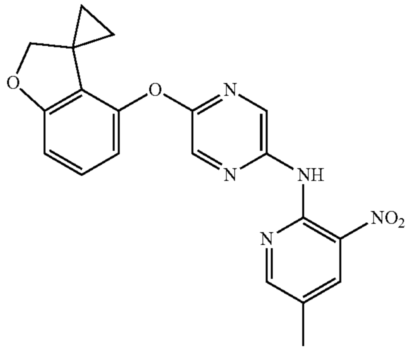 | N-(5-methyl-3-nitro-2-pyridyl)-5-spiro[2H-benzofuran-3,1'-cyclopropane]-4-yloxy-pyrazin-2-amine | 5-spiro[2H-benzofuran-3,1'-cyclopropane]-4-yloxypyrazin-2-amine (Intermediate 11) | 2-chloro-5-methyl-3-nitro-pyridine | LC/MS not available. |

Intermediate 79

N3-[2-[(3,3-dimethyl-2H-benzofuran-4-yl)oxy]pyrimidin-5-yl]pyridine-3,4-diamine

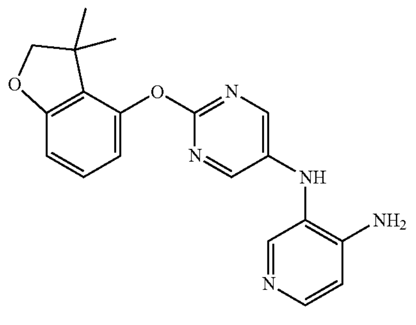

A mixture of 2-[(3,3-dimethyl-2H-benzofuran-4-yl)oxy]-N-(4-nitro-3-pyridyl)pyrimidin-5-amine (Intermediate 74, 104 mg, 0.27 mmol), iron (61 mg, 1.1 mmol) and ammonium chloride (59 mg, 1.1 mmol) in ethanol (4 mL) and water (1 mL) was stirred at RT for 16 hours. The reaction mixture was filtered and the solid washed with EtOAc (10 ml). The organic filtrate was collected and washed with water (10 ml) and then brine (10 ml). The organic layer was separated, dried over $Na_2SO_4$, filtered and concentrated under vacuum. The crude was then purified by Reverse Phase flash chromatography (Biotage System) on C-18 stationary phase using a SNAP C-18 12 g column eluting Water:Acetonitrile from 95:5 to 0:100. The desired fractions were collected and concentrated under vacuum to afford the title compound N3-[2-[(3,3-dimethyl-2H-benzofuran-4-yl)oxy]pyrimidin-5-yl]pyridine-3,4-diamine (23 mg) as a white solid.

LC/MS: QC_3_MIN: Rt=2.07 min m/z 350 [M+H]+

The following compounds were prepared using analogous methods to the foregoing methodology, replacing 2-[(3,3-dimethyl-2H-benzofuran-4-yl)oxy]-N-(4-nitro-3-pyridyl)pyrimidin-5-amine (Intermediate 72) with the appropriate nitro derivative. The reactions were performed with temperatures ranging from room temperature (rt) to 90° C. The conditions for each case are specified in the table. Final products were purified by flash-chromatography (Silica cartridge; Cyclohexane/EtOAc or other appropriate solvent system) and/or reverse chromatography (C-18 cartridge; water/acetonitrile or other appropriate solvent system).

| Int | Structure | Name | Nitro derivative | T (° C.)/h | LC-MS |
|---|---|---|---|---|---|
| 80 | 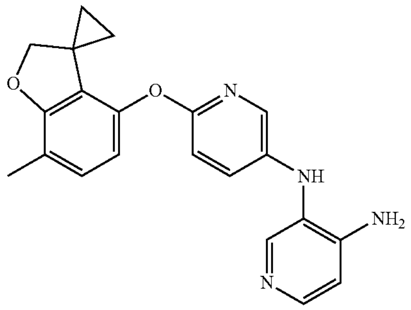 | N3-[6-(7-methylspiro[2H-benzofuran-3,1'-cyclopropane]-4-yl)oxy-3-pyridyl]pyridine-3,4-diamine | 6-(7-methylspiro[2H-benzofuran-3,1'-cyclopropane]-4-yl)oxy-N-(4-nitro-3-pyridyl)pyridin-3-amine (Intermediate 75) | 90° C. for 16 h | LC/MS: QC_3_MIN: Rt = 1.88 min [M + H]+ = 361 |
| 81 | 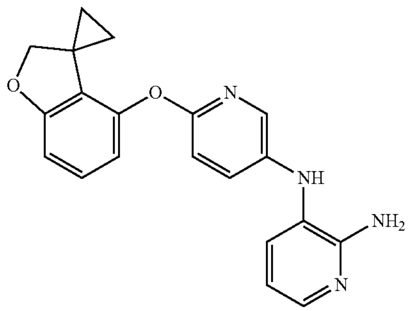 | N3-(6-spiro[2H-benzofuran-3,1'-cyclopropane]-4-yloxy-3-pyridyl)pyridine-2,3-diamine | 2-nitro-N-(6-spiro[2H-benzofuran-3,1'-cyclopropane]-4-yloxy-3-pyridyl)pyridin-3-amine (Intermediate 76) | rt for 18 h | LC/MS: QC_3_MIN: Rt = 1.96 min [M + H]+ = 347 |
| 82 | 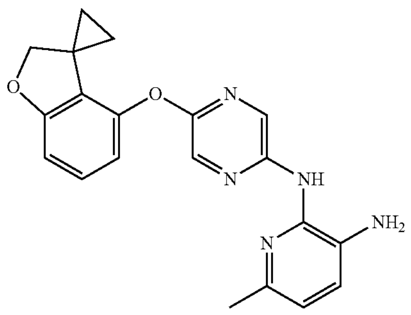 | 6-methyl-N2-(5-spiro[2H-benzofuran-3,1'-cyclopropane]-4-yloxypyrazin-2-yl)pyridine-2,3-diamine | N-(6-methyl-3-nitro-2-pyridyl)-5-spiro[2H-benzofuran-3,1'-cyclopropane]-4-yloxy-pyrazin-2-amine (Intermediate 77) | rt for 19 h then 60° C. for 2 h | LC/MS: QC_3_MIN: Rt = 2.06 min [M + H]+ = 362 |

-continued

| Int | Structure | Name | Nitro derivative | T (° C.)/h | LC-MS |
|---|---|---|---|---|---|
| 83 | 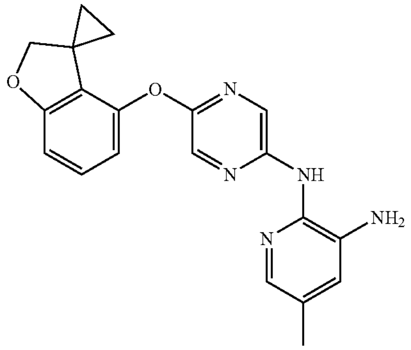 | 5-methyl-N2-(5-spiro[2H-benzofuran-3,1'-cyclopropane]-4-yloxypyrazin-2-yl)pyridine-2,3-diamine | N-(5-methyl-3-nitro-2-pyridyl)-5-spiro[2H-benzofuran-3,1'-cyclopropane]-4-yloxy-pyrazin-2-amine (Intermediate 78) | rt for 24 h, then 55° C. for 2 h, then 60° C. for 2 h and then rt for 96 h. | LC/MS: QC_3_MIN: Rt = 2.08 min [M + H]+ = 362 |

Intermediate 84

1-(2-bromo-3-pyridyl)-3-[2-[3-(trifluoromethoxy)phenoxy]pyrimidin-5-yl]urea

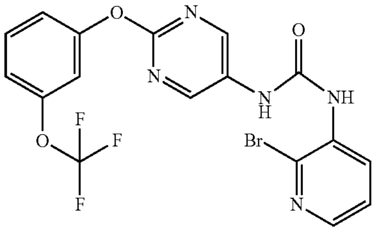 [SMILES: O=C(Nc1cnc(Oc2cccc(OC(F)(F)F)c2)nc1)Nc1cccnc1Br]

A mixture of bis(trichloromethyl) carbonate (32 mg, 0.1078 mmol) in dichloromethane (1.5 mL) was cooled to 0° C. A solution of 2-[3-(trifluoromethoxy)phenoxy]pyrimidin-5-amine (Intermediate 10, 75 mg, 0.2765 mmol) and N,N-diisopropylethylamine (148 mg, 1.1452 mmol) (0.20 mL) in dichloromethane (1.5 mL) was then added dropwise and the reaction mixture was left to stir at 0° C. for 1 hour. Vacuum was applied for several minutes to remove excess phosgene and then a solution of 4-(dimethylamino)pyridine (35 mg, 0.2865 mmol) in dichloromethane (0.5000 mL) was added dropwise and the reaction mixture was left to stir at 0° C. for 5 minutes. 2-bromopyridin-3-amine (55 mg, 0.3179 mmol) was added and the reaction mixture was left to stir at 0° C. for 1 hour. The mixture was concentrated under vacuum and the crude material was then purified by Reverse Phase flash chromatography (Biotage System) on silica gel using a SNAP C-18 12 g column eluting Water:Acetonitrile from 95:5 to 30:70. The desired fractions were collected and concentrated under vacuum to afford 1-(2-bromo-3-pyridyl)-3-[2-[3-(trifluoromethoxy)phenoxy]pyrimidin-5-yl]urea (18 mg) as a white solid.

LC/MS: QC_3_MIN: Rt=2.04 min m/z 470 & 472 [M+H]+

Example 1

3-[6-(7-methylspiro[2H-benzofuran-3,1'-cyclopropane]-4-yl)oxy-3-pyridyl]-1H-imidazo[4,5-b]pyridin-2-one

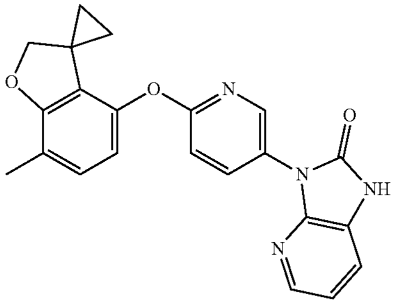 [SMILES: Cc1ccc(Oc2ccc(-n3c(=O)[nH]c4cccnc43)cn2)c2c1OCC21CC1]

To a solution of N2-[6-(7-methylspiro[2H-benzofuran-3,1'-cyclopropane]-4-yl)oxy-3-pyridyl]pyridine-2,3-diamine (Intermediate 32, 21 mg, 0.06 mmol) (Intermediate 29) in EtOAc (4 mL), 1-1'-carbonyldiimidazole (10.4 mg, 0.06 mmol) was added and the reaction mixture was stirred at room temperature for 2 h. The reaction was diluted with EtOAc (30 mL) and washed with HCl 0.2 M solution (20 mL). The two phases were separated and the organic one was collected, washed with brine (20 mL), dried over sodium sulphate, filtered, and evaporated to dryness. The residue was purified by flash chromatography on C-18 using a SNAP 10 g as column and $H_2O$/ACN from 95:5 to 20:80 as eluent. The desired fractions were collected and the solvent was removed under vacuum affording the title compound 3-[6-(7-methylspiro[2H-benzofuran-3,1'-cyclopropane]-4-yl)oxy-3-pyridyl]-1H-imidazo[4,5-b]pyridin-2-one (17 mg as a white solid.

LC/MS: QC_3_MIN: Rt=2.32 min m/z 387 [M+H]+ 1H-NMR (400 MHZ; DMSO-d6): δ ppm 11.44 (bs, 1H), 8.37 (d, 1H), 8.07 (dd, 1H), 7.90 (dd, 1H), 7.35-7.41 (m, 1H), 7.05-7.11 (m, 2H), 6.90 (d, 1H), 6.43 (d, 1H), 4.42 (s, 2H), 2.11 (s, 3H), 1.07-1.20 (m, 2H), 0.83-0.88 (m, 2H).

Example 2

7-methyl-3-[6-(7-methylspiro[2H-benzofuran-3,1'-cyclopropane]-4-yl)oxy-3-pyridyl]-1H-imidazo[4,5-b]pyridin-2-one

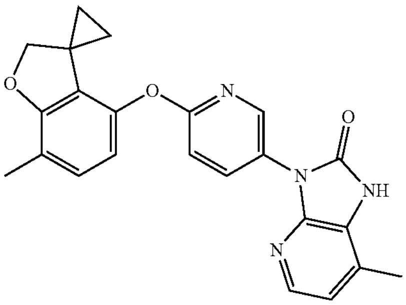

4-methyl-N2-[6-(7-methylspiro[2H-benzofuran-3,1'-cyclopropane]-4-yl)oxy-3-pyridyl]pyridine-2,3-diamine (Intermediate 33, 25 mg, 0.07 mmol) and triethylamine (20 uL, 0.17 mmol) were mixed in dichloromethane (5 mL) and the mixture cooled to 0° C. A solution of triphosgene (8 mg, 0.03 mmol) in dichloromethane (2 mL) was slowly added and the reaction mixture was stirred at OC for 30 min. The reaction was diluted with ethyl acetate (30 mL) and washed with an aqueous 0.2 M HCl solution (20 mL). The two phases were separated and the organic one washed with brine (20 mL), dried over sodium sulphate, filtered and evaporated to dryness. The residue was purified by flash chromatography on silica gel (BIOTAGE SYSTEM) using a SFAR 5 g as column and DCM/MeOH from 99.5:0.5 to 95:5 as eluent. The desired fractions were collected and the solvent was removed under vacuum affording the title compound 7-methyl-3-[6-(7-methylspiro[2H-benzofuran-3,1'-cyclopropane]-4-yl)oxy-3-pyridyl]-1H-imidazo[4,5-b]pyridin-2-one (9 mg) (Example 2) as a white solid.

LC/MS: QC_3_MIN: Rt=2.39 min m/z 401 [M+H]+ 401 & 823 [2M+Na]+.

The following compounds were prepared using analogous methods to the foregoing methodology, replacing 4-methyl-N2-[6-(7-methylspiro[2H-benzofuran-3,1'-cyclopropane]-4-yl)oxy-3-pyridyl]pyridine-2,3-diamine (Intermediate 33) with the appropriate diamine. Final products were purified by flash-chromatography (Silica cartridge using Cyclohexane/EtOAc or DCM/Methanol as eluent and/or C-18 cartridge using water/acetonitrile as eluent).

| Ex | Structure | Name | Diamine | NMR | LC-MS |
|---|---|---|---|---|---|
| 3 | 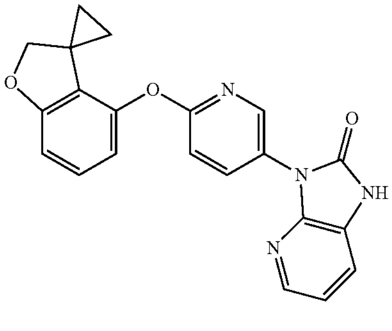 [SMILES: O=c1[nH]c2cccnc2n1-c1ccc(Oc2cccc3c2C2(CC2)CO3)nc1] | 3-(6-spiro[2H-benzofuran-3,1'-cyclopropane]-4-yloxy-3-pyridyl)-1H-imidazo[4,5-b]pyridin-2-one | N2-(6-spiro[2H-benzofuran-3,1'-cyclopropane]-4-yloxy-3-pyridyl)pyridine-2,3-diamine (Intermediate 34) | $^1$H-NMR (400 MHz; DMSO-d6): δ ppm 11.45 (s, 1H), 8.40 (dd, 1H), 8.10 (dd, 1H), 7.90 (dd, 1H), 7.38 (dd, 1H), 7.13 (dd, 1H), 7.04-7.10 (m, 2H), 6.64 (dd, 1H), 6.51 (dd, 1H), 4.43 (s, 2H), 1.11-1.20 (m, 2H), 0.87-0.93 (m, 2H) | LC/MS: QC_3_MIN: Rt = 2.22 min m/z 373 [M + H]+ |
| 4 | 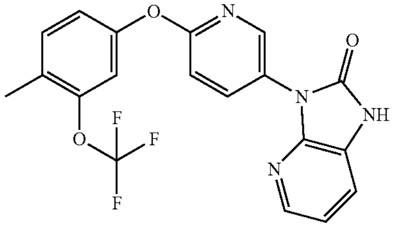 | 3-[6-[4-methyl-3-(trifluoromethoxy) phenoxy]-3-pyridyl]-1H-imidazo[4,5-b]pyridin-2-one | N2-[6-[4-methyl-3-(trifluoromethoxy) phenoxy]-3-pyridyl]pyridine-2,3-diamine (Intermediate 35) | $^1$H-NMR (400 MHz; DMSO-d6): δ ppm 11.45 (s, 1H), 8.39 (d, 1H), 8.13 (dd, 1H), 7.90 (dd, 1H), 7.40-7.46 (m, 1H), 7.38 (dd, 1H), 7.18-7.24 (m, 2H), 7.15 (dd, 1H), 7.08 (dd, 1H), 2.26 (s, 3H) | LC/MS: QC_3_MIN: Rt = 2.42 min m/z 403 [M + H]+ |
| 5 | 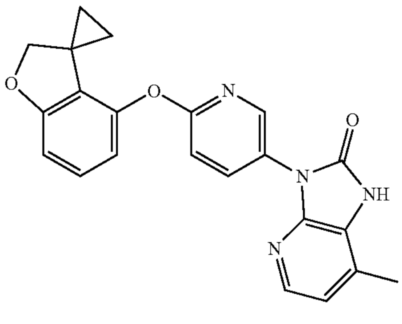 [SMILES: Cc1ccnc2c1[nH]c(=O)n2-c1ccc(Oc2cccc3c2C2(CC2)CO3)nc1] | 7-methyl-3-(6-spiro[2H-benzofuran-3,1'-cyclopropane]-4-yloxy-3-pyridyl)-1H-imidazo[4,5-b]pyridin-2-one | 4-methyl-N2-(6-spiro[2H-benzofuran-3,1'-cyclopropane]-4-yloxy-3-pyridyl)pyridine-2,3-diamine (Intermediate 36) | — | LC/MS: QC_3_MIN: Rt = 2.27 min m/z 387 [M + H]+ m/z 795 [2M + Na]+ |

-continued

| Ex | Structure | Name | Diamine | NMR | LC-MS |
|---|---|---|---|---|---|
| 6 | 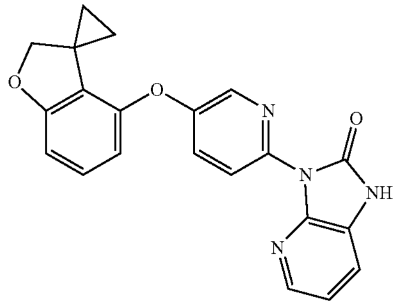 [SMILES: O=c1[nH]c2cccnc2n1-c1ccc(Oc2cccc3c2C2(CC2)CO3)cn1] | 3-(5-spiro[2H-benzofuran-3,1'-cyclopropane]-4-yloxy-2-pyridyl)-1H-imidazo[4,5-b]pyridin-2-one | N2-(5-spiro[2H-benzofuran-3,1'-cyclopropane]-4-yloxy-2-pyridyl)pyridine-2,3-diamine (Intermediate 37) | — | LC/MS: QC_3_MIN: Rt = 2.15 min m/z 373[M + H]+ m/z 767 [2M + Na]+ |
| 7 | 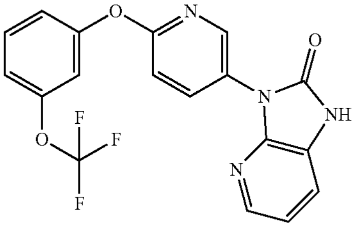 [SMILES: O=c1[nH]c2cccnc2n1-c1ccc(Oc2cccc(OC(F)(F)F)c2)nc1] | 3-[6-[3-(trifluoro-methoxy) phenoxy]-3-pyridyl]-1H-imidazo[4,5-b]pyridin-2-one | N2-[6-[3-(trifluoro-methoxy) phenoxy]-3-pyridyl]pyridine-2,3-diamine (Intermediate 38) | — | LC/MS: QC_3_MIN: Rt = 2.33 min m/z 387[M + H]+ m/z 799 [2M + Na]+ |
| 8 | 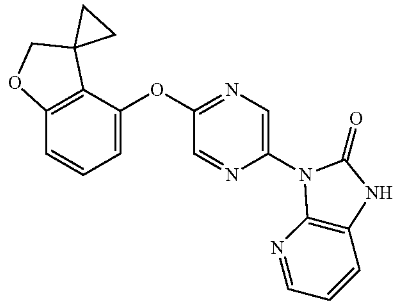 [SMILES: O=c1[nH]c2cccnc2n1-c1cnc(Oc2cccc3c2C2(CC2)CO3)cn1] | 3-(5-spiro[2H-benzofuran-3,1'-cyclopropane]-4-yloxypyrazin-2-yl)-1H-imidazo[4,5-b]pyridin-2-one | N2-(5-spiro[2H-benzofuran-3,1'-cyclopropane]-4-yloxypyrazin-2-yl)pyridine-2,3-diamine (Intermediate 39) | $^1$H-NMR (400 MHz; DMSO-d6): δ ppm 11.50 (s, 1H), 8.58 (d, 1H), 8.46 (d, 1H), 7.89 (dd, 1H), 7.41 (dd, 1H), 7.06-7.12 (m, 2H), 6.68 (dd, 1H), 6.62 (dd, 1H), 4.45 (s, 2H), 1.13-1.19 (m, 2H), 0.91-0.97 (m, 2H) | LC/MS: QC_3_MIN: Rt = 2.14 m/z 374 [M + H]+ |
| 9 | 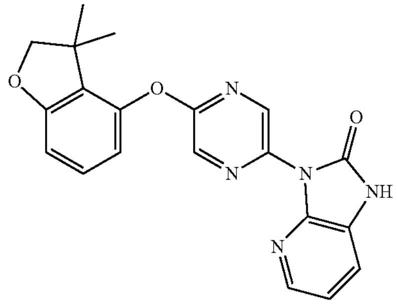 [SMILES: CC1(C)COc2cccc(Oc3cnc(-n4c(=O)[nH]c5cccnc54)cn3)c21] | 3-[5-[(3,3-dimethyl-2H-benzofuran-4-yl)oxy] pyrazin-2-yl]-1H-imidazo[4,5-b]pyridin-2-one | N2-[5-[(3,3-dimethyl-2H-benzofuran-4-yl)oxy]pyrazin-2-yl]pyridine-2,3-diamine (Intermediate 40) | — | LC/MS: QC_3_MIN: Rt = 2.20 min m/z 376 [M + H]+ |
| 10 | 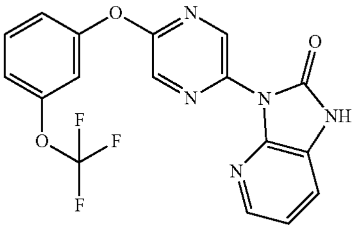 | 3-[5-[3-(trifluoro-methoxy) phenoxy] pyrazin-2-yl]-1H-imidazo[4,5-b]pyridin-2-one | N2-[5-[3-(trifluoro-methoxy) phenoxy]pyrazin-2-yl]pyridine-2,3-diamine (Intermediate 41) | $^1$H-NMR (400 MHz; DMSO-d6): δ ppm 11.49 (s, 1H), 8.65 (d, 1H), 8.46 (d, 1H), 7.89 (dd, 1H), 7.59 (t, 1H), 7.42-7.45 (m, 1H), 7.41 (dd, 1H), 7.33-7.37 (m, 1H), 7.27-7.32 (m, 1H), 7.10 (dd, 1H) | LC/MS: QC_3_MIN: Rt = 2.29 min m/z 390 [M + H]+ |

-continued

| Ex | Structure | Name | Diamine | NMR | LC-MS |
|---|---|---|---|---|---|
| 11 | 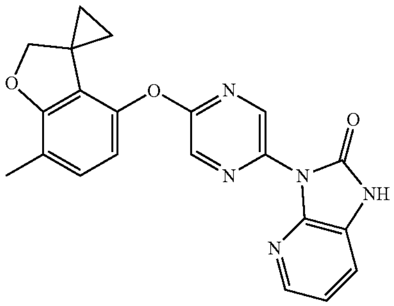 [SMILES: Cc1ccc(Oc2cnc(-n3c(=O)[nH]c4cccnc43)cn2)c2c1OCC21CC1] | 3-[5-(7-methylspiro[2H-benzofuran-3,1'-cyclopropane]-4-yl)oxypyrazin-2-yl]-1H-imidazo[4,5-b]pyridin-2-one | N2-[5-(7-methylspiro[2H-benzofuran-3,1'-cyclopropane]-4-yl)oxypyrazin-2-yl]pyridine-2,3-diamine (Intermediate 42) | $^1$H-NMR (400 MHz; DMSO-d6): δ ppm 11.49 (s, 1H), 8.54 (s, 1H), 8.44 (s, 1H), 7.89 (d, 1H), 7.37-7.43 (m, 1H), 7.09 (dd, 1H), 6.93 (d, 1H), 6.53 (d, 1H), 4.44 (s, 2H), 2.12 (s, 3H), 1.08-1.14 (m, 2H), 0.89-0.95 (m, 2H). | LC/MS: QC_3_MIN: Rt = 2.24 min m/z 388 [M + H]+ |
| 12 | 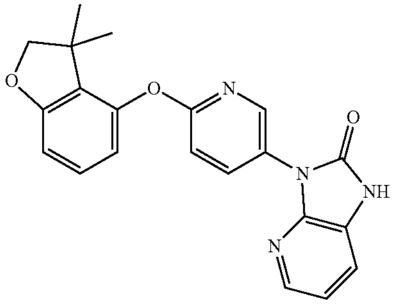 [SMILES: CC1(C)COc2cccc(Oc3ccc(-n4c(=O)[nH]c5cccnc54)cn3)c21] | 3-[6-[(3,3-dimethyl-2H-benzofuran-4-yl)oxy]-3-pyridyl]-1H-imidazo[4,5-b]pyridin-2-one | N2-[6-[(3,3-dimethyl-2H-benzofuran-4-yl)oxy]-3-pyridyl]pyridine-2,3-diamine (Intermediate 43) | $^1$H-NMR (400 MHz; DMSO-d6): δ ppm 11.44 (s, 1H), 8.41 (d, 1H), 8.10 (dd, 1H), 7.90 (dd, 1H), 7.38 (dd, 1H), 7.18 (d, 1H), 7.05-7.15 (m, 2H), 6.63 (d, 1H), 6.56 (s, 1H), 4.19 (s, 2H), 1.27 (s, 6H) | LC/MS: QC_3_MIN: Rt = 2.21 min m/z 375 [M + H]+ |
| 13 | 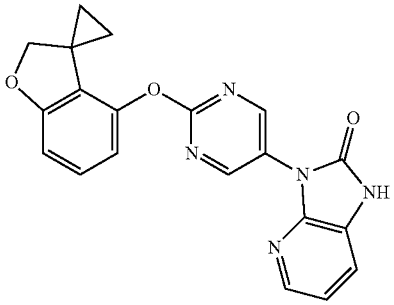 | 3-(2-{2H-spiro[1-benzofuran-3,1'-cyclopropane]oxy}pyrimidin-5-yl)-1H,2H,3H-imidazo[4,5-b]pyridin-2-one | N2-(2-spiro[2H-benzofuran-3,1'-cyclopropane]-4-yloxypyrimidin-5-yl)pyridine-2,3-diamine (Intermediate 44) | $^1$H-NMR (400 MHz; DMSO-d6): δ ppm 11.56 (s, 1H), 8.96 (s, 2H), 7.93 (dd, 1H), 7.41 (dd, 1H), 7.06-7.14 (m, 2H), 6.68 (dd, 1H), 6.62 (dd, 1H), 4.43 (s, 2H), 1.06-1.11 (m, 2H), 0.89-0.94 (m, 2H) | LC/MS: QC_3_MIN: Rt = 2.12 min m/z 374 [M + H]+ |
| 14 | 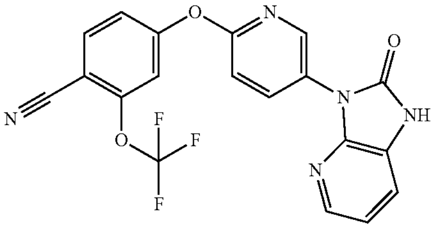 [SMILES: N#Cc1ccc(Oc2ccc(-n3c(=O)[nH]c4cccnc43)cn2)cc1OC(F)(F)F] | 4-[[5-(2-oxo-1H-imidazo[4,5-b]pyridin-3-yl)-2-pyridyl]oxy]-2-(trifluoro-methoxy) benzonitrile | 4-[[5-[(3-amino-2-pyridyl)amino]-2-pyridyl]oxy]-2-(trifluoromethoxy) benzonitrile (Intermediate 45) | — | LC/MS: QC_3_MIN: Rt = 2.27 min m/z 414 [M + H]+ |
| 15 | 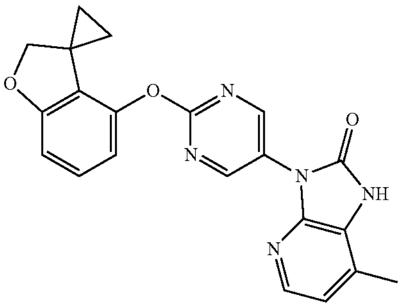 | 7-methyl-3-(2-spiro[2H-benzofuran-3,1'-cyclopropane]-4-yloxypyrimidin-5-yl)-1H-imidazo[4,5-b]pyridin-2-one | 4-methyl-N2-(2-spiro[2H-benzofuran-3,1'-cyclopropane]-4-yloxypyrimidin-5-yl)pyridine-2,3-diamine (Intermediate 46) | — | LC/MS: QC_3_MIN: Rt = 2.19 min m/z 388 [M + H]+ |

-continued

| Ex | Structure | Name | Diamine | NMR | LC-MS |
|---|---|---|---|---|---|
| 16 | 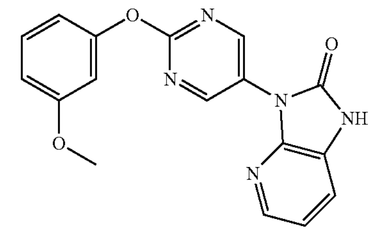 [SMILES: COc1cccc(Oc2ncc(-n3c(=O)[nH]c4cccnc43)cn2)c1] | 3-[2-(3-methoxy-phenoxy) pyrimidin-5-yl]-1H-imidazo[4,5-b]pyridin-2-one | N2-[2-(3-methoxyphenoxy) pyrimidin-5-yl]pyridine-2,3-diamine (Intermediate 47) | — | LC/MS: QC_3_MIN: Rt = 2.09 min m/z 336 [M + H]+ |
| 18 | 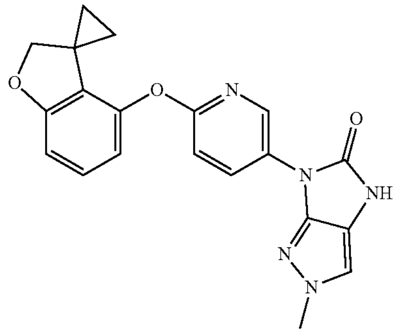 [SMILES: Cn1cc2[nH]c(=O)n(-c3ccc(Oc4cccc5c4C4(CC4)CO5)nc3)c2n1] | 2-methyl-6-(6-spiro[2H-benzofuran-3,1'-cyclopropane]-4-yloxy-3-pyridyl)-4H-imidazo[4,5-c]pyrazol-5-one | 1-methyl-N3-(6-spiro[2H-benzofuran-3,1'-cyclopropane]-4-yloxy-3-pyridyl)pyrazole-3,4-diamine (Intermediate 64) | — | LC/MS: QC_3_MIN: Rt = 2.23 min m/z 376 [M + H]+ |
| 19 | 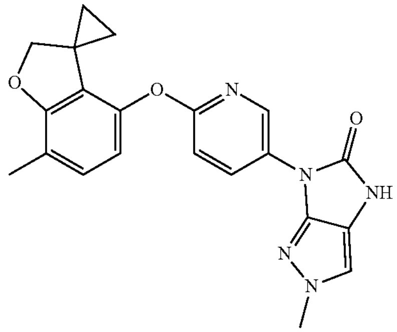 [SMILES: Cc1ccc(Oc2ccc(-n3c(=O)[nH]c4cn(C)nc43)cn2)c2c1OCC21CC1] | 2-methyl-6-[6-(7-methylspiro [2Hbenzofuran-3,1'-cyclopropane]-4-yl)oxy-3-pyridyl]-4H-imidazo[4,5-c]pyrazol-5-one | 1-methyl-N3-[6-(7-methylspiro[2H-benzofuran-3,1'-cyclopropane]-4-yl)oxy-3-pyridyl]pyrazole-3,4-diamine (Intermediate 65) | — | LC/MS: QC_3_MIN: Rt = 2.29 min; m/z 390 [M + H]+. |
| 20 | 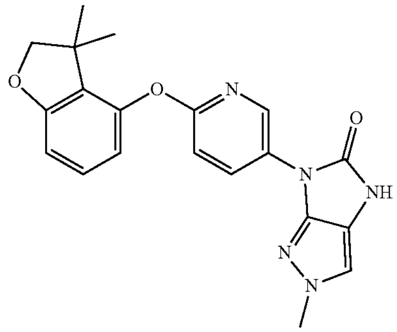 [SMILES: Cn1cc2[nH]c(=O)n(-c3ccc(Oc4cccc5c4C(C)(C)CO5)nc3)c2n1] | 6-[6-[(3,3-dimethyl-2H-benzofuran-4-yl)oxy]-3-pyridyl]-2-methyl-4H-imidazo[4,5-c]pyrazol-5-one | N3-[6-[(3,3-dimethyl-2H-benzofuran-4-yl)oxy]-3-pyridyl]-1-methyl-pyrazole-3,4-diamine (Intermediate 66) | — | LC/MS: QC_3_MIN: Rt = 2.24 min; m/z 378 [M + H]+. |
| 21 | 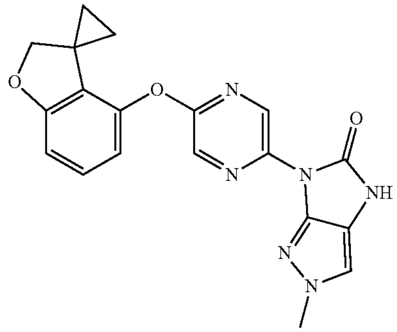 [SMILES: Cn1cc2[nH]c(=O)n(-c3cnc(Oc4cccc5c4C4(CC4)CO5)cn3)c2n1] | 2-methyl-6-(5-spiro[2H-benzofuran-3,1'-cyclopropane]-4-yloxypyrazin-2-yl)-4H-imidazo[4,5-c]pyrazol-5-one | 1-methyl-N3-(5-spiro[2H-benzofuran-3,1'-cyclopropane]-4-yloxypyrazin-2-yl)pyrazole-3,4-diamine (Intermediate 67) | — | LC/MS: QC_3_MIN: Rt = 2.13 min; m/z 377 [M + H]+. |

-continued

| Ex | Structure | Name | Diamine | NMR | LC-MS |
|---|---|---|---|---|---|
| 22 | 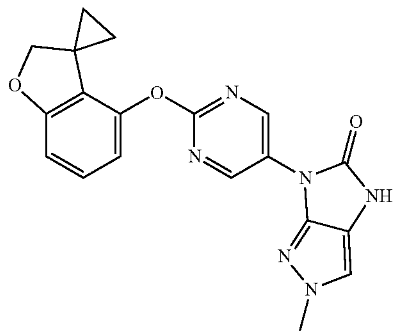 [SMILES: Cn1cc2[nH]c(=O)n(-c3cnc(Oc4cccc5c4C4(CC4)CO5)nc3)c2n1] | 2-methyl-6-(2-spiro[2H-benzofuran-3,1'-cyclopropane]-4-yloxypyrimidin-5-yl)-4H-imidazo[4,5-c]pyrazol-5-one | 1-methyl-N3-(2-spiro[2H-benzofuran-3,1'-cyclopropane]-4-yloxypyrimidin-5-yl)pyrazole-3,4-diamine (Intermediate 68) | — | LC/MS: QC_3_MIN: Rt = 2.10 min; m/z 377 [M + H]+, 775 [2M + Na]+ |
| 23 | 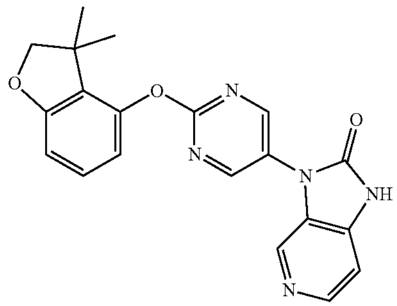 [SMILES: CC1(C)COc2cccc(Oc3ncc(-n4c(=O)[nH]c5ccncc54)cn3)c21] | 3-[2-[(3,3-dimethyl-2H-benzofuran-4-yl)oxy] pyrimidin-5-yl]-1H-imidazo[4,5-c]pyridin-2-one | N3-[2-[(3,3-dimethyl-2H-benzofuran-4-yl)oxy]pyrimidin-5-yl]pyridine-3,4-diamine (Intermediate 79) | — | LC/MS: QC_3_MIN: Rt = 2.10 min; m/z 376 [M + H]+. |

Example 17

3-[2-[3-(trifluoromethoxy)phenoxy]pyrimidin-5-yl]-1H-imidazo[4,5-b]pyridin-2-one

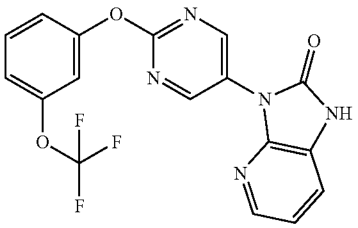 [SMILES: O=c1[nH]c2cccnc2n1-c1cnc(Oc2cccc(OC(F)(F)F)c2)nc1]

To a solution of N2-[2-[3-(trifluoromethoxy)phenoxy] pyrimidin-5-yl]pyridine-2,3-diamine (Intermediate 48, 786 mg, 2.1636 mmol) in ethyl acetate (5 mL), were added 1-1'-carbonyldiimidazole (491.15 mg, 3.029 mmol) and triethylamine (580.4 mg, 5.7357 mmol) the reaction mixture was stirred at room temperature for 4 hrs. The reaction was diluted with ethyl acetate (50 ml) and washed with an aqueous 0.2N solution of HCl (30 ml). The two phases were separated and the organic one was collected, washed with brine (30 ml), dried over sodium sulphate, filtered and evaporated to dryness. The residue was suspended in iPrOH (10 Volumes) and the mixture was stirred at 80 C until the complete dissolution and then overnight at RT. The solid was filtered off under vacuum and the filtrate was evaporated on vacuum, dissolved in EtOAc and filtered on a SFAR silica column 10 g. This filtrate was put together to the previous solid and the crude was suspended in EtOAc (10 Volumes). The mixture was stirred at 70 C until the complete dissolution and then Cyclohexane (10 Volumes) was added. The heating was switched off and the mixture was stirred for 2 h at RT. the solid was filtered under vacuum affording 3-[2-[3-(trifluoromethoxy)phenoxy]pyrimidin-5-yl]-1H-imidazo[4,5-b]pyridin-2-one (424 mg) as light pink solid.

LC/MS: QC_3_MIN: Rt=2.63 min; m/z 390 [M+H]+

$^1$H-NMR (400 MHZ; DMSO-d6): δ ppm 11.56 (s, 1H), 8.98 (s, 2H), 7.93 (dd, 1H), 7.58 (t, 1H), 7.40-7.44 (m, 2H), 7.35 (ddd, 1H), 7.26-7.32 (m, 1H), 7.11 (dd, 1H)

Example 24

2-methyl-9-[6-[3-(trifluoromethoxy)phenoxy]-3-pyridyl]-7H-purin-8-one

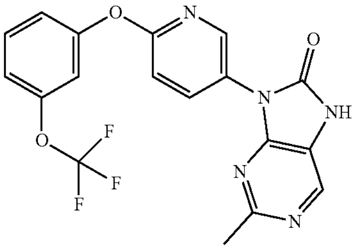 [SMILES: Cc1ncc2[nH]c(=O)n(-c3ccc(Oc4cccc(OC(F)(F)F)c4)nc3)c2n1]

A mixture of 1-(4-chloro-2-methyl-pyrimidin-5-yl)-3-[6-[3-(trifluoromethoxy)phenoxy]-3-pyridyl]urea (Intermediate 49, 27 mg, 0.0614 mmol), cesium carbonate (140 mg, 0.4297 mmol), Xantphos (24 mg, 0.0415 mmol), and $Pd(OAc)_2$ (5 mg, 0.0223 mmol) in 1,4-dioxane (1 mL) was put under a vacuum-nitrogen flush and stirred at 95° C. for 2 hours. The reaction mixture was quenched with $NH_4Cl$ (10 mL) and water (10 mL), then extracted with ethyl acetate (15 mL). The organic layer was washed with brine (15 mL), dried over $Na_2SO_4$, filtered then concentrated in vacuo. Flash chromatography (Biotage system) was used to purify the residue using a MODUS 5 g column and cyclohexane: ethyl acetate from 90:10 to 0:100 followed by DCM:Methanol 80:20. The fractions were concentrated in vacuo and further purified by reverse phase chromatography using a C-18 12 g column and water:acetonitrile from 95:5 to 40:60 as eluent to afford the title compound 2-methyl-9-[6-[3-(trifluoromethoxy)phenoxy]-3-pyridyl]-7H-purin-8-one (1 mg) as a white solid.

LC/MS: QC_3_MIN: Rt=2.19 min; m/z 404 [M+H]+ 1H-NMR (400 MHZ; $CDCl_3$): δ ppm 9.11 (s, 1H), 8.58 (dd, 1H), 8.30 (s, 1H), 8.10 (dd, 1H), 7.42-7.47 (m, 1H), 7.13-7.18 (m, 2H), 7.09-7.13 (m, 2H), 2.66 (s, 3H).

The following compounds were prepared using analogous methods to the foregoing methodology, replacing 1-(4-chloro-2-methyl-pyrimidin-5-yl)-3-[6-[3-(trifluoromethoxy)phenoxy]-3-pyridyl]urea with the appropriate urea intermediate. Final products were purified by flash-chromatography (Silica cartridge; Cyclohexane/EtOAc or other appropriate solvent system) and/or reverse chromatography (C-18 cartridge; water/acetonitrile or other appropriate solvent system).

| Ex. | Structure | Name | Urea intermediate | LCMS |
|---|---|---|---|---|
| 17 | 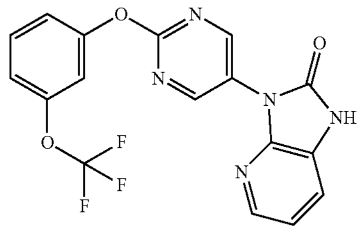 [SMILES: O=c1[nH]c2cccnc2n1-c1cnc(Oc2cccc(OC(F)(F)F)c2)nc1] | 3-[2-[3-(trifluoromethoxy)phenoxy]pyrimidin-5-yl]-1H-imidazo[4,5-b]pyridin-2-one | 1-(2-bromo-3-pyridyl)-3-[2-[3-(trifluoromethoxy)phenoxy]pyrimidin-5-yl]urea (Intermediate 84) | LC/MS: QC_3_MIN: Rt = 1.94 min; m/z 390 [M + H]+ |
| 25 | 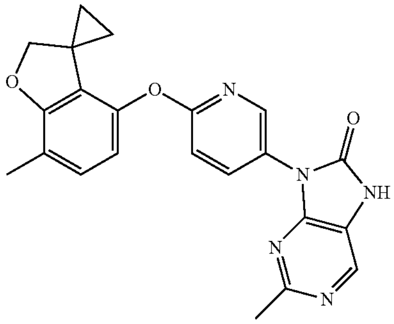 [SMILES: Cc1ncc2[nH]c(=O)n(-c3ccc(Oc4ccc(C)c5c4C4(CC4)CO5)nc3)c2n1] | 2-methyl-9-[6-(7-methylspiro[2H-benzofuran-3,1'-cyclopropane]-4-yl)oxy-3-pyridyl]-7H-purin-8-one | 1-(4-chloro-2-methyl-pyrimidin-5-yl)-3-[6-(7-methylspiro[2H-benzofuran-3,1'-cyclopropane]-4-yl)oxy-3-pyridyl]urea (Intermediate 50) | LC/MS: QC_3_MIN: Rt = 1.98 min; m/z 402 [M + H]+ |
| 26 | 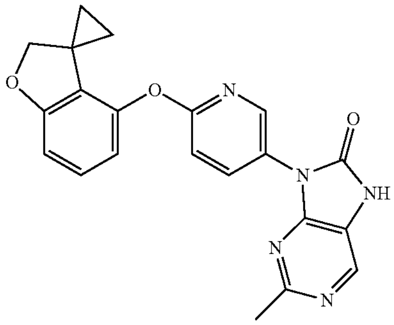 [SMILES: Cc1ncc2[nH]c(=O)n(-c3ccc(Oc4cccc5c4C4(CC4)CO5)nc3)c2n1] | 2-methyl-9-(6-spiro[2H-benzofuran-3,1'-cyclopropane]-4-yloxy-3-pyridyl)-7H-purin-8-one | 1-(4-chloro-2-methyl-pyrimidin-5-yl)-3-(6-spiro[2H-benzofuran-3,1'-cyclopropane]-4-yloxy-3-pyridyl)urea (Intermediate 52) | LC/MS: QC_3_MIN: Rt = 2.04 min; m/z 388 [M + H]+ |
| 27 | 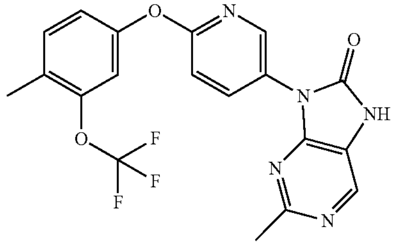 [SMILES: Cc1ncc2[nH]c(=O)n(-c3ccc(Oc4ccc(C)c(OC(F)(F)F)c4)nc3)c2n1] | 2-methyl-9-[6-[4-methyl-3-(trifluoromethoxy)phenoxy]-3-pyridyl]-7H-purin-8-one | 1-(4-chloro-2-methyl-pyrimidin-5-yl)-3-[6-[4-methyl-3-(trifluoromethoxy)phenoxy]-3-pyridyl]urea (Intermediate 53) | LC/MS: QC_3_MIN: Rt = 2.23 min; m/z 418 [M + H]+ |

-continued

| Ex. | Structure | Name | Urea intermediate | LCMS |
|---|---|---|---|---|
| 28 | 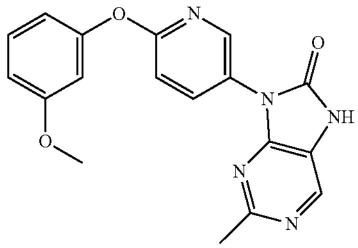 [SMILES: COc1cccc(Oc2ccc(-n3c(=O)[nH]c4cnc(C)nc43)cn2)c1] | 9-[6-(3-methoxyphenoxy)-3-pyridyl]-2-methyl-7H-purin-8-one | 1-(4-chloro-2-methyl-pyrimidin-5-yl)-3-[6-(3-methoxyphenoxy)-3-pyridyl]urea (Intermediate 54) | LC/MS: QC_3_MIN: Rt = 1.89 min; m/z 350 [M + H]+ |
| 29 | 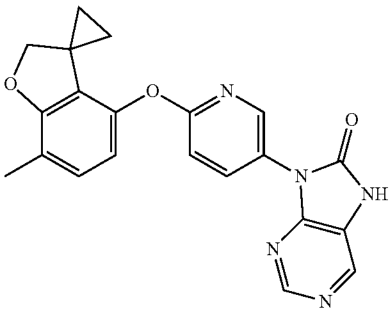 [SMILES: Cc1ccc(Oc2ccc(-n3c(=O)[nH]c4cncnc43)cn2)c2c1OCC21CC1] | 9-[6-(7-methylspiro[2H-benzofuran-3,1'-cyclopropane]-4-yl)oxy-3-pyridyl]-7H-purin-8-one | 1-(4-chloropyrimidin-5-yl)-3-[6-(7-methylspiro[2H-benzofuran-3,1'-cyclopropane]-4-yl)oxy-3-pyridyl]urea (Intermediate 51) | LC/MS: QC_3_MIN: Rt = 2.23 min; m/z 388 [M + H]+ |

Example 30

9-[6-[(3,3-dimethyl-2H-benzofuran-4-yl)oxy]-3-pyridyl]-2-methyl-7H-purin-8-one

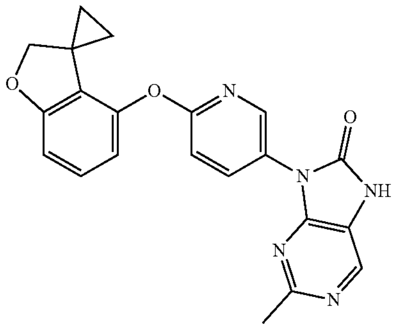 [SMILES: Cc1ncc2[nH]c(=O)n(-c3ccc(Oc4cccc5c4C4(CC4)CO5)nc3)c2n1]

A mixture of 9-(6-fluoro-3-pyridyl)-2-methyl-7H-purin-8-one (Intermediate 56, 12 mg, 0.0489 mmol), dipotassium carbonate (11 mg, 0.0796 mmol) and 3,3-dimethyl-2H-benzofuran-4-ol (Intermediate 50 WO2012/076877, 8.5 mg, 0.0518 mmol), in dimethyl sulfoxide (5 mL) was put under a vacuum-nitrogen flush and stirred at 120° C. for 1 hour, then 135° C. for 4 hours. 3-3-dimethyl-2H-benzofuran-4-ol (2 mg) was added and the reaction mixture was stirred at 135° C. for 4 hours. The reaction was filtered and concentrated in vacuo. The residue was then diluted with ethyl acetate (20 mL) then washed with water (5×20 mL). The organic layer was then dried over $Na_2SO_4$ then concentrated in vacuo.

In a separate vial, a mixture of 9-(6-fluoro-3-pyridyl)-2-methyl-7H-purin-8-one (Intermediate 56, 17 mg, 0.0693 mmol), dipotassium carbonate (potassium carbonate) (14 mg, 0.1013 mmol), 3,3-dimethyl-2H-benzofuran-4-ol (12 mg, 0.0731 mmol), and in dimethyl sulfoxide (1 mL) was put under a vacuum-nitrogen flush and stirred at 120° C. for 1 hour, then 135° C. for 4 hours. 3-3-dimethyl-2H-benzofuran-4-ol (2 mg) was added and the reaction mixture was stirred at 135° C. for 24 hours. The reaction mixture was quenched with water (10 mL) then extracted with ethyl acetate (2×10 mL). The organic layer was then washed with water (2×10 mL) then brine (10 mL), dried over $Na_2SO_4$, filtered then concentrated in vacuo. At this point, both reaction vials were combined for the purification. The residue was then purified by flash column chromatography (Biotage system) using a MODUS 12 g column and DCM: Methanol from 99:1 to 95:5 as eluent, followed by reverse phase chromatography (Biotage system) using a C-18 25 g column and water:acetonitrile from 95:5 to 55:45. The title compound 9-[6-[(3,3-dimethyl-2H-benzofuran-4-yl)oxy]-3-pyridyl]-2-methyl-7H-purin-8-one (1.2 mg) was isolated as a white solid. LC/MS: QC_3_MIN: Rt=2.07 min; m/z 390 [M+H]+

Example 31

3-[2-(7-methylspiro[2H-benzofuran-3,1'-cyclopropane]-4-yl)oxypyrimidin-5-yl]-1H-imidazo[4,5-b]pyridine-2-one

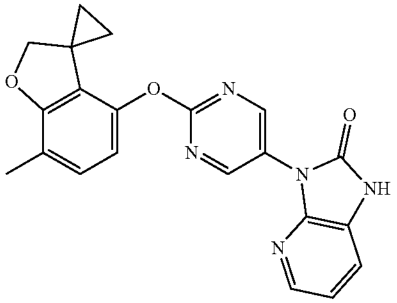

To a solution of 3-(2-chloropyrimidin-5-yl)-1H-imidazo[4,5-b]pyridin-2-one (Intermediate 73, 15 mg, 0.061 mmol) in N, N-Dimethylformamide (1 mL), 7-methyl-2H-spiro[1-benzofuran-3,1'-cyclopropan]-4-ol (Intermediate 156 WO2012/076877, 12 mg, 0.067 mmol) and potassium carbonate (13 mg, 0.092 mmol) were added, and the mixture was stirred for 20 hours at 90° C. The mixture was diluted with ethyl acetate (10 mL) and washed with water (10 mL) and brine (10 mL). The organic layer was dried over sodium sulphate, filtered and evaporated to dryness. The residue was purified by flash chromatography (Biotage System) on silica gel using a SFAR 10 g as column and cyclohexane/ethyl acetate from 60:40 to 0:100 as eluent. The obtained residue was further purified by reverse phase flash chromatography (Biotage system) on C18 stationary phase using a SNAP 12 g as column and water/acetonitrile from 70:30 to 10:90 as eluent affording the title compound 3-[2-(7-methylspiro[2H-benzofuran-3,1'-cyclopropane]-4-yl)oxypyrimidin-5-yl]-1H-imidazo[4,5-b]pyridin-2-one (3.80 mg) as a white solid.

LC/MS: QC_3_MIN: Rt=2.26 m/z 388 [M+H]+

The following compounds were prepared using analogous methods to the foregoing methodology, replacing 7-methyl-2H-spiro[1-benzofuran-3,1'-cyclopropan]-4-ol (Intermediate 156 WO2012/076877) with the appropriate phenol. Final products were purified by flash-chromatography (Silica cartridge using Cyclohexane/EtOAc or DCM/Methanol as eluent or C-18 cartridge using water/acetonitrile as eluent).

| Ex | Structure | Name | Phenol | NMR | LC-MS |
|---|---|---|---|---|---|
| 32 | 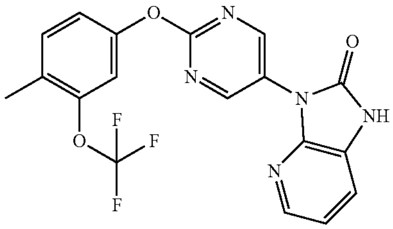 | 3-[2-[4-methyl-3-(trifluoromethoxy)phenoxy]pyrimidin-5-yl]-1H-imidazo[4,5-b]pyridin-2-one | 4-methyl-3-(trifluoromethoxy)phenol (Intermediate 116 WO2011/069951) | $^1$H-NMR (400 MHz; DMSO-d6): δ ppm 11.56 (s, 1H), 8.96 (s, 2H), 7.92 (dd, 1H), 7.45 (dd, 1H), 7.41 (dd, 1H), 7.34 (dt, 1H), 7.25 (dd, 1H), 7.10 (dd, 1H), 2.27 (s, 3H) | LC/MS: QC_3_MIN: Rt = 2.36 min m/z 404 [M + H]+ |
| 17 | 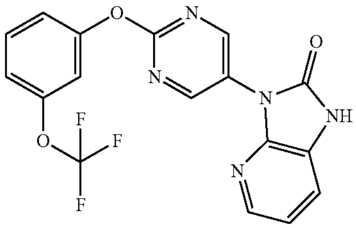 | 3-[2-[3-(trifluoromethoxy)phenoxy]pyrimidin-5-yl]-1H-imidazo[4,5-b]pyridin-2-one | 3-(trifluoromethoxy)phenol | — | LC/MS: QC_3_MIN: Rt = 2.29 min m/z 390 [M + H]+ |
| 33 | 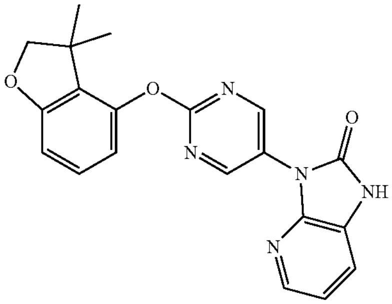 [SMILES: CC1(C)COc2cccc(Oc3ncc(-n4c(=O)[nH]c5cccnc54)cn3)c21] | 3-[2-[(3,3-dimethyl-2H-benzofuran-4-yl)oxy]pyrimidin-5-yl]-1H-imidazo[4,5-b]pyridin-2-one | 3,3-dimethyl-2H-benzofuran-4-ol (Intermediate 50 WO2012/076877) | $^1$H-NMR (400 MHz; DMSO-d6): δ ppm 11.56 (s, 1H), 8.97 (s, 2H), 7.93 (d, 1H), 7.41 (d, 1H), 7.08-7.18 (m, 2H), 6.67 (d, 2H), 4.19 (s, 2H), 1.24 (s, 6H) | LC/MS: QC_3_MIN: Rt = 2.20 min m/z 376 [M + H]+ |

Example 34

6-(6-spiro[2H-benzofuran-3,1'-cyclopropane]-4-yloxy-3-pyridyl)-2,4-dihydroimidazo[4,5-c]pyrazol-5-one

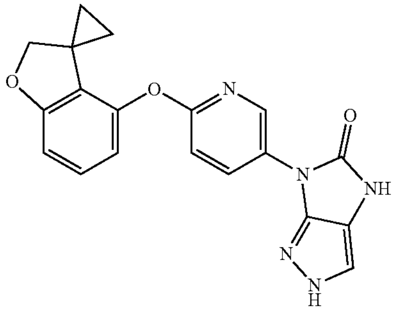 [SMILES: O=c1[nH]c2c[nH]nc2n1-c1ccc(Oc2cccc3c2C2(CC2)CO3)nc1]

2-[(4-methoxyphenyl)methyl]-6-(6-spiro[2H-benzofuran-3,1'-cyclopropane]-4-yloxy-3-pyridyl)-4H-imidazo[4,5-c]pyrazol-5-one (Intermediate 70, 8 mg, 0.017 mmol) was dissolved in trifluoroacetic acid (1 mL, 10 mmol) and the reaction mixture was stirred at 70° C. for 5 days. The solvent was evaporated and the residue was purified by reverse phase flash chromatography (Biotage System) on C18 stationary phase using a SFAR 12 g as column and water/acetonitrile from 80:20 to 75:25 as eluent, affording the title compound 6-(6-spiro[2H-benzofuran-3,1'-cyclopropane]-4-yloxy-3-pyridyl)-2,4-dihydroimidazo[4,5-c]pyrazol-5-one (1.2 mg) as a white solid.

LC/MS: QC_3_MIN: Rt=2.07 m/z 362 [M+H]+

Example 35

3-[6-(7-methylspiro[2H-benzofuran-3,1'-cyclopropane]-4-yl)oxy-3-pyridyl]-1H-imidazo[4,5-c]pyridin-2-one

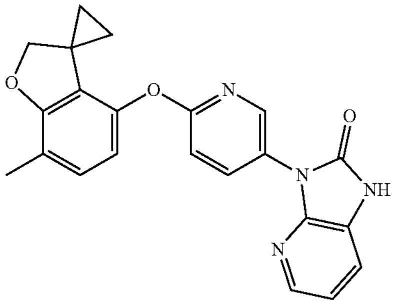 [SMILES: Cc1ccc(Oc2ccc(-n3c(=O)[nH]c4cccnc43)cn2)c2c1OCC21CC1]

A mixture of N3-[6-(7-methylspiro[2H-benzofuran-3,1'-cyclopropane]-4-yl)oxy-3-pyridyl]pyridine-3,4-diamine (Intermediate 80, 30 mg, 0.0832 mmol) and N, N-diisopropylethylamine (22.26 mg, 0.1722 mmol) (0.03 mL) in dichloromethane (1 mL) was cooled to 0° C. A solution of bis(trichloromethyl) carbonate (10 mg, 0.0337 mmol) in dichloromethane (0.5000 mL) was added dropwise and the reaction mixture was left to stir at 0° C. for 1 hour. The reaction mixture was diluted in EtOAc (15 mL) and washed with a 0.4 M aqueous solution of HCl (10 mL) and brine (15 mL). The organic layer was separated, dried over $Na_2SO_4$, filtered and concentrated under vacuum. The reaction mixture was concentrated under vacuum and then purified by Reverse Phase flash chromatography (Biotage System) on silica gel using a SNAP C-18 12 g column eluting Water: Acetonitrile from 95:5 to 40:60. The desired fractions were collected and concentrated under vacuum to afford 3-[6-(7-methylspiro[2H-benzofuran-3,1'-cyclopropane]-4-yl)oxy-3-pyridyl]-1H-imidazo[4,5-c]pyridin-2-one (19 mg) as an orange solid.

LC/MS: QC_3_MIN: Rt=1.85 m/z 387 [M+H]+

The following compounds were prepared using analogous methods to the foregoing methodology, replacing 4-methyl-N2-[6-(7-methylspiro[2H-benzofuran-3,1'-cyclopropane]-4-yl)oxy-3-pyridyl]pyridine-2,3-diamine (Intermediate 75) with the appropriate diamine. Reactions were carried out at temperatures ranging between 0° C. and room temperature. Final products were purified by flash-chromatography (Silica cartridge using Cyclohexane/EtOAc or DCM/Methanol as eluent or C-18 cartridge using water/acetonitrile as eluent).

| Ex | Structure | Name | Diamine | LC-MS |
|---|---|---|---|---|
| 36 | 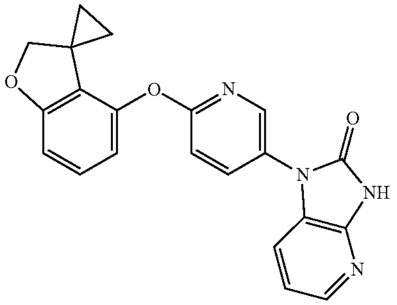 [SMILES: O=c1[nH]c2ncccc2n1-c1ccc(Oc2cccc3c2C2(CC2)CO3)nc1] | 1-(6-spiro[2H-benzofuran-3,1'-cyclopropane]-4-yloxy-3-pyridyl)-3H-imidazo[4,5-b]pyridin-2-one | N3-(6-spiro[2H-benzofuran-3,1'-cyclopropane]-4-yloxy-3-pyridyl) pyridine-2,3-diamine (Intermediate 81) | LC/MS: QC_3_MIN: Rt = 2.23 min m/z 373 [M + H]+ |

-continued

| Ex | Structure | Name | Diamine | LC-MS |
|---|---|---|---|---|
| 37 | 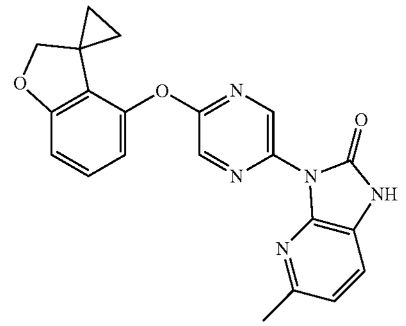 [SMILES: Cc1ccc2[nH]c(=O)n(-c3cnc(Oc4cccc5c4C4(CC4)CO5)cn3)c2n1] | 5-methyl-3-(5-spiro[2H-benzofuran-3,1'-cyclopropane]-4-yloxypyrazin-2-yl)-1H-imidazo[4,5-b]pyridin-2-one | 6-methyl-N2-(5-spiro[2H-benzofuran-3,1'-cyclopropane]-4-yloxypyrazin-2-yl)pyridine-2,3-diamine (Intermediate 82) | LC/MS: QC_3_MIN: Rt = 2.26 min m/z 388 [M + H]+ |
| 38 | 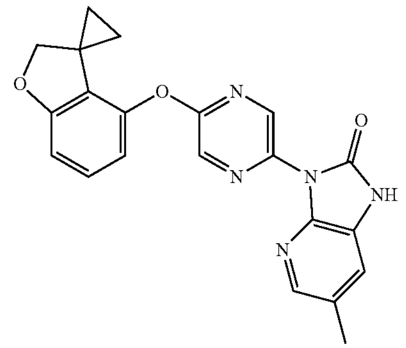 [SMILES: Cc1cnc2c(c1)[nH]c(=O)n2-c1cnc(Oc2cccc3c2C2(CC2)CO3)cn1] | 6-methyl-3-(5-spiro[2H-benzofuran-3,1'-cyclopropane]-4-yloxypyrazin-2-yl)-1H-imidazo[4,5-b]pyridin-2-one | 5-methyl-N2-(5-spiro[2H-benzofuran-3,1'-cyclopropane]-4-yloxypyrazin-2-yl)pyridine-2,3-diamine (Intermediate 83) | LC/MS: QC_3_MIN: Rt = 2.27 min m/z 388 [M + H]+ |

Example 39

3-[2-[(3,3,7-trimethyl-2H-benzofuran-4-yl)oxy]pyrimidin-5-yl]-1H-imidazo[4,5-b]pyridin-2-one

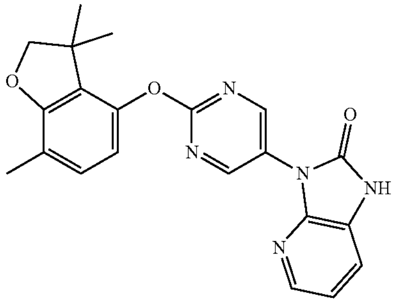 [SMILES: Cc1ccc(Oc2ncc(-n3c(=O)[nH]c4cccnc43)cn2)c2c1OCC2(C)C]

A mixture of 3-(2-chloropyrimidin-5-yl)-1H-imidazo[4,5-b]pyridin-2-one (Intermediate 73, 40 mg, 0.1615 mmol), 3,3,7-trimethyl-2H-benzofuran-4-ol (Intermediate 184 WO2012076877, 80 mg, 0.2244 mmol) and dipotassium carbonate (potassium carbonate) (48 mg, 0.3473 mmol) in dimethyl sulfoxide (5 mL) was stirred at 120° C. for 2 hours. The mixture was then diluted with water (20 mL) and extracted in EtOAc (15 mL×3). The combined organic layers were washed with brine (30 mL), separated, dried over $MgSO_4$, filtered and concentrated under vacuum. The crude residue was then purified by flash column chromatography (Biotage) using a MODUS 12 g silica column eluting 0-100% EtOAc in DCM. The desired fractions were collected and concentrated. This residue was then purified further by reverse phase column chromatography (Biotage) using a SNAP 30 g C-18 column eluting 5-95% acetonitrile in water. The desired fractions were collected and concentrated to give 3-[2-[(3,3,7-trimethyl-2H-benzofuran-4-yl)oxy]pyrimidin-5-yl]-1H-imidazo[4,5-b]pyridin-2-one (7 mg) as a white solid. LC/MS: QC_3_MIN: Rt=2.01 m/z 390 [M+H]+

Biological Examples

Biological Example 1: Measurement of Kv3 Channel Modulation

The ability of the compounds of the invention to modulate the voltage-gated potassium channel subtypes Kv3.4/Kv3.3/Kv3.2/Kv3.1 may be determined using the following assay. Analogous methods may be used to investigate the ability of the compounds of the invention to modulate other channel subtypes.

Cell Biology

To assess compound effects on human Kv3.3 channels (hKv3.3), a stable cell line expressing human Kv3.3 channels is created by transfecting Chinese Hamster Ovary (CHO)-K1 cells with a pBacMire_KCNC-3 vector. Cells are cultured in DMEM/F12 (Gibco) supplemented with 10% Foetal Bovine Serum (Gibco), 1× non-essential amino acids (Invitrogen) and geneticin (G418) 400 microg/mL. Cells are grown and maintained at 37° C. in a humidified environment containing 5% $CO_2$ in air.

To assess compound effects on human Kv3.2 channels (hKv3.2), a stable cell line expressing human Kv3.2 channels (hKv3.2) is created by transfecting CHO-K1 cells with a pCIH5-hKv3.2 vector. Cells are cultured in DMEM/F12 medium supplemented by 10% Foetal Bovine Serum, 1× non-essential amino acids (Invitrogen) and 500 ug/ml of Hygromycin-B (Invitrogen). Cells are grown and maintained at 37° C. in a humidified environment containing 5% $CO_2$ in air.

To Assess Compound Effects on Human Kv3.1 Channels (hKv3.1):

Human embryonic kidney (HEK)-hKv3.1 cell line is generated by transfecting HEK-293 cells with an expression vector with human Kv3.1 (NM_004976.4). Cells are cultured with MEM supplemented with 10% Heat-Inactivated FBS, 2 mM L-glutamine, 1% Penicillin-Streptomycin, and 0.6 mg/ml of Geneticin (G418). HEK-hKv3.1b cells were amplified in T175 cm2 flask at 37° C. with 5% $CO_2$, using MEM amplification medium, containing the G418 selection antibiotic (0.6 mg/ml). Cells were detached every 3-4 days, using DPBS to wash twice the flask, then TrypLE to dislodge the cells, and re-plated at a density of 2-4×$10^6$ cells/flask.

To Assess Compound Effects on Human Kv3.4 Channels (hKv3.4):

Human embryonic kidney (HEK)-hKv3.4 cell line is generated by transfecting HEK-293 cells with an expression vector with human Kv3.4 (NM_004978). Cells are cultured with MEM supplemented with 10% Heat-Inactivated FBS, 2 mM L-glutamine, 1% Penicillin-Streptomycin, and 0.6 mg/ml of Geneticin (G418). HEK-hKv3.4 cells were amplified in T175 cm2 flask at 37° C. with 5% $CO_2$, using MEM amplification medium, containing the G418 selection antibiotic (0.6 mg/ml). Cells were detached every 3-4 days, using DPBS to wash twice the flask, then TrypLE to dislodge the cells, and re-plated at a density of 4-8×$10^6$ cells/flask.

Cell Preparation for IonWorks Quattro™ Experiments

The day of the experiment, cells are removed from the incubator and the culture medium removed. Cells are washed with 5 ml of Dulbecco's PBS (DPBS) calcium and magnesium free and detached by the addition of 3 ml Versene (Invitrogen, Italy) followed by a brief incubation at 37° C. for 5 minutes. The flask is tapped to dislodge cells and 10 ml of DPBS containing calcium and magnesium is added to prepare a cell suspension. The cell suspension is then placed into a 15 ml centrifuge tube and centrifuged for 2 min at 1200 rpm. After centrifugation, the supernatant is removed and the cell pellet re-suspended in 4 ml of DPBS containing calcium and magnesium using a 5 ml pipette to break up the pellet. Cell suspension volume is then corrected to give a cell concentration for the assay of approximately 3 million cells per ml.

All the solutions added to the cells are pre-warmed to 37° C.

Electrophysiology

Experiments are conducted at r.t. using IonWorks Quattro™ planar array electrophysiology technology (Molecular Devices Corp.) with PatchPlate™ PPC. Stimulation protocols and data acquisition are carried out using a microcomputer (Dell Pentium 4). Planar electrode hole resistances (Rp) are determined by applying a 10 mV voltage step across each well. These measurements are performed before cell addition. After cell addition and seal formation, a seal test is performed by applying a voltage step from −80 mV to −70 mV for 160 ms. Following this, amphotericin-B solution is added to the intracellular face of the electrode to achieve intracellular access. Cells are held at −70 mV. Leak subtraction is conducted in all experiments by applying 50 ms hyperpolarizing (10 mV) prepulses to evoke leak currents followed by a 20 ms period at the holding potential before test pulses.

For hKv3.2 and hKv3.1, assays from the holding potential of −70 mV, a first test pulse at −15 mV was applied for 100 ms and after 100 ms at −70 mV a second pulse at +40 mV was applied for 50 ms. Cells were then maintained for 100 ms at −100 mV and another pulse from −70 mV to +40 mV (duration 50 ms) was applied to clamp later the voltage at −40 mV during 200 ms For hKv3.3 assays, from the holding potential of −70 mV, a first test pulse to 0 mV is applied for 500 ms and following a further 100 ms at −70 mV, a second pulse to 40 mV is applied for 200 ms. These longer test pulses are used to study inactivation of hKv3.3 channels. Test pulses protocol may be performed in the absence (pre-read) and presence (post-read) of the test compound. Pre- and post-reads may be separated by the compound addition followed by a 3 minute incubation.

For hKv3.4, assays from the holding potential of −70 mV, a first test pulse at −15 mV was applied for 100 ms and after 200 ms at −70 mV a second pulse was applied at 0 mV for 100 ms then after 200 ms at −70 mV a third pulse was applied at +40 mV during 200 ms.

Solutions and Drugs

The intracellular solution contains the following (in mM): K-gluconate 100, KCl 54, $MgCl_2$ 3.2, HEPES 5, adjusted to pH 7.3 with KOH. Amphotericin-B solution is prepared as 50 mg/ml stock solution in DMSO and diluted to a final working concentration of 0.1 mg/ml in intracellular solution. The external solution is Dulbecco's Phosphate Buffered Saline (DPBS) and contained the following (in mM): $CaCl_2$) 0.90, KCl 2.67, $KH_2PO_4$ 1.47, $MgCl.6H_2O$ 0.493, NaCl 136.9, $Na_3PO_4$ 8.06, with a pH of 7.4.

Compounds of use in the invention (or reference compounds such as N-cyclohexyl-N-[(7,8-dimethyl-2-oxo-1,2-dihydro-3-quinolinyl)methyl]-N'-phenylurea) are dissolved in dimethylsulfoxide (DMSO) at a stock concentration of 10 mM. These solutions are further diluted with DMSO using a Biomek FX (Beckman Coulter) in a 384 compound plate. Each dilution (1 μL) is transferred to another compound plate and external solution containing 0.05% pluronic acid (66 μL) is added. 3.5 μL from each plate containing a compound of the invention is added and incubated with the cells during the IonWorks Quattro™ experiment. The final assay dilution is 200 and the final compound concentrations are in the range 50 μM to 50 nM.

Data Analysis

The recordings are analysed and filtered using both seal resistance (>20 MΩ) and peak current amplitude (>500 pA at the voltage step of 40 mV) in the absence of compound to eliminate unsuitable cells from further analysis. For hKv3.2 and hKv3.1 assays, paired comparisons of evoked currents between pre- and post-drug additions measured for the −15 mV voltage step are used to determine the positive modulation effect of each compound. Kv3 channel-mediated outward currents are measured determined from the mean amplitude of the current over the final 10 ms of the −15 mV voltage pulse minus the mean baseline current at −70 mV over a 10 ms period just prior to the −15 mV step. These Kv3 channel currents following addition of the test compound are then compared with the currents recorded prior to compound addition. Data are normalised to the maximum effect of the reference compound (50 microM of N-cyclohexyl-N-[(7,8-dimethyl-2-oxo-1,2-dihydro-3-quinolinyl)methyl]-N'-phenylurea) and to the effect of a vehicle control (0.5% DMSO). The normalised data are analysed using ActivityBase or Excel software. The concentration of compound required to increase currents by 50% of the maximum increase produced by the reference compound ($EC_{50}$) is determined by fitting of the concentration-response data using a four parameter logistic function in ActivityBase. For hKv3.3 assays, paired comparisons of evoked currents between pre- and post-drug additions are measured for the 0 mV step, considering the peak current and the decay (inactivation) of the current over the duration of the 0 mv test pulse (500 ms).

N-cyclohexyl-N-[(7,8-dimethyl-2-oxo-1,2-dihydro-3-quinolinyl)methyl]-N'-phenylurea is obtained from ASINEX (Registry Number: 552311-06-5).

Results

The structures of a number of Reference Examples are provided in Table 1. Reference Example 1 has a hydantoin joined to a central pyridinyl ring, whilst Reference Examples 2 to 8 have various alternative heterocyclic groups joined to a central pyridinyl ring. Data for all Reference Examples 1 to 8 tested in the assay described above are also shown in Table 1.

Reference Example 1 was synthesised as outlined in WO2012/076877. Reference Examples 2 to 9 were synthesised using similar procedures to those disclosed herein.

TABLE 1

| Kv3.1 assay results | | |
|---|---|---|
| Reference Example | Kv3.1 $pEC_{50}$ | Kv3.1 max R % |
| RE1<br>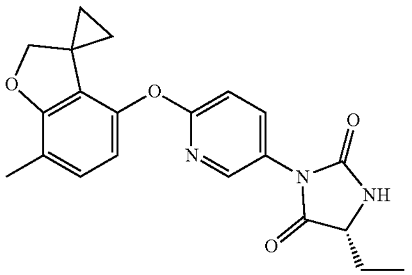 [SMILES: CC[C@H]1NC(=O)N(c2ccc(Oc3ccc(C)c4c3C3(CC3)CO4)nc2)C1=O]<br>(Example 62 of WO2012/076877) | 6.1 | 157 |
| RE2<br>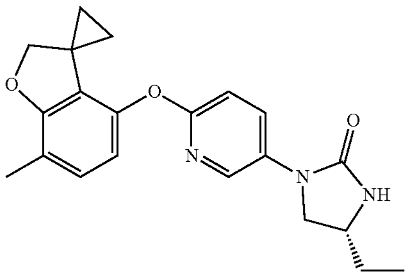 [SMILES: CC[C@@H]1CN(c2ccc(Oc3ccc(C)c4c3C3(CC3)CO4)nc2)C(=O)N1] | 4.7 | 92 |
| RE3<br>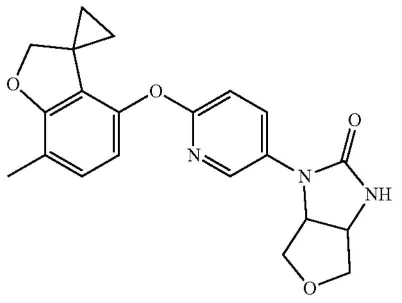 [SMILES: Cc1ccc(Oc2ccc(N3C(=O)NC4COCC43)cn2)c2c1OCC21CC1] | <4.3 | 30 |
| RE4<br>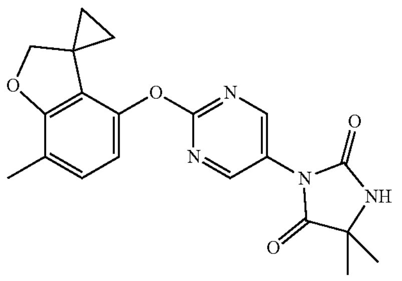 | 5.14 | 158 |

TABLE 1-continued

| Kv3.1 assay results | | |
|---|---|---|
| Reference Example | Kv3.1 $pEC_{50}$ | Kv3.1 max R % |
| (Example 58 of WO2012/076877) RE5 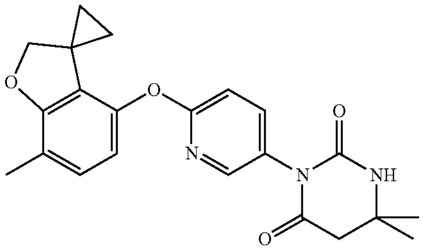 | 4.95 | 90 |
| RE6 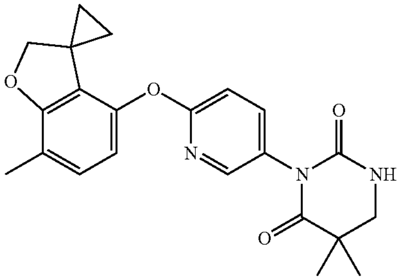 | 4.6 | 111 |
| RE7 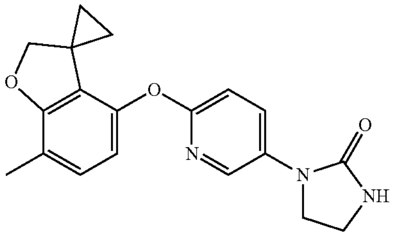 | 4.4 | 29 |
| RE8 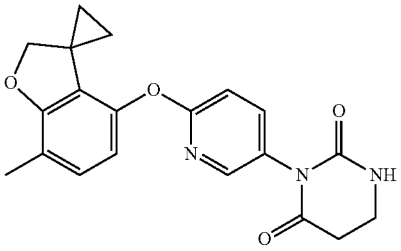 | 4.6 | 140 |

The data in Table 1 demonstrate that modification of the ethyl substituted hydantoin ring (Reference Example 1) to the corresponding ethyl substituted urea (Reference Example 2) or a fused oxygen containing 5,5-bicyclic urea (Reference Example 3) results in a significant reduction in $pEC_{50}$ and max R properties in the Kv3.1 assay. Similarly, modification of the hydantoin ring of Reference Example 4 to the corresponding dihydrouracil (Reference Example 5) and gem-dimethyl isomer (Reference Example 6) results in a significant reduction in $pEC_{50}$ and max R properties in the Kv3.1 assay. Removal of substitution of the urea or dihydrouracil leads to further reduction of potency (Reference Examples 7 and 8).

Data for all Example compounds tested in the assay described above are presented in Table 2.

TABLE 2

| Kv3.1 assay results | | |
|---|---|---|
| Example Compound | Kv3.1 $pEC_{50}$ | Kv3.1 max R % |
| Example 1 | 6.7 | 148 |
| Example 2 | 6.8 | 83 |
| Example 3 | 7.0 | 197 |
| Example 4 | 5.9 | 111 |
| Example 5 | 6.5 | 132 |
| Example 6 | 5.7 | 221 |
| Example 7 | 6.3 (n = 4) | 89 |
| | 6.4 (n = 2) | 96 |
| Example 8 | 6.7 | 204 |
| Example 9 | 5.9 | 147 |
| Example 10 | 5.7 | 94 |

TABLE 2-continued

| Kv3.1 assay results | | |
|---|---|---|
| Example Compound | Kv3.1 $pEC_{50}$ | Kv3.1 max R % |
| Example 11 | 6.5 | 205 |
| Example 12 | 6.5 | 164 |
| Example 13 | 6.7 | 194 |
| Example 14 | 6.0 | 124 |
| Example 15 | 6.0 | 201 |
| Example 16 | 5.5 | 124 |
| Example 17 | 5.9 (n = 14) | 103 |
| | 6.0 (n = 6) | 125 |
| Example 18 | 6.6 | 148 |
| Example 19 | 6.5 | 99 |
| Example 20 | 6.1 (n = 6) | 145 |
| | 6.2 (n = 4) | 155 |
| Example 21 | 5.0 | 96 |
| Example 22 | 6.3 | 166 |
| Example 23 | 5.0 (n = 4) | 101 |
| | 5.1 (n = 2) | 107 |
| Example 24 | 6.0 | 144 |
| Example 25 | 6.5 | 190 |
| Example 26 | 7.3 | 135 |
| Example 27 | 5.8 (n = 6) | 134 |
| | 5.9 (n = 4) | 138 |
| Example 28 | 5.4 | 140 |
| Example 29 | 6.8 | 117 |
| Example 30 | 6.9 | 123 |
| Example 31 | 6.7 | 217 |
| Example 32 | 5.8 | 174 |
| Example 33 | 6.1 | 194 |
| Example 34 | 5.0 (n = 4) | 128 |
| | 5.0 (n = 2) | 131 |
| Example 35 | 6.0 | 225 |
| Example 36 | 6.2 | 113 |
| Example 37 | 6.9 | 124 |
| Example 38 | 6.7 | 122 |
| Example 39 | 5.8 | 215 |

* Data are rounded to one decimal place

The data in Table 2 show that a 5-membered urea fused to a 5- or 6-membered heteroaromatic ring results in compounds displaying good $pEC_{50}$ properties in the Kv3.1 assay.

Data for Reference Examples comprising a 5-membered urea fused to a 3-pyridinyl ring, or a 6-membered urea fused to a 6-membered heterocyclic ring and their corresponding Example compounds are presented in Table 3.

TABLE 3

| Kv3.1 assay results | | | |
|---|---|---|---|
| Reference Example | Kv3.1 $pEC_{50}$ | Example | Kv3.1 $PEC_{50}$ |
| RE9 | <4.3 | Example 33 | 6.2 |
| 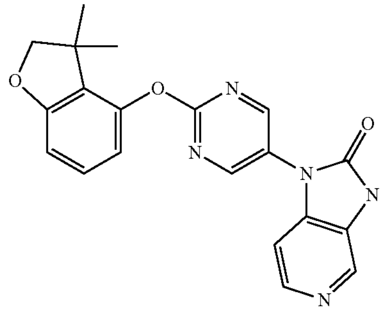 [SMILES: CC1(C)COc2cccc(Oc3ncc(-n4c(=O)[nH]c5cnccc54)cn3)c21] | | 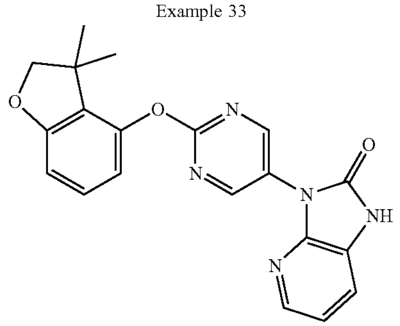 | |
| | | Example 23 | 5.1 |
| | | 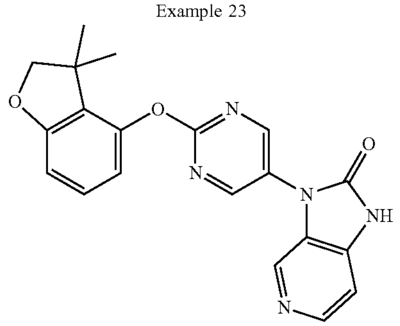 | |
| RE10 | 5.6 | Example 7 | 6.4 |
| 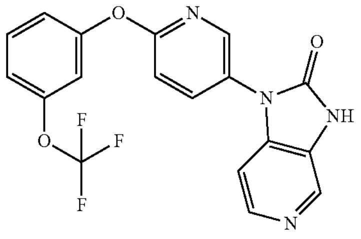 [SMILES: O=c1[nH]c2cnccc2n1-c1ccc(Oc2cccc(OC(F)(F)F)c2)nc1] | | 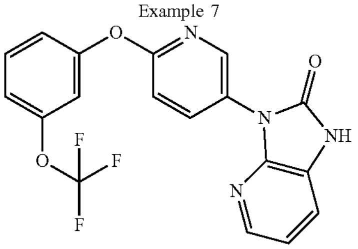 | |

TABLE 3-continued

| Kv3.1 assay results | | | |
|---|---|---|---|
| Reference Example | Kv3.1 $pEC_{50}$ | Example | Kv3.1 $PEC_{50}$ |
| RE11 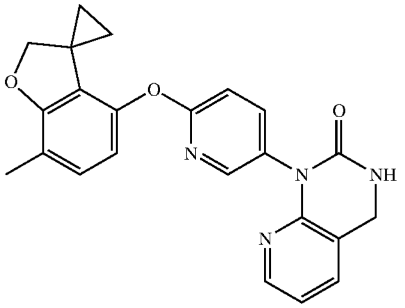 | 5.7 | Example 1 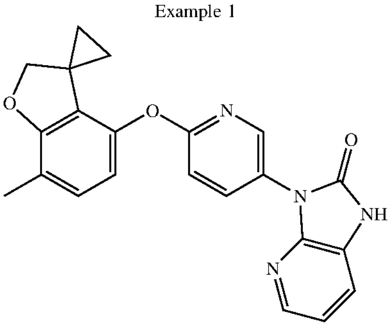 | 6.7 |
| | | Example 36 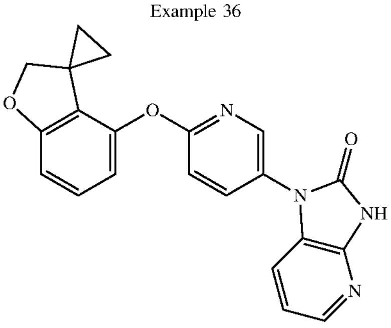 | 6.2 |

* Data are rounded to one decimal place

The data in Table 3 show that Reference Example 9 comprising a 5-membered urea fused to a 3-pyridinyl group is less potent than its corresponding 1-pyridinyl compound (Examples 33) and 2-pyiridinyl compound (Example 23). Reference Example 10 comprising a 5-membered urea fused to a 3-pyridinyl group is less potent than its corresponding 1-pyridinyl compound (Examples 7). Reference Example 11 comprising a 6-membered urea fused to a 1-pyiridinyl group is less potent than its corresponding 5-membered urea fused to a 1-pyridinyl group (Example 1) and 5-membered urea fused to a 4-pyridinyl group (Example 36).

A secondary analysis of the data from the hKv3.1, hKv3.2 and hKv3.3 assays described in Biological Example 1 may be used to investigate the effect of the compounds on rate of rise of the current from the start of the depolarising voltage pulses. The magnitude of the effect of a compound can be determined from the time constant ($Tau_{act}$) obtained from a non-linear fit, using the equation given below, of the rise in Kv3.1, Kv3.2 and Kv3.3 currents following the start of the −15 mV depolarising voltage pulse.

$$Y=(Y0-Y\max)^{*}\exp(-K^{*}X)+Y\max$$

where:

Y0 is the current value at the start of the depolarising voltage pulse;

Ymax is the plateau current;

K is the rate constant, and $Tau_{act}$ is the activation time constant, which is the reciprocal of K.

Similarly, the effect of the compounds on the time taken for Kv3.1, Kv3.2 or Kv3.3 currents to decay on closing of the channels at the end of the −15 mV depolarising voltage pulses can also be investigated. In this latter case, the magnitude of the effect of a compound on channel closing can be determined from the time constant ($Tau_{deact}$) of a non-linear fit of the decay of the current ("tail current") immediately following the end of the depolarising voltage pulse.

Kv3.1, Kv3.2 and Kv3.3 channels must activate and deactivate very rapidly in order to allow neurons to fire actions potentials at high frequency (Rudy et al., 2001). Slowing of activation is likely to delay the onset of action potential repolarisation; slowing of deactivation could lead to hyperpolarising currents that reduce the excitability of the neuron and delay the time before the neuron can fire a further action potential. Together these two slowing effects on channel activation and deactivation are likely to lead to a reduction rather than a facilitation of the neurons ability to fire at high frequencies. Thus compounds that have this slowing effect on the Kv3.1 and/or Kv3.2, and/or Kv3.3 channels will effectively behave as negative modulators of the channels, leading to a slowing of neuronal firing. This latter effect has been shown for certain of the compounds disclosed in WO2011/069951, where marked increases in $Tau_{act}$ can be observed from recordings made from "fast-firing" interneurons in the cortex of rat brain, using electro-physiological techniques, in vitro. The addition of the relevant compounds reduces the ability of the neurons to fire in response to trains of depolarising pulses at 300 Hz.

Therefore, although certain compounds may be identified act as positive modulators in the recombinant cell assay of Biological Example 1, those compounds which markedly increase the value of $Tau_{act}$ can reduce the ability of neurons in native tissues to fire at high frequency.

Biological Example 2: Determination of In Vivo Pharmacokinetic Parameters

Materials and Methods

Adult male rats (Charles River, Italy) are dosed with test compound orally at 1 mg/kg (5 ml/kg, in 5% v/v DMSO, 0.5% w/v HPMC in water) and intravenously at 0.5 mg/kg (2 ml/kg, in 5% v/v DMSO 40% w/v PEG400 in saline). After oral administration, blood samples are collected under deep Isofluorane anesthesia from the portal vein and heart of each rat (1 rat per time point). After intravenous administration, serial blood samples are collected from the lateral tail vein of each rat. Blood and brain samples are collected at a single timepoint of 0.5 h after dose administration for these animals. In all cases, blood samples are collected into potassium EDTA tubes.

A further group of rats (n=1 per test compound) receive a single intravenous administration of the PgP transport inhibitor, Elacridar (3 mg/kg) shortly before the oral administration of the test compound at 1 mg/kg, as above.

Blood and brain samples can be assayed for test compound concentration using a method based on protein precipitation with acetonitrile followed by HPLC/MS-MS analysis with an optimized analytical method.

Analysis

The concentrations of test compound in blood (expressed as ng/ml) and brain (expressed as ng/g) at the different time points following either oral or intravenous dosing are analysed using a non-compartmental pharmacokinetic model using WinNonLin Professional version 4.1. The following parameters are derived:

Intravenous dosing: Maximum concentration over time (Cmax), integrated concentration over time (AUC), clearance (Clb), volume of distribution (Vss), half-life (t1/2) and Brain/Heart Blood conc @0.5 hr.

Oral dosing: Cmax, time of maximum concentration (Tmax), AUC, bioavailability (F %), fraction absorbed (Fa %), blood to brain ratio (AUC B/B), and Fold-change in AUC B/B in the presence of Elacridar.

TABLE 4

Test compound AUC and concentrations

| Example | AUC B/B (brain/blood) ratio | Brain/Heart Blood conc @0.5 hr |
|---|---|---|
| 8 | <0.1 | <0.1 |
| 13 | 0.12 | 0.13 |
| 17 | 0.45 | 0.76 |
| 24 | 0.29 | 0.33 |
| 26 | <0.1 | <0.1 |
| 33 | 0.65 | 0.63 |

Biological Example 3: Further Determination of In Vivo Pharmacokinetic Parameters Determination of Blood and Brain Tissue Binding Sprague Dawley rat whole blood, collected on the week of the experiment using K3-EDTA as an anti-coagulant, is diluted with isotonic phosphate buffer 1:1 (v/v). Sprague Dawley rat whole brain, stored frozen at −20° C., is thawed and homogenised in artificial cerebrospinal fluid (CSF) 1:2 (w/v).

An appropriate amount of test compound is dissolved in DMSO to give a 10 millimolar solution. Further dilutions, to obtain a 166.7 micromolar working solution are then prepared using 50% acetonitrile in MilliQ water. This working solution is used to spike the blood to obtain a final concentration of 0.5 micromolar in whole blood. Similarly, the working solution is used to spike brain samples to obtain a final concentration of 5 micromolar in whole brain. From these spiked blood and brain preparations, control samples (n=3), are immediately extracted and used to calculate the initial recovery of the test items.

150 microL of compound-free buffer (isotonic phosphate buffer for blood or artificial CSF buffer for brain) is dispensed in one half-well and 150 microL of spiked matrix (blood or brain) is loaded in the other half-well, with the two halves separated by a semi-permeable membrane. After an equilibration period of 5 h at 37° C., 50 microL of dialysed matrix (blood or brain) is added to 50 microL of corresponding compound-free buffer, and vice-versa for buffer, such that the volume of buffer to matrix (blood or brain) remains the same. Samples are then extracted by protein precipitation with 300 microL of acetonitrile containing rolipram (control for positive ionization mode) or diclofenac (control for negative ionization mode) as internal standards and centrifuged for 10 min at 3000 rpm. Supernatants are collected (100 microL), diluted with 27% AcN in MilliQ water (200 microL) and then injected into an HPLC-MS/MS or UPLC-MS/MS system to determine the concentration of test compound present.

Blood and brain tissue binding are then determined using the following formulas:

$$Afu = \text{Buffer}/\text{Blood} \text{ or } Afu = CSF/\text{Brain}$$

where Afu=apparent fraction unbound; Buffer=analyte/internal standard ratio determined in the buffer compartment; Blood=analyte/internal standard ratio determined in the blood compartment; Brain=analyte/internal standard ratio determined in the brain compartment.

$$Fucr = \frac{1/D}{[(1/Afu - 1) + 1/D]}$$

where: fucr=Fraction unbound corrected; D=matrix dilution factor (D=2 for blood and D=3 for brain).

then:

$$\% \text{ Binding} = (1 - fucr) \times 100$$

$$\% \text{ Unbound} = 100 - \% \text{ Bound}$$

In Vitro Metabolic Stability Study in Hepatocytes

The objective of this study was to determine metabolic stability of test items in rat and human liver microsomes. Verapamil and dextromethorphan were used as positive controls for microsomal incubation.

Incubation medium was prepared by combining 11.2 mL of potassium phosphate monobasic and 38.8 mL of potassium phosphate dibasic, diluted to 1 L with water. Cryopreserved microsomes were thawed and kept on ice until use. Microsomes were then diluted in incubation to a protein concentration of 0.56 mg/mL. Cells were centrifuged, re-suspended in medium and counted by means of a haemocytometer. Cell viability was measured using the Trypan Blue exclusion test.

NADPH regenerating system solution was prepared by dissolving 1.7 mg of NADP, 7.8 mg of G6P and 6 units of G6P-Dehydrogenase in 1 mL of 2% sodium bicarbonate solution (prepared by dissolving 20 g of $NaHCO_3$ in 1 L of water).

Test compounds were separately dissolved in DMF to obtain 10 mM stock solutions that were further diluted in water/acetonitrile 50/50 (v/v) to obtain the corresponding 50 μM working solutions. Verapamil and dextromethorphan were dissolved in DMF in order to obtain a 10 mM verapamil solution and 10 mM dextromethorphan solution. These solutions were then diluted in the incubation medium in order to obtain a 50 μM verapamil working solution and a 50 μM dextromethorphan working solution.

800 μL-aliquots of NADPH regenerating system were pre-warmed at 37° C. for 5 minutes. 5 μL of 50 UM test compounds, verapamil or dextromethorphan were added to 445 μL of the 0.56 mg/mL microsomes solution and the incubation mixture was pre-warmed in a 96 deep well 2 mL plate (incubation plate) at 37° C. for 5 minutes. The incubation reactions were initiated by adding 50 μL of pre-warmed NADPH regenerating system to the incubation mixtures. 50 μL aliquots were taken from incubation mixtures at: 0, 3, 6, 9, 15, and 30 minutes and the reactions were stopped by adding 100 μL of aceronitrile with the corresponding internal standard. Samples were then diluted with 120 μL of water (final organic solvent percentage at 37%) and centrifuged at 3000 rpm for 10 minutes, prior the LC-MS/MS analysis.

Metabolic stability was calculated from the peak area ratio of the remaining test compound with internal standard versus time. The intrinsic clearance (CLint) was determined from the first order elimination constant k ($min^{-1}$) (obtained from GraphPad by plotting the natural logarithm of the peak area ratio of the remaining test item with internal standard versus time), using the actual volume of the incubation V (mL), the amount of hepatocytes in the incubation M (million cells) and the hepatocellularity number per a liver Hn (120 for human).

$$CLint = k * \frac{V}{M} * \frac{Hn \times 10^6 \text{cells}}{\text{g liver}}$$

Values for CLint were expressed as mL/min/g liver as shown in Table 5:

TABLE 5

Test compound pharmacokinetic parameters

| Example | Kv3.1 pEC50 | % FU Blood | % FU Brain | Cli rat (mL/min/g) | Cli human (mL/min/g) |
|---|---|---|---|---|---|
| RE12 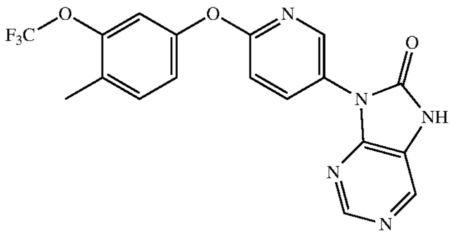 (Example 25 of WO2021214090) | 5.2* | 0.7 | 0.6 | 1.5 | 1.7 |
| RE13 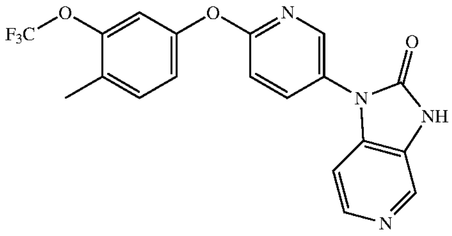 (Example 47 of WO2021214090) | 5.6** | 1.3 | 0.5 | 1.3 | 0.6 |
| Example 4 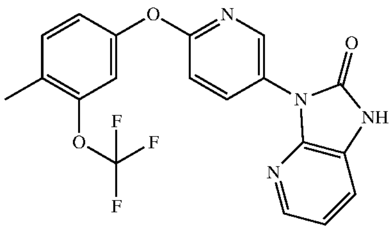 [SMILES: Cc1ccc(Oc2ccc(-n3c(=O)[nH]c4cccnc43)cn2)cc1OC(F)(F)F] | 5.9 | 0.2 | 0.3 | 0.9 | 0.7 |

TABLE 5-continued

| Test compound pharmacokinetic parameters | | | | | |
|---|---|---|---|---|---|
| Example | Kv3.1 pEC50 | % FU Blood | % FU Brain | Cli rat (mL/min/g) | Cli human (mL/min/g) |
| Example 7 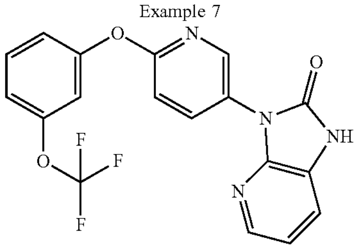 | 6.4 | — | — | — | — |
| Example 32 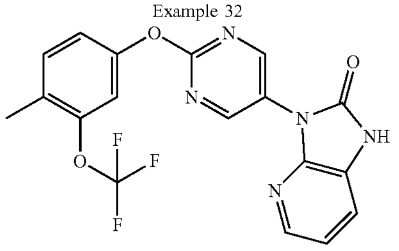 | 5.8 | 1.0 | 0.6 | 0.9 | 0.8 |
| Example 17 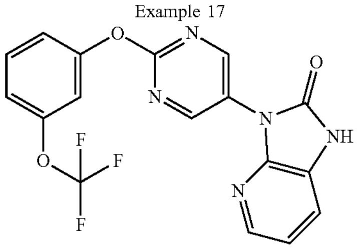 | 6.0 | 1.6 | 1.6 | <0.5 | <0.5 |

*Based on $EC_{50}$ value of 5.9 as reported in WO2021214090. Reference Example 12 was prepared by analogous methods to the Examples-LC/MS: QC_3_MIN: Rt = 2.04 min m/z 404 $[M + H]^+$.
**Based on $EC_{50}$ value of 2.4 as reported in WO2021214090. Reference Example 13 was prepared by analogous methods to the Examples-LC/MS: QC_3_MIN: Rt = 2.07 min m/z 403 $[M + H]^+$.

The data in Table 5 show that Example 17 demonstrates a plurality of desirable properties—while maintaining good potency ($pEC_{50}$ 6.0), Example 17 also has good fraction unbound (1.6% in blood and brain) and good clearance (Cli <0.5 in humans and rats). These properties compare favourably with compounds such as Examples 4 and 32, and Reference Examples 12 and 13 (Example 25 and 27 of WO2021214090).

Formulation Example 1-Tablet:

A compound of formula (I), or a pharmaceutically acceptable salt and/or solvate and/or derivative thereof, can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Formulation Example 2-Capsule:

A compound of formula (I), or a pharmaceutically acceptable salt and/or solvate and/or derivative thereof, can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Additional Animal Models

Patent applications WO2011/069951, WO2012/076877, WO2012/168710, WO2013/175215 WO2013/182851, WO2013/083994, WO2013/182850, WO2017/103604, WO2018/020263, WO2018/109484 and WO2020/079422 (all incorporated by reference) demonstrate the activity of compounds which are modulators of Kv3.1 and Kv3.2 in animal models of seizure, hyperactivity, sleep disorders, psychosis, hearing disorders, bipolar disorders and pain.

Patent application WO2013/175211 (incorporated by reference) demonstrates the efficacy of a compound which is a modulator of Kv3.1 and Kv3.2 in a model of acute noise-induced hearing loss in the chinchilla, and also evaluates the efficacy of the compound in a model of central auditory processing deficit and in a model of tinnitus.

Throughout the specification and the claims which follow, unless the context requires otherwise, the word ‘comprise’, and variations such as ‘comprises’ and ‘comprising’, will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims which follow.

Clauses of the Invention

Clause 1. A compound of formula (I):

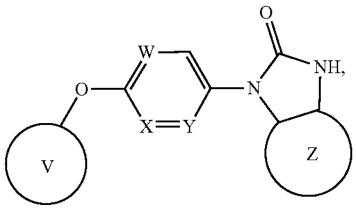

wherein:

V is group (Va), group (Vb) or group (Vc);

wherein group (Va) and group (Vb) are:

(Va)

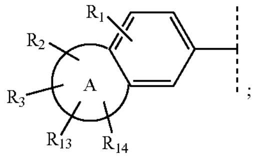

(Vb)

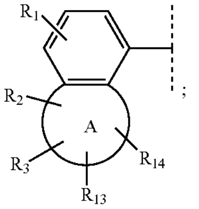

wherein:

$R_1$ is H, $C_{1-4}$alkyl, halo, halo$C_{1-4}$alkyl, CN, $C_{1-4}$alkoxy, or halo$C_{1-4}$alkoxy; $R_2$ is H, $C_{1-4}$alkyl, $C_{3-5}$ spiro carbocyclyl, halo$C_{1-4}$alkyl or halo;

$R_3$ is H, $C_{1-4}$alkyl, halo$C_{1-4}$alkyl, halo; or $R_3$ is absent;

$R_{13}$ is H, $C_{1-4}$alkyl, halo$C_{1-4}$alkyl, halo; or $R_{13}$ is absent;

$R_{14}$ is H, $C_{1-4}$alkyl, halo$C_{1-4}$alkyl, halo; or $R_{14}$ is absent;

A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;

wherein $R_2$ and $R_3$ may be attached to the same or a different ring atom; $R_2$ may be attached to a fused ring atom; and wherein $R_{13}$ and $R_{14}$ may be attached to the same or a different ring atom;

wherein group (Vc) is:

(Vc)

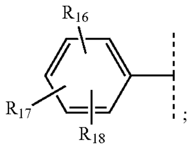

wherein:

$R_{16}$ is halo, $C_{1-4}$alkyl, $C_{1-4}$alkoxy, halo$C_{1-4}$alkyl, halo$C_{1-4}$ alkoxy or CN;

$R_{17}$ is H, halo, CN, $C_{1-4}$alkyl, $C_{1-4}$alkoxy or halo$C_{1-4}$ alkoxy;

$R_{18}$ is H, halo, CN, $C_{1-4}$alkyl or $C_{1-4}$alkoxy;

W is N or CH;

X is N or CH;

Y is N or CH;

wherein at least one of W, X and Y is CH, and when one of X and Y is N, the other is CH;

Z is a 5-membered heteroaryl comprising one or two nitrogen atoms, and wherein one of the nitrogen atoms and one of the carbon atoms may be independently optionally substituted by methyl; or Z is a 6-membered heteroaryl comprising one or two nitrogen atoms, wherein one of the carbon atoms may be optionally substituted by methyl; and provided that Z is not

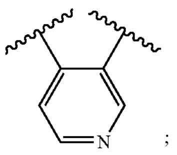 [SMILES: *c1ccncc1*]

or a salt and/or solvate and/or derivative thereof.

Clause 2. A compound of formula (I):

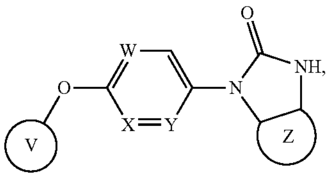

wherein:

V is group (Va), group (Vb) or group (Vc);

wherein group (Va) and group (Vb) are:

(Va)

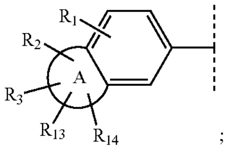

-continued (Vb)

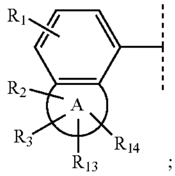
;

wherein:

$R_1$ is H, $C_{1-4}$alkyl, halo, halo$C_{1-4}$alkyl, CN, $C_{1-4}$alkoxy, or halo$C_{1-4}$alkoxy;

$R_2$ is H, $C_{1-4}$alkyl, $C_{3-5}$ spiro carbocyclyl, halo$C_{1-4}$alkyl or halo;

$R_3$ is H, $C_{1-4}$alkyl, halo$C_{1-4}$alkyl, halo; or $R_3$ is absent;

$R_{13}$ is H, $C_{1-4}$alkyl, halo$C_{1-4}$alkyl, halo; or $R_{13}$ is absent;

$R_{14}$ is H, $C_{1-4}$alkyl, halo$C_{1-4}$alkyl, halo; or $R_{14}$ is absent;

A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;

wherein $R_2$ and $R_3$ may be attached to the same or a different ring atom; $R_2$ may be attached to a fused ring atom; and wherein $R_{13}$ and $R_{14}$ may be attached to the same or a different ring atom;

wherein group (Vc) is:

(Vc)

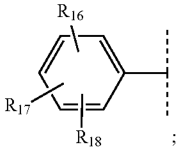
;

wherein:

$R_{16}$ is halo, $C_{1-4}$alkyl, $C_{1-4}$alkoxy, halo$C_{1-4}$alkyl, halo$C_{1-4}$ alkoxy or CN;

$R_{17}$ is H, halo, CN, $C_{1-4}$alkyl, $C_{1-4}$alkoxy or halo$C_{1-4}$ alkoxy;

$R_{18}$ is H, halo, CN, $C_{1-4}$alkyl or $C_{1-4}$alkoxy;

W is N or CH;

X is N or CH;

Y is N or CH;

wherein at least one of W, X and Y is CH, and when one of X and Y is N, the other is CH;

Z is a 5-membered heteroaryl comprising one or two nitrogen atoms, and wherein one of the nitrogen atoms and one of the carbon atoms may be independently optionally substituted by methyl; or Z is a 6-membered heteroaryl comprising one or two nitrogen atoms, wherein one of the carbon atoms may be optionally substituted by methyl; and provided that Z is not

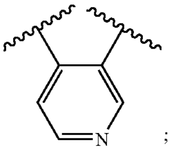 [SMILES: *c1ccncc1*]
;

or a pharmaceutically acceptable salt and/or solvate and/or derivative thereof.

Clause 3. The compound or pharmaceutically acceptable salt and/or solvate thereof according to clause 2.

Clause 4. The compound or solvate thereof according to clause 3.

Clause 5. The compound or a pharmaceutically acceptable salt thereof according to clause 2.

Clause 6. The compound according to clause 1 or 2.

Clause 7. The compound, pharmaceutically acceptable salt thereof, solvate thereof, and/or derivative thereof according to any one of clauses 1 to 6, wherein V is group (Va).

Clause 8. The compound, pharmaceutically acceptable salt thereof, solvate thereof, and/or derivative thereof according to any one of clauses 1 to 6, wherein V is group (Vb).

Clause 9. The compound, pharmaceutically acceptable salt thereof, solvate thereof, and/or derivative thereof according to clause 8, wherein (Vb) is:

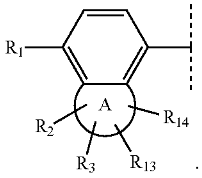
.

Clause 10. The compound, pharmaceutically acceptable salt thereof, solvate thereof, and/or derivative thereof according to any one of clauses 1 to 9, wherein $R_1$ is H, $C_{1-4}$alkyl, halo, halo$C_{1-4}$alkyl or CN, in particular $C_{1-4}$alkyl such as methyl.

Clause 11. The compound, pharmaceutically acceptable salt thereof, solvate thereof, and/or derivative thereof according to clause 10, wherein $R_1$ is H.

Clause 12. The compound, pharmaceutically acceptable salt thereof, solvate thereof, and/or derivative thereof according to clause 10, wherein $R_1$ is methyl.

Clause 13. The compound, pharmaceutically acceptable salt thereof, solvate thereof, and/or derivative thereof according to any one of clauses 1 to 12, wherein ring A is selected from the group consisting of:

1

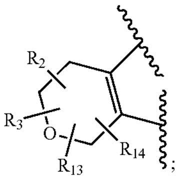
;

2

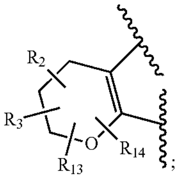
;

-continued
3
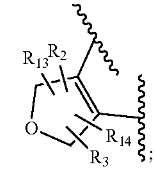
;
4
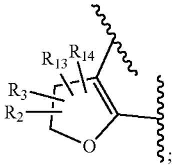
;
5
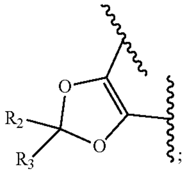
;
6
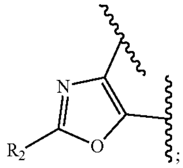
;
7
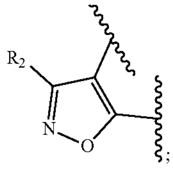
;
8
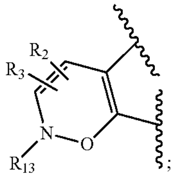
;
9
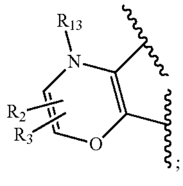
;
10
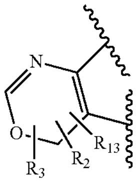
; and
-continued
11
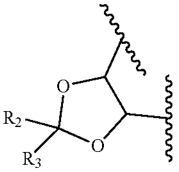
wherein
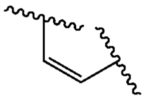 [SMILES: */C=C\*]
denotes a point at which ring A is fused to the phenyl ring.
Clause 14. The compound, pharmaceutically acceptable salt thereof, solvate thereof, and/or derivative thereof according to clause 13, wherein ring A is selected from the group consisting of:
1
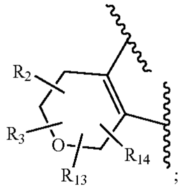
;
2
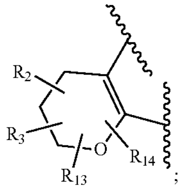
;
3
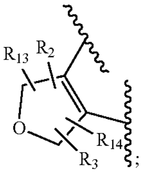
;
4
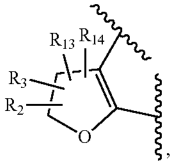
, and
11
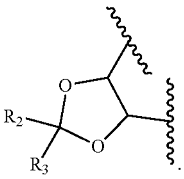
.

Clause 15. The compound, pharmaceutically acceptable salt thereof, solvate thereof, and/or derivative thereof according to clause 14, wherein ring A is:

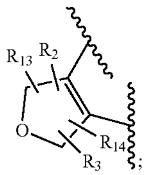

3

; or

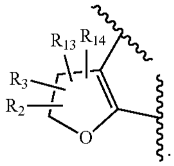

4

.

Clause 16. The compound, pharmaceutically acceptable salt thereof, solvate thereof, and/or derivative thereof according to any one of clauses 1 to 15, wherein $R_2$ is H, $C_{1-4}$alkyl, $C_{3-5}$spiro carbocyclyl or halo; in particular $C_{1-4}$ alkyl or $C_{3-5}$spiro carbocyclyl.

Clause 17. The compound, pharmaceutically acceptable salt thereof, solvate thereof, and/or derivative thereof according to clause 16, wherein $R_2$ is $C_3$ spiro carbocycle.

Clause 18. The compound, pharmaceutically acceptable salt thereof, solvate thereof, and/or derivative thereof according to clause 17, wherein $R_2$ is methyl or halo e.g. fluoro.

Clause 19. The compound, pharmaceutically acceptable salt thereof, solvate thereof, and/or derivative thereof according to clause 18, wherein $R_2$ is methyl.

Clause 20. The compound, pharmaceutically acceptable salt thereof, solvate thereof, and/or derivative thereof according to any one of clauses 1 to 19, wherein $R_3$ is H, $C_{1-4}$alkyl, halo$C_{1-4}$alkyl or halo.

Clause 21. The compound, pharmaceutically acceptable salt thereof, solvate thereof, and/or derivative thereof according to clause 20, wherein $R_3$ is methyl or halo e.g. fluoro.

Clause 22. The compound, pharmaceutically acceptable salt thereof, solvate thereof, and/or derivative thereof according to clause 21, wherein $R_3$ is methyl.

Clause 23. The compound, pharmaceutically acceptable salt thereof, solvate thereof, and/or derivative thereof according to any one of clauses 1 to 22, wherein $R_{13}$ is H or is absent and is suitably absent.

Clause 24. The compound, pharmaceutically acceptable salt thereof, solvate thereof, and/or derivative thereof according to any one of clauses 1 to 23, wherein $R_{14}$ is H or is absent and is suitably absent.

Clause 25. The compound, pharmaceutically acceptable salt thereof, solvate thereof, and/or derivative thereof according to any one of clauses 1 to 6, wherein V is group (Vc).

Clause 26. The compound, pharmaceutically acceptable salt thereof, solvate thereof, and/or derivative thereof according to any one of clauses 1 to 6 or 25, wherein $R_{16}$ is $C_{1-4}$alkyl, $C_{1-4}$alkoxy, halo$C_{1-4}$alkyl, halo$C_{1-4}$alkoxy or CN.

Clause 27. The compound, pharmaceutically acceptable salt thereof, solvate thereof, and/or derivative thereof according to clause 26, wherein $R_{16}$ is methyl, ethyl, propyl, butyl, cyclopropyl, chloro, fluoro, methoxy, ethoxy, propoxy, trifluoromethyl, trifluoromethoxy or CN.

Clause 28. The compound, pharmaceutically acceptable salt thereof, solvate thereof, and/or derivative thereof according to clause 27, wherein $R_{16}$ is trifluoromethoxy or methoxy.

Clause 29. The compound, pharmaceutically acceptable salt thereof, solvate thereof, and/or derivative thereof according to any one of clauses 1 to 6 or 25 to 28, wherein $R_{16}$ is at the meta-position.

Clause 30. The compound, pharmaceutically acceptable salt thereof, solvate thereof, and/or derivative thereof according to any one of clauses 1 to 6 or 25 to 29, wherein $R_{17}$ is H, halo, CN, $C_{1-4}$alkyl or $C_{1-4}$alkoxy.

Clause 31. The compound, pharmaceutically acceptable salt thereof, solvate thereof, and/or derivative thereof according to clause 30, wherein $R_{17}$ is H.

Clause 32. The compound, pharmaceutically acceptable salt thereof, solvate thereof, and/or derivative thereof according to clause 31, wherein $R_{17}$ is methyl, ethyl, propyl, butyl, cyclopropyl, chloro, fluoro, methoxy, ethoxy, propoxy, trifluoromethoxy or CN.

Clause 33. The compound, pharmaceutically acceptable salt thereof, solvate thereof, and/or derivative thereof according to clause 32, wherein $R_{17}$ is methyl or CN.

Clause 34. The compound, pharmaceutically acceptable salt thereof, solvate thereof, and/or derivative thereof according to any one of clauses 1 to 6 or 30 to 33, wherein $R_{17}$ is at the para-position.

Clause 35. The compound, pharmaceutically acceptable salt thereof, solvate thereof, or derivative thereof according to any one of clauses 1 to 6 or 25 to 34, wherein $R_{18}$ is H.

Clause 36. The compound, pharmaceutically acceptable salt thereof, solvate thereof, or derivative thereof according to any one of clauses 1 to 6 or 25 to 29, wherein $R_{17}$ is H and $R_{18}$ is H.

Clause 37. The compound, pharmaceutically acceptable salt thereof, solvate thereof, or derivative thereof according to clause 36, wherein $R_{16}$ is at the meta-position.

Clause 38. The compound, pharmaceutically acceptable salt thereof, solvate thereof, and/or derivative thereof according to any one of clauses 1 to 6 or 25 to 37, wherein V is:

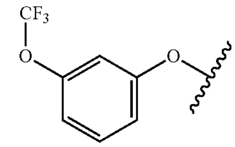

.

Clause 39. The compound, pharmaceutically acceptable salt thereof, solvate thereof, and/or derivative thereof according to any one of clauses 1 to 6 or 25 to 37, wherein V is:

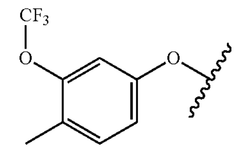

.

Clause 40. The compound, pharmaceutically acceptable salt thereof, solvate thereof, and/or derivative thereof according to any one of clauses 1 to 6 or 25 to 37, wherein V is:

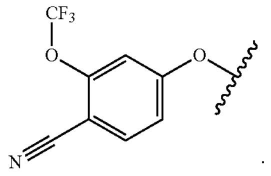 [SMILES: *Oc1ccc(C#N)c(OC(F)(F)F)c1]

Clause 41. The compound, pharmaceutically acceptable salt thereof, solvate thereof, and/or derivative thereof according to any one of clauses 1 to 6 or 25 to 37, wherein V is:

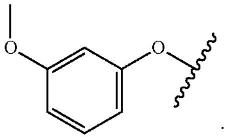 [SMILES: *Oc1cccc(OC)c1]

Clause 42. The compound, pharmaceutically acceptable salt thereof, solvate thereof, and/or derivative thereof according to any one of clauses 1 to 24, wherein V is:

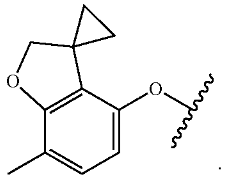

Clause 43. The compound, pharmaceutically acceptable salt thereof, solvate thereof, and/or derivative thereof according to any one of clauses 1 to 24, wherein V is:

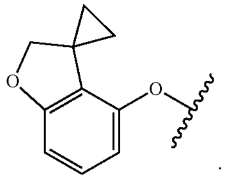 [SMILES: *Oc1cccc2c1C1(CC1)CO2]

Clause 44. The compound, pharmaceutically acceptable salt thereof, solvate thereof, and/or derivative thereof according to any one of clauses 1 to 24, wherein V is:

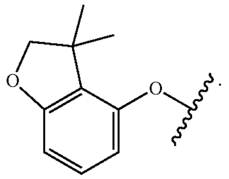 [SMILES: *Oc1cccc2c1C(C)(C)CO2]

Clause 45. The compound, pharmaceutically acceptable salt thereof, solvate thereof, and/or derivative thereof according to any one of clauses 1 to 24, wherein V is:

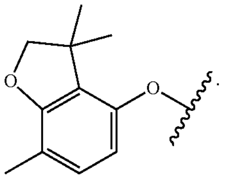 [SMILES: *Oc1ccc(C)c2c1C(C)(C)CO2]

Clause 46. The compound, pharmaceutically acceptable salt thereof, solvate thereof, and/or derivative thereof according to any one of clauses 1 to 45, wherein W is N, and X and Y are CH.

Clause 47. The compound, pharmaceutically acceptable salt thereof, solvate thereof, and/or derivative thereof according to any one of clauses 1 to 45, wherein W is N, X is N and Y is CH.

Clause 48. The compound, pharmaceutically acceptable salt thereof, solvate thereof, and/or derivative thereof according to any one of clauses 1 to 45, wherein W is N, X is CH and Y is N.

Clause 49. The compound, pharmaceutically acceptable salt thereof, solvate thereof, and/or derivative thereof according to any one of clauses 1 to 45, wherein W and X are CH, and Y is N.

Clause 50. The compound, pharmaceutically acceptable salt thereof, solvate thereof, and/or derivative thereof according to any one of clauses 1 to 49, wherein Z is group (Za):

(Za)

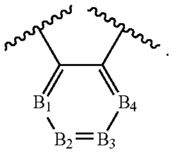

Clause 51. The compound, pharmaceutically acceptable salt thereof, solvate thereof, and/or derivative thereof according to clause 50, wherein $B_1$ is N.

Clause 52. The compound, pharmaceutically acceptable salt thereof, solvate thereof, and/or derivative thereof according to clause 50, wherein $B_2$ is N.

Clause 53. The compound, pharmaceutically acceptable salt thereof, solvate thereof, and/or derivative thereof according to clause 50, wherein $B_3$ is N.

Clause 54. The compound, pharmaceutically acceptable salt thereof, solvate thereof, and/or derivative thereof according to clause 50, wherein $B_4$ is N.

Clause 55. The compound, pharmaceutically acceptable salt thereof, solvate thereof, and/or derivative thereof according to clause 50, wherein (Za) is selected from the group consisting of:

Za1

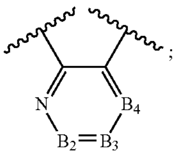

Za2

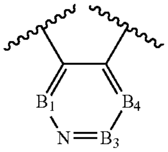

; and

Za3

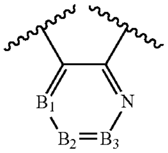

.

Clause 56. The compound, pharmaceutically acceptable salt thereof, solvate thereof, and/or derivative thereof according to clause 50, wherein (Za) is selected from the group consisting of:

Za4

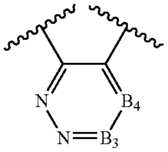

;

Za5

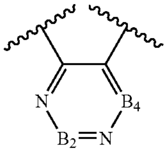

;

Za6

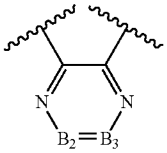

; and

Za7

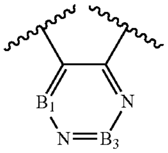

.

Clause 57. The compound, pharmaceutically acceptable salt thereof, solvate thereof, and/or derivative thereof according to clause 55, wherein (Za) is selected from the group consisting of:

Za8

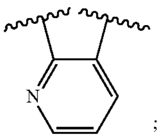

;

Za9

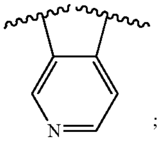

;

Za10

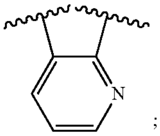

;

Za11

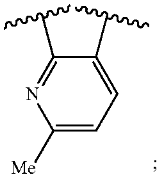

;

Za12

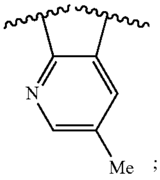

;

Za13

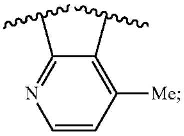

Za9-a

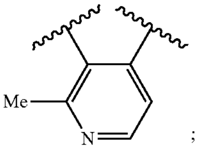

;

Za9-b

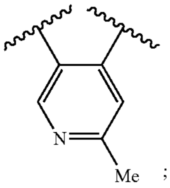

;

Za9-c

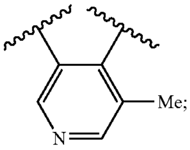

Za18

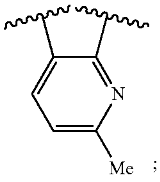

;

-continued

Za19

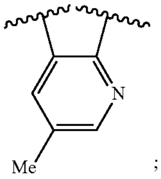

; and

Za20

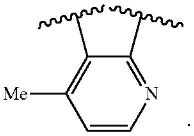

.

Clause 58. The compound, pharmaceutically acceptable salt thereof, solvate thereof, and/or derivative thereof according to clause 56, wherein (Za) is selected from the group consisting of:

Za14

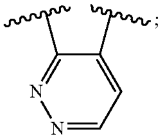

Za14-a

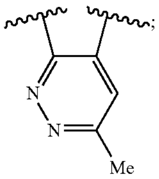

Za14-b

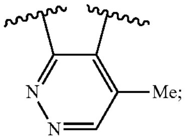

Za15

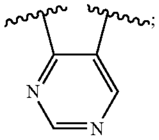

Za16

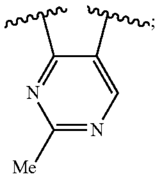

Za16-a

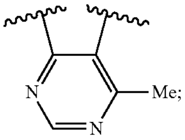

-continued

Za17

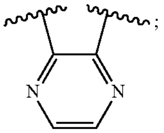

Za17-a

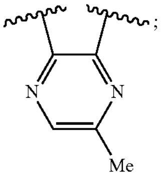

Za17-b

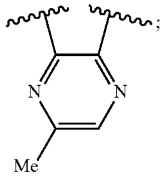

Za21

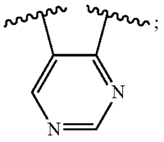

Za22

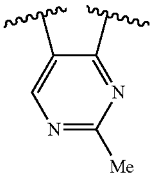

and

Za22-a

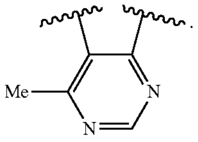

Clause 59. The compound, pharmaceutically acceptable salt thereof, solvate thereof, and/or derivative thereof according to clause 57, wherein (Za) is selected from the group consisting of:

Za8

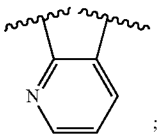

;

Za9

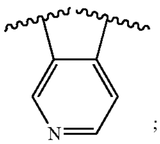

;

-continued

Za10

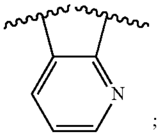

;

Za11

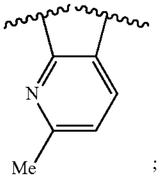

;

Za12

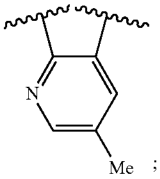

; and

Za13

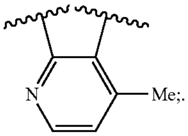

;.

Clause 60. The compound, pharmaceutically acceptable salt thereof, solvate thereof, and/or derivative thereof according to clause 58, wherein (Za) is selected from the group consisting of:

Za15

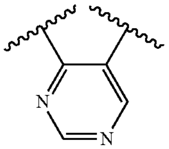

; and

Za16

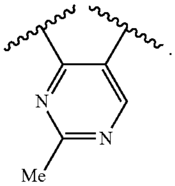

.

Clause 61. The compound, pharmaceutically acceptable salt thereof, solvate thereof, and/or derivative thereof according to clause 59, wherein (Za) is:

Za8

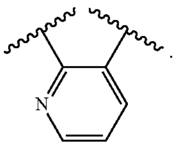

.

Clause 62. The compound, pharmaceutically acceptable salt thereof, solvate thereof, and/or derivative thereof according to clause 60, wherein (Za) is:

Za16

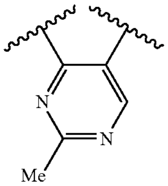

Clause 63. The compound, pharmaceutically acceptable salt thereof, solvate thereof, and/or derivative thereof according to any one of clauses 1 to 49, wherein Z is group (Zb):

(Zb)

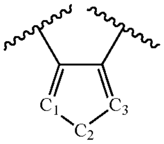

, wherein:

$C_1$ and $C_3$ are each independently selected from CH, C(Me) and N; and $C_2$ is NH or N(Me); and wherein when one of $C_1$ and $C_3$ is N, the other is CH or C(Me).

Clause 64. The compound, pharmaceutically acceptable salt thereof, solvate thereof, and/or derivative thereof according to clause 63, wherein (Zb) is selected from the group consisting of:

Zb1

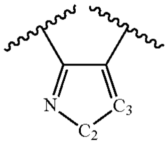

;

Zb2

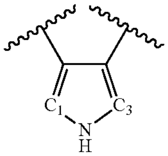

;

Zb3

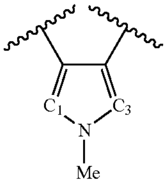

; and

Zb4

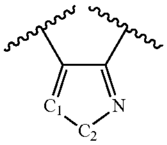

.

Clause 65. The compound, pharmaceutically acceptable salt thereof, solvate thereof, and/or derivative thereof according to clause 63, wherein (Zb) is selected from the group consisting of:

Zb13

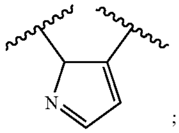

;

Zb14

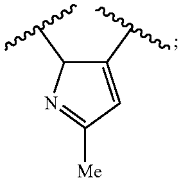

;

Zb15

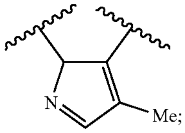

;

Zb16

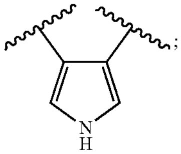

;

Zb17

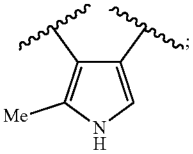

;

Zb18

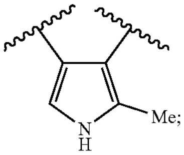

;

Zb19

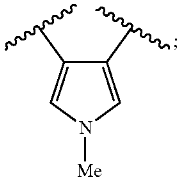

;

Zb20

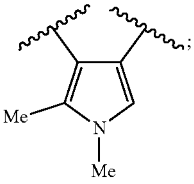

;

Zb21

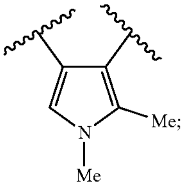

;

-continued

Zb22

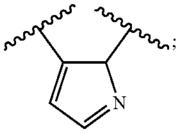

;

Zb23

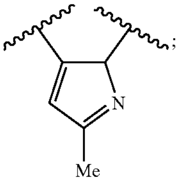

; and

Zb24

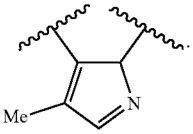

.

Clause 66. The compound, pharmaceutically acceptable salt thereof, solvate thereof, and/or derivative thereof according to clause 63, wherein (Zb) is selected from the group consisting of:

Zb5

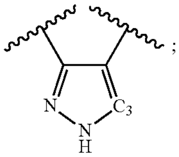

;

Zb6

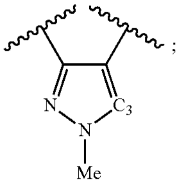

;

Zb7

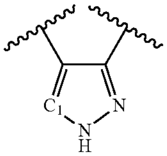

and

Zb8

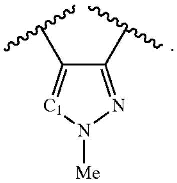

.

Clause 67. The compound, pharmaceutically acceptable salt thereof, solvate thereof, and/or derivative thereof according to clause 66, wherein (Zb) is selected from the group consisting of:

Zb9

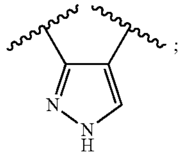

Zb10

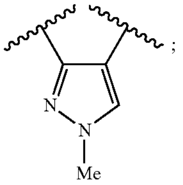

Zb11

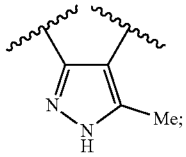

and

Zb12

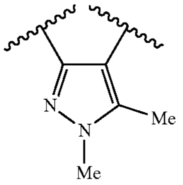

Clause 68. The compound, pharmaceutically acceptable salt thereof, solvate thereof, and/or derivative thereof according to clause 67, wherein (Zb) is:

Zb9

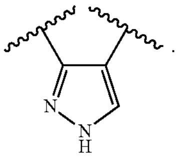

Clause 69. The compound, pharmaceutically acceptable salt thereof, solvate thereof, and/or derivative thereof according to clause 68, wherein (Zb) is:

Zb10

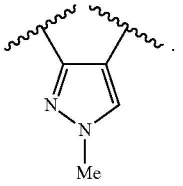

Clause 70. The compound, pharmaceutically acceptable salt thereof, solvate thereof, and/or derivative thereof according to any one of clauses 1 to 49, wherein Z is group (Zc):

Zc

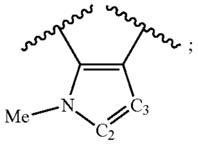

wherein:

$C_2$ is N, CH or C(Me) and $C_3$ is CH or C(Me); wherein when one of $C_2$ or $C_3$ is C(Me), the other is CH.

Clause 71. The compound, pharmaceutically acceptable salt thereof, solvate thereof, and/or derivative thereof according to clause 70, wherein Zc is selected from the group consisting of:

Zc1

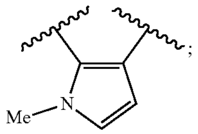

Zc2

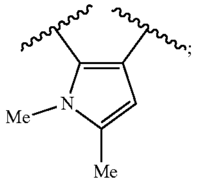

and

Zc3

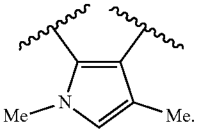

Clause 72. The compound, pharmaceutically acceptable salt thereof, solvate thereof, and/or derivative thereof according to any one of clauses 1 to 49, wherein Z is group (Zd):

Zd

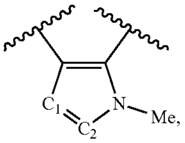

wherein:

$C_1$ is CH or C(Me) and $C_2$ is N, CH or C(Me); wherein when one of $C_1$ or $C_2$ is C(Me), the other is CH.

Clause 73. The compound, pharmaceutically acceptable salt thereof, solvate thereof, and/or derivative thereof according to clause 72, wherein (Zd) is selected from the group consisting of:

Zd1

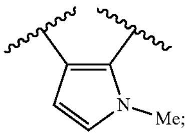

-continued

Zd2

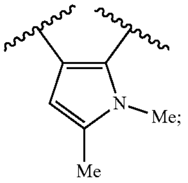

and

Zd3

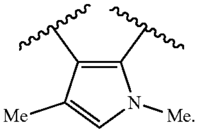

Clause 74. The compound, pharmaceutically acceptable salt thereof, solvate thereof, and/or derivative thereof according to any one of clauses 1 to 49, wherein Z is group (Ze-a):

Ze-a

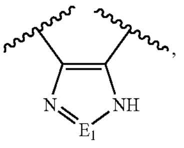

wherein:

$E_1$ is CH or CMe.

Clause 75. The compound, pharmaceutically acceptable salt thereof, solvate thereof, and/or derivative thereof according to clause 74, wherein (Ze-a) is selected from the group consisting of:

Ze-a1

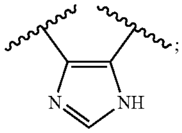

and

Ze-a2

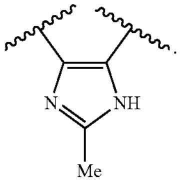

Clause 76. The compound, pharmaceutically acceptable salt thereof, solvate thereof, and/or derivative thereof according to any one of clauses 1 to 49, wherein Z is group (Ze-b):

Ze-b

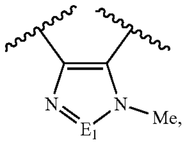

wherein $E_1$ is CH or C(Me).

Clause 77. The compound, pharmaceutically acceptable salt thereof, solvate thereof, and/or derivative thereof according to clause 76, wherein (Ze-b) is selected from the group consisting of:

Ze-b1

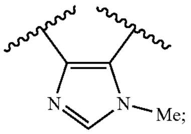

and

Ze-b2

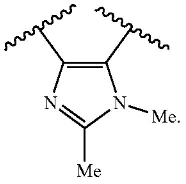

Clause 78. The compound, pharmaceutically acceptable salt thereof, solvate thereof, and/or derivative thereof according to any one of clauses 1 to 49, wherein Z is group (Ze-c):

Ze-c

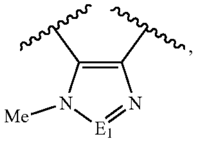

wherein:

$E_1$ is CH or C(Me).

Clause 79. The compound, pharmaceutically acceptable salt thereof, solvate thereof, and/or derivative thereof according to clause 76, wherein (Ze-c) is selected from the group consisting of:

Ze-c1

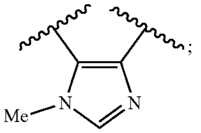

and

Ze-c2

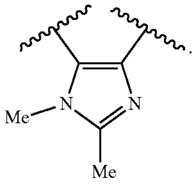

Clause 80. The compound, pharmaceutically acceptable salt thereof, solvate thereof, and/or derivative thereof according to any one of clauses 1 to 6, which is selected from the group consisting of:

3-[6-(7-methylspiro[2H-benzofuran-3,1'-cyclopropane]-4-yl)oxy-3-pyridyl]-1H-imidazo[4,5-b]pyridin-2-one;

7-methyl-3-[6-(7-methylspiro[2H-benzofuran-3,1'-cyclopropane]-4-yl)oxy-3-pyridyl]-1H-imidazo[4,5-b]pyridin-2-one;

3-(6-spiro[2H-benzofuran-3,1'-cyclopropane]-4-yloxy-3-pyridyl)-1H-imidazo[4,5-b]pyridin-2-one;
3-[6-[4-methyl-3-(trifluoromethoxy)phenoxy]-3-pyridyl]-1H-imidazo[4,5-b]pyridin-2-one;
7-methyl-3-(6-spiro[2H-benzofuran-3,1'-cyclopropane]-4-yloxy-3-pyridyl)-1H-imidazo[4,5-b]pyridin-2-one;
3-(5-spiro[2H-benzofuran-3,1'-cyclopropane]-4-yloxy-2-pyridyl)-1H-imidazo[4,5-b]pyridin-2-one;
3-[6-[3-(trifluoromethoxy)phenoxy]-3-pyridyl]-1H-imidazo[4,5-b]pyridin-2-one;
3-(5-spiro[2H-benzofuran-3,1'-cyclopropane]-4-yloxy-pyrazin-2-yl)-1H-imidazo[4,5-b]pyridin-2-one;
3-[5-[(3,3-dimethyl-2H-benzofuran-4-yl)oxy]pyrazin-2-yl]-1H-imidazo[4,5-b]pyridin-2-one;
3-[5-[3-(trifluoromethoxy)phenoxy]pyrazin-2-yl]-1H-imidazo[4,5-b]pyridin-2-one;
3-[5-(7-methylspiro[2H-benzofuran-3,1'-cyclopropane]-4-yl)oxypyrazin-2-yl]-1H-imidazo[4,5-b]pyridin-2-one;
3-[6-[(3,3-dimethyl-2H-benzofuran-4-yl)oxy]-3-pyridyl]-1H-imidazo[4,5-b]pyridin-2-one;
3-(2-{2H-spiro[1-benzofuran-3,1'-cyclopropane]oxy}pyrimidin-5-yl)-1H,2H,3H-imidazo[4,5-b]pyridin-2-one;
4-[[5-(2-oxo-1H-imidazo[4,5-b]pyridin-3-yl)-2-pyridyl]oxy]-2-(trifluoromethoxy)benzonitrile;
7-methyl-3-(2-spiro[2H-benzofuran-3,1'-cyclopropane]-4-yloxypyrimidin-5-yl)-1H-imidazo[4,5-b]pyridin-2-one;
3-[2-(3-methoxyphenoxy)pyrimidin-5-yl]-1H-imidazo[4,5-b]pyridin-2-one;
3-[2-[3-(trifluoromethoxy)phenoxy]pyrimidin-5-yl]-1H-imidazo[4,5-b]pyridin-2-one;
2-methyl-6-(6-spiro[2H-benzofuran-3,1'-cyclopropane]-4-yloxy-3-pyridyl)-4H-imidazo[4,5-c]pyrazol-5-one;
2-methyl-6-[6-(7-methylspiro[2Hbenzofuran-3,1'-cyclopropane]-4-yl)oxy-3-pyridyl]-4H-imidazo[4,5-c]pyrazol-5-one;
6-[6-[(3,3-dimethyl-2H-benzofuran-4-yl)oxy]-3-pyridyl]-2-methyl-4H-imidazo[4,5-c]pyrazol-5-one;
2-methyl-6-(5-spiro[2H-benzofuran-3,1'-cyclopropane]-4-yloxypyrazin-2-yl)-4H-imidazo[4,5-c]pyrazol-5-one;
2-methyl-6-(2-spiro[2H-benzofuran-3,1'-cyclopropane]-4-yloxypyrimidin-5-yl)-4H-imidazo[4,5-c]pyrazol-5-one;
3-[2-[(3,3-dimethyl-2H-benzofuran-4-yl)oxy]pyrimidin-5-yl]-1H-imidazo[4,5-c]pyridin-2-one;
2-methyl-9-[6-[3-(trifluoromethoxy)phenoxy]-3-pyridyl]-7H-purin-8-one;
2-methyl-9-[6-(7-methylspiro[2H-benzofuran-3,1'-cyclopropane]-4-yl)oxy-3-pyridyl]-7H-purin-8-one;
2-methyl-9-(6-spiro[2H-benzofuran-3,1'-cyclopropane]-4-yloxy-3-pyridyl)-7H-purin-8-one;
2-methyl-9-[6-[4-methyl-3-(trifluoromethoxy)phenoxy]-3-pyridyl]-7H-purin-8-one;
9-[6-(3-methoxyphenoxy)-3-pyridyl]-2-methyl-7H-purin-8-one;
9-[6-(7-methylspiro[2H-benzofuran-3,1'-cyclopropane]-4-yl)oxy-3-pyridyl]-7H-purin-8-one;
9-[6-[(3,3-dimethyl-2H-benzofuran-4-yl)oxy]-3-pyridyl]-2-methyl-7H-purin-8-one;
3-[2-(7-methylspiro[2H-benzofuran-3,1'-cyclopropane]-4-yl)oxypyrimidin-5-yl]-1H-imidazo[4,5-b]pyridine-2-one;
3-[2-[4-methyl-3-(trifluoromethoxy)phenoxy]pyrimidin-5-yl]-1H-imidazo[4,5-b]pyridin-2-one;
3-[2-[(3,3-dimethyl-2H-benzofuran-4-yl)oxy]pyrimidin-5-yl]-1H-imidazo[4,5-b]pyridin-2-one;
6-(6-spiro[2H-benzofuran-3,1'-cyclopropane]-4-yloxy-3-pyridyl)-2,4-dihydroimidazo[4,5-c]pyrazol-5-one;
3-[6-(7-methylspiro[2H-benzofuran-3,1'-cyclopropane]-4-yl)oxy-3-pyridyl]-1H-imidazo[4,5-c]pyridin-2-one;
1-(6-spiro[2H-benzofuran-3,1'-cyclopropane]-4-yloxy-3-pyridyl)-3H-imidazo[4,5-b]pyridin-2-one;
5-methyl-3-(5-spiro[2H-benzofuran-3,1'-cyclopropane]-4-yloxypyrazin-2-yl)-1H-imidazo[4,5-b]pyridin-2-one;
6-methyl-3-(5-spiro[2H-benzofuran-3,1'-cyclopropane]-4-yloxypyrazin-2-yl)-1H-imidazo[4,5-b]pyridin-2-one; and
3-[2-[(3,3,7-trimethyl-2H-benzofuran-4-yl)oxy]pyrimidin-5-yl]-1H-imidazo[4,5-b]pyridin-2-one.

Clause 81. The compound, pharmaceutically acceptable salt thereof, solvate thereof, and/or derivative thereof according to any one of clauses 1 to 6, which is 3-(2-{2H-spiro[1-benzofuran-3,1'-cyclopropane]oxy}pyrimidin-5-yl)-1H,2H,3H-imidazo[4,5-b]pyridin-2-one:

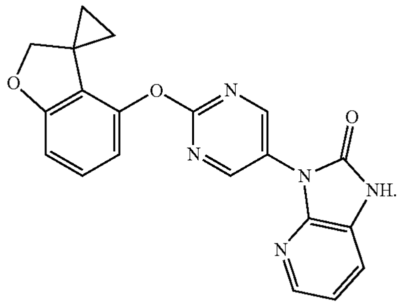 [SMILES: O=c1[nH]c2cccnc2n1-c1cnc(Oc2cccc3c2C2(CC2)CO3)nc1]

Clause 82. The compound, pharmaceutically acceptable salt thereof, solvate thereof, and/or derivative thereof according to any one of clauses 1 to 6, which is 3-[2-[3-(trifluoromethoxy)phenoxy]pyrimidin-5-yl]-1H-imidazo[4,5-b]pyridin-2-one:

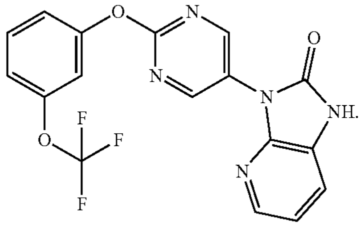 [SMILES: O=c1[nH]c2cccnc2n1-c1cnc(Oc2cccc(OC(F)(F)F)c2)nc1]

Clause 83. The compound, pharmaceutically acceptable salt thereof, solvate thereof, and/or derivative thereof according to any one of clauses 1 to 6 which is 2-methyl-9-[6-[3-(trifluoromethoxy)phenoxy]-3-pyridyl]-7H-purin-8-one:

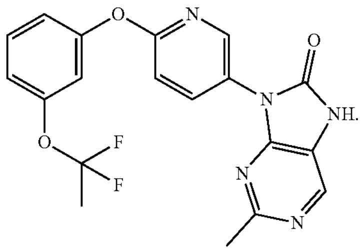 [SMILES: Cc1ncc2[nH]c(=O)n(-c3ccc(Oc4cccc(OC(C)(F)F)c4)nc3)c2n1]

Clause 84. The compound, pharmaceutically acceptable salt thereof, solvate thereof, and/or derivative thereof according to any one of clauses 1 to 6 which is 3-[2-[(3,3-dimethyl-2H-benzofuran-4-yl)oxy]pyrimidin-5-yl]-1H-imidazo[4,5-b]pyridin-2-one:

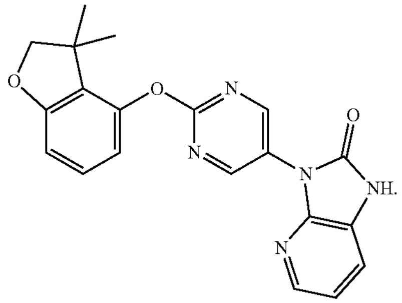 [SMILES: CC1(C)COc2cccc(Oc3ncc(-n4c(=O)[nH]c5cccnc54)cn3)c21]

Clause 85. The compound according to any one of clauses 81 to 84, wherein the compound is in the form of a pharmaceutically acceptable salt.

Clause 86. The compound according to any one of clauses 81 to 84, wherein the compound is not in the form of a salt.

Clause 87. A pharmaceutical composition comprising the compound, pharmaceutically acceptable salt thereof, solvate thereof, and/or derivative thereof according to any one of clauses 1 to 86 and a pharmaceutically acceptable carrier or excipient.

Clause 88. The compound, pharmaceutically acceptable salt thereof, solvate thereof, and/or derivative thereof according to any one of clauses 1 to 86 or the pharmaceutical composition according to clause 87 for use as a medicament.

Clause 89. The compound, pharmaceutically acceptable salt thereof, solvate thereof, and/or derivative thereof according to any one of clauses 1 to 86 or the pharmaceutical composition for use according to clause 87 for use in the prophylaxis or treatment of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Ménière's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease.

Clause 90. The compound, pharmaceutically acceptable salt thereof, solvate thereof, and/or derivative thereof according to any one of clauses 1 to 86 or the pharmaceutical composition for use according to clause 87 for use in the prophylaxis or treatment of progressive myoclonic epilepsy, including PME associated with mutations in the KCNC1 gene, hearing disorders, including hearing loss and tinnitus, Fragile X syndrome, schizophrenia, substance abuse disorders, or pain.

Clause 91. Use of a compound, pharmaceutically acceptable salt thereof, solvate thereof, and/or derivative thereof according to any one of clauses 1 to 86 or the pharmaceutical composition for use according to clause 87 in the manufacture of a medicament.

Clause 92. Use of according to clause 91, in the manufacture of a medicament for the prophylaxis or treatment of progressive myoclonic epilepsy, including PME associated with mutations in the KCNC1 gene, hearing disorders, including hearing loss and tinnitus, Fragile X syndrome, schizophrenia, substance abuse disorders, or pain.

Clause 93. A method for the prophylaxis or treatment of progressive myoclonic epilepsy, including PME associated with mutations in the KCNC1 gene, hearing disorders, including hearing loss and tinnitus, Fragile X syndrome, schizophrenia, substance abuse disorders, or pain, said method comprising administering a compound, pharmaceutically acceptable salt thereof, solvate thereof, and/or derivative thereof according to any one of clauses 1 to 86 or the pharmaceutical composition for use according to clause 87 to a subject.

Clause 94. The compound, pharmaceutically acceptable salt thereof, solvate thereof, and/or derivative thereof, the pharmaceutical composition, use or method according to according to any one of clauses 1 to 93, for use in the prophylaxis or treatment of progressive myoclonic epilepsy.

Clause 95. The compound, pharmaceutically acceptable salt thereof, solvate thereof, and/or derivative thereof, the pharmaceutical composition, use or method according to according to any one of clauses 1 to 91, for use in the prophylaxis or treatment of progressive myoclonic epilepsy associated with mutations in the KCNC1 gene.

Clause 96. The compound, pharmaceutically acceptable salt thereof, solvate thereof, and/or derivative thereof, the pharmaceutical composition, use or method according to according to to clause 94, for use in the prophylaxis or treatment of juvenile progressive myoclonic epilepsy.

Clause 97. The compound, pharmaceutically acceptable salt thereof, solvate thereof, and/or derivative thereof, the pharmaceutical composition, use or method according to according to any one of clauses 1 to 93, for use in the prophylaxis or treatment of hearing loss.

Clause 98. The compound, pharmaceutically acceptable salt thereof, solvate thereof, and/or derivative thereof, the pharmaceutical composition, use or method according to according to any one of clauses 1 to 93, for use in the prophylaxis or treatment of tinnitus.

Clause 99. The compound, pharmaceutically acceptable salt thereof, solvate thereof, and/or derivative thereof, the pharmaceutical composition, use or method according to according to any one of clauses 1 to 93, for use in the prophylaxis or treatment of Fragile X syndrome.

Clause 100. The compound, pharmaceutically acceptable salt thereof, solvate thereof, and/or derivative thereof, the pharmaceutical composition, use or method according to according to any one of clauses 1 to 93, for use in the prophylaxis or treatment of schizophrenia.

Clause 101. The compound, pharmaceutically acceptable salt thereof, solvate thereof, and/or derivative thereof, the pharmaceutical composition, use or method according to according to any one of clauses 1 to 93, for use in the prophylaxis or treatment of substance abuse disorders.

Clause 102. The compound, pharmaceutically acceptable salt thereof, solvate thereof, and/or derivative thereof, the pharmaceutical composition, use or method according to according to any one of clauses 1 to 93, for use in the prophylaxis or treatment of pain, such as neuropathic pain, inflammatory pain or miscellaneous pain.

Clause 103. The compound, pharmaceutically acceptable salt thereof, solvate thereof, and/or derivative thereof, the pharmaceutical composition, use or method according to according to any one of clauses 1 to 102, for use in prophylaxis.

Clause 104. The compound, pharmaceutically acceptable salt thereof, solvate thereof, and/or derivative thereof, the pharmaceutical composition, use or method according to according to any one of clauses 1 to 103, for use in treatment.

Clause 105. The derivative according to any one of clauses 1 to 104, functionalised at the secondary nitrogen of the urea with a group L, wherein L is selected from:

—$PO(OH)O^{-}\cdot M^{+}$, wherein $M^{+}$ is a pharmaceutically acceptable monovalent counterion,

—$PO(O^{-})_2.2M^{+}$,

—$PO(O^{-})_2\cdot D^{2+}$, wherein $D^{2+}$ is a pharmaceutically acceptable divalent counterion, —$CH(R^{X})$—$PO(OH)O^{-}\cdot M^{+}$, wherein $R^{X}$ is hydrogen or $C_{1-3}$ alkyl,

—$CH(R^{X})$—$PO(O^{-})_2.2M^{+}$,

—$CH(R^{X})$—$PO(O^{-})_2\cdot D^{2+}$, and

—CO—$CH_2CH_2$—$CO_2\cdot M^{+}$.

Clause 106. The compound, pharmaceutically acceptable salt thereof, solvate thereof, and/or derivative thereof, the pharmaceutical composition, use or method according to according to any one of clauses 1 to 105, for use in a human.

Clause 107. The compound, pharmaceutically acceptable salt thereof, solvate thereof, and/or derivative thereof, the pharmaceutical composition, use or method according to according to clause 106, for use in a human of less than 18 years of age.

Clause 108. The compound, pharmaceutically acceptable salt thereof, solvate thereof, and/or derivative thereof, the pharmaceutical composition, use or method according to according to clause 107, for use in a human 4 to 17 years old.

Clause 109. The compound, pharmaceutically acceptable salt thereof, solvate thereof, and/or derivative thereof, the pharmaceutical composition, use or method according to according to clause 106, for use in a human aged 18 to 65.

Clause 110. The compound, pharmaceutically acceptable salt thereof, solvate thereof, and/or derivative thereof, the pharmaceutical composition, use or method according to according to clause 106, for use in a human aged 66 years old or older.

Clause 111. The compound, pharmaceutically acceptable salt thereof, solvate thereof, and/or derivative thereof, the pharmaceutical composition, use or method according to according to any one of clauses 1 to 110, for administration at 5 to 250 mg per day.

Clause 112. The compound, pharmaceutically acceptable salt thereof, solvate thereof, and/or derivative thereof, the pharmaceutical composition, use or method according to according to any one of clauses 1 to 111, for administration for a period of at least three months.

Clause 113. A compound or salt thereof selected from the group consisting of:

a compound of formula (II):

(II)

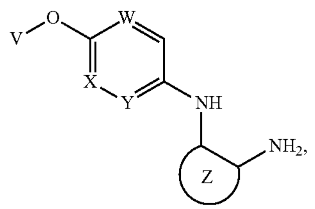

wherein V, W, X, Y and Z, $B_1$, B2, $B_3$ and $B_4$ are as defined for the compound of formula (I);

a compound of formula (III):

(III)

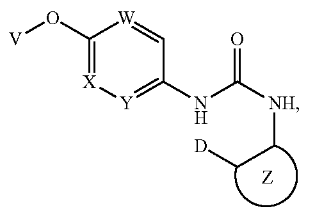

wherein V, W, X, Y and Z are as defined for the compound of formula (I) and D is halo, such as Cl, Br or I;

a compound of formula (IV):

(IV)

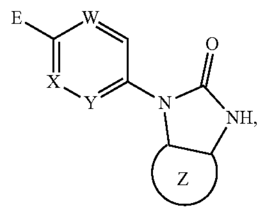

wherein W, X, Y and Z are as defined for the compound of formula (I) and E is halo, such as F or Cl;

a compound of formula (VI):

(VI)

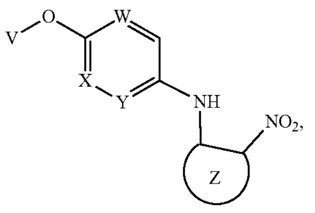

wherein V, W, X, Y and Z are as defined for the compound of formula (I);

a compound of formula (IX):

(IX)

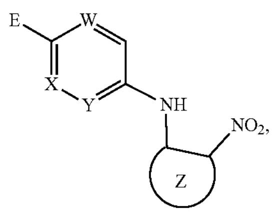

wherein W, X, Y and Z are as defined for the compound of formula (I) and E is halo, such as F or Cl;

a compound of formula (X):

(X)

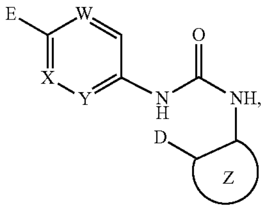

wherein W, X, Y and Z are as defined for the compound of formula (I), E is halo, such as F or Cl and D is halo, such as Cl, Br or I; and a compound of formula (XIII):

(XIII)

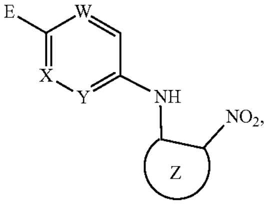

wherein W, X, Y and Z are as defined for the compound of formula (I) and E is halo, such as F or Cl;

or a salt thereof, such as a pharmaceutically acceptable salt thereof.

Clause 114. A process for the preparation of a compound of formula (I), or a pharmaceutically acceptable salt and/or solvate and/or derivative thereof, which comprises reacting a compound of formula (II):

(II)

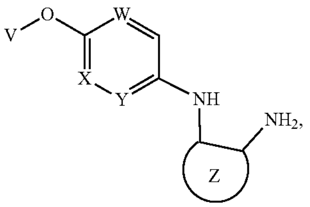

or a salt thereof, wherein V, W, X, Y and Z are as defined for the compound of formula (I), with a carbonylating agent such a triphosgene or carbonyldiimidazole.

Clause 115. A process for the preparation of a compound of formula (I), or a pharmaceutically acceptable salt and/or solvate and/or derivative thereof, which comprises reacting a compound of formula (III):

(III)

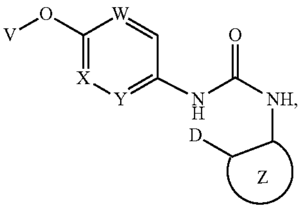

or a salt thereof, wherein V, W, X, Y and Z are as defined for the compound of formula (I), and D is halo, such as Cl, Br or I, under metal catalysed cross-coupling conditions.

Clause 116. A process for the preparation of a compound of formula (I), or a pharmaceutically acceptable salt and/or solvate and/or derivative thereof, which comprises reacting a compound of formula (III):

(IV)

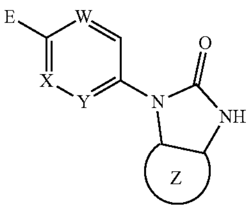

or a salt thereof, wherein W, X, Y and Z are as defined for the compound of formula (I), and E is halo, such as F or Cl, with a compound of formula (V):

(V)

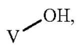

or a salt thereof, wherein V is as defined in claim 1.

Clause 117. A process for the preparation for a compound of formula (II), or a salt thereof, which comprises reacting a compound of formula (VI):

(VI)

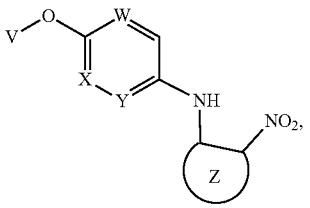

or a salt thereof, wherein V, W, X, Y and Z are as defined for the compound of formula (I), under reduction conditions (e.g. in the presence of Fe powder and ammonium chloride).

Clause 118. A process for the preparation of a compound of formula (III), or a salt thereof, which comprises reacting a compound of formula (VII):

(VII)

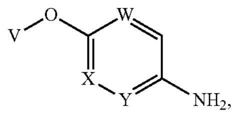

or a salt thereof, wherein V, W, X and Y are as defined for the compound of formula (I), with a compound of formula (VIII):

(VIII)

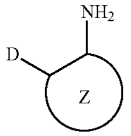

or a salt thereof, wherein Z is as defined for the compound of formula (I) and D is halo, such as Cl, Br or I.

Clause 119. A process for the preparation of a compound of formula (IV), or a salt thereof, which comprises reacting a compound of formula (IX):

(IX)

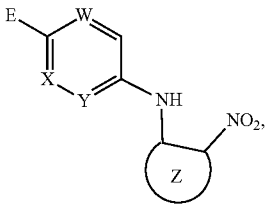

or a salt thereof, wherein W, X, Y and Z are as defined for the compound of formula (I) and E is halo, such as Cl or F, with a carbonylating agent such a triphosgene or carbonyldiimidazole.

Clause 120. A process for the preparation of a compound of formula (IV), or a salt thereof, which comprises reacting a compound of formula (X):

(X)

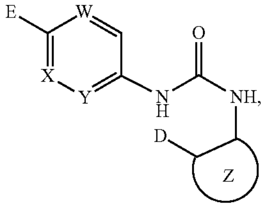

or a salt thereof, wherein W, X, Y and Z are as defined for the compound of formula (I), E is halo, such as F or Cl and D is halo, such as Cl, Br or I, under metal catalysed cross-coupling conditions.

Clause 121. A process for the preparation of a compound of formula (VI), or a salt thereof, which comprises reacting a compound of formula (VII):

(VII)

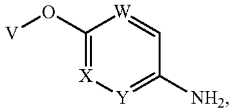

or a salt thereof, wherein V, W, X and Y are as defined for the compound of formula (I), with a compound of formula (XI):

(XI)

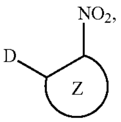

or a salt thereof, wherein Z is as defined for the compound of formula (I) and D is halo, such Cl, Br or I.

Clause 122. A process for the preparation of a compound of formula (IX), or a salt thereof, which comprises reacting a compound of formula (XIII):

(XIII)

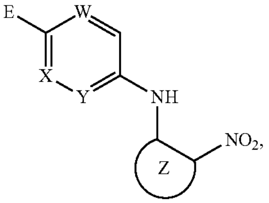

or a salt thereof, wherein W, X, Y and Z are as defined for the compound of formula (I) and E is halo, such as F or Cl, under reduction conditions (e.g. in the presence of Fe powder and ammonium chloride).

Clause 123. A process for the preparation of a compound of formula (X), or a salt thereof, which comprises reacting a compound of formula (XIV):

(XIV)

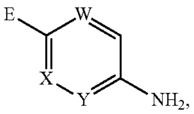

or a salt thereof, wherein W, X and Y are as defined for the compound of formula (I) and E is halo, such as F or Cl, with a compound of formula (VIII):

(VIII)

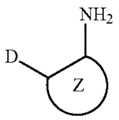

or a salt thereof, wherein Z is as defined in clause 1 and D is halo, such as Cl, Br or I.

Clause 124. A process for the preparation of a compound of formula (IX), or a salt thereof, which comprises reacting a compound of formula (XIV):

(XIV)

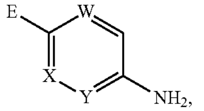

or a salt thereof, wherein W, X and Y are as defined for the compound of formula (I) and E is halo, such as F or Cl, with a compound of formula (XI):

(XI)

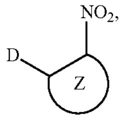

or a salt thereof, wherein Z is as defined for the compound of formula (I) and D is halo, such as Cl, Br or I.

REFERENCES

All publications, including but not limited to patents and patent applications, cited in this specification are herein incorporated by reference as if each individual publication were specifically and individually indicated to be incorporated by reference herein as though fully set forth.

Anderson L A et al. Increased spontaneous firing rates in auditory midbrain following noise exposure are specifically abolished by a Kv3 channel modulator. *Hear Res.* 2018 August;365:77-89 Andrade-Talavera et al., J. Physiol. (2020) 598, 3711-3725

Aroniadou-Anderjaska V et al. Mechanisms regulating GABAergic inhibitory transmission in the basolateral amygdala: implications for epilepsy and anxiety disorders. *Amino Acids* 2007 August;32:305-315.

Baranauskas G, Nistri A. Sensitization of pain pathways in the spinal cord: cellular mechanisms. *Prog. Neurobiol.* 1998 February;54(3):349-65.

Baron R et al. Peripheral input and its importance for central sensitization. *Ann. Neurol.* 2013 November; 74(5):630-6.

Ben-Ari Y. Seizure Beget Seizure: The Quest for GABA as a Key Player. *Crit. Rev. Neurobiol.* 2006;18(1-2): 135-144.

Benes F M et al. Circuitry-based gene expression profiles in GABA cells of the trisynaptic pathway in schizophrenics versus bipolars. *PNAS* 2008 December; 105(52):20935-20940.

Bennett D L, Woods C G. Painful and painless channelopathies. *Lancet Neurol.* 2014 June;13(6):587-99.

Berge S et al. Pharmaceutical Salts. *J. Pharm. Sci.* 1977; 66;1-19.

Boddum et al., Neuropharm. (2017) 118, 102-112

Brambilla P et al. GABAergic dysfunction in mood disorders. *Mol. Psych.* 2003 April;8:721-737.

Brooke R E et al. Spinal cord interneurones labelled transneuronally from the adrenal gland by a GFP-herpes virus construct contain the potassium channel subunit Kv3.1b. *Auton. Neurosci.* 2002 June;98(1-2):45-50.

Brooke R E et al. Association of potassium channel Kv3.4 subunits with pre- and post-synaptic structures in brainstem and spinal cord. *Neuroscience* 2004; 126(4): 1001-10.

Brooke R E et al. Immunohistochemical localisation of the voltage gated potassium ion channel subunit Kv3.3 in the rat medulla oblongata and thoracic spinal cord. *Brain Res.* 2006 January;1070(1):101-15.

Cervero F. Spinal cord hyperexcitability and its role in pain and hyperalgesia. *Exp. Brain Res.* 2009 June; 196(1): 129-37.

Chambers A R et al. Pharmacological modulation of Kv3.1 mitigates auditory midbrain temporal processing deficits following auditory nerve damage. *Sci Rep.* 2017 Dec. 13;7(1): 17496

Chang S Y et al. Distribution of Kv3.3 Potassium Channel Subunits in Distinct Neuronal Populations of Mouse Brain. *J. Comp. Neuro.* 2007 February;502:953-972.

Chien L Y et al. Reduced expression of A-type potassium channels in primary sensory neurons induces mechanical hypersensitivity. *J. Neurosci.* 2007 September;27(37): 9855-65.

Chow A et al. $K^+$ Channel Expression Distinguishes Subpopulations of Parvalbumin- and Somatostatin-Containing Neocortical Interneurons. *J. Neurosci.* 1999 November; 19(21): 9332-9345. Darnell et al., *Cell* 2001, 107, 489-499

Desai R et al. Protein Kinase C Modulates Inactivation of Kv3.3 Channels. *J. Biol. Chem.* 2008;283;22283-22294.

Deuchars S A et al. Properties of interneurones in the intermediolateral cell column of the rat spinal cord: role of the potassium channel subunit Kv3.1. *Neuroscience* 2001; 106(2):433-46.

Devulder J. Flupirtine in pain management: pharmacological properties and clinical use. *CNS Drugs* 2010 October; 24(10):867-81.

Dib-Hajj S D et al. The Na(V) 1.7 sodium channel: from molecule to man. *Nat. Rev. Neurosci.* 2013 January; 14(1):49-62.

Diochot S et al. Sea Anemone Peptides with a Specific Blocking Activity against the Fast Inactivating Potassium Channel Kv3.4. *J. Biol. Chem.* 1998 March;273(12); 6744-6749.

Engel A K et al. Dynamic Predictions: Oscillations and Synchrony in Top-Down Processing. *Nat. Rev. Neurosci.* 2001 October;2(10):704-716.

El-Hassar et al., J Neurosci. 2019 39, 4797-4813

Espinosa F et al. Alcohol Hypersensitivity, Increased Locomotion, and Spontaneous Myoclonus in Mice Lacking the Potassium Channels Kv3.1 and Kv3.3. *J. Neurosci.* 2001 September;21(17):6657-6665.

Espinosa F et al. Ablation of Kv3.1 and Kv3.3 Potassium Channels Disrupts Thalamocortical Oscillations In Vitro and In Vivo. *J. Neurosci.* 2008 May; 28(21):5570-5581.

Figueroa K et al. KCNC3: phenotype, mutations, channel biophysics—a study of 260 familial ataxia patients. *Human Mutation.* 2010; 31; 191-196.

Finnerup N B et al. Pharmacotherapy for neuropathic pain in adults: a systematic review and meta-analysis. *Lancet Neurol.* 2015 February; 14(2): 162-73.

Fisahn A. Kainate receptors and rhythmic activity in neuronal networks: hippocampal gamma oscillations as a tool. *J. Physiol.* 2005 October;561(1):65-72.

Glait L et al. Effects of AUT00063, a Kv3.1 channel modulator, on noise-induced hyperactivity in the dorsal cochlear nucleus. *Hear Res.* 2018 April;361:36-44

Greene T W, Wuts, P G. Greene's *Protective Groups in Organic Synthesis,* 2006, 4th Edition, John Wiley & Sons, Inc., Hoboken, NJ, USA.

Joho R H et al. Increased γ- and Decreased δ-Oscillations in a Mouse Deficient for a Potassium Channel Expressed in Fast-Spiking Interneurons. *J. Neurophysiol.* 1999 June; 82: 1855-1864.

Joho R H, Hurlock E C. The Role of Kv3-type Potassium Channels in Cerebellar Physiology and Behavior. *Cerebellum* 2009 February;8:323-333.

Jung D et al. Age-related changes in the distribution of Kv1.1 and Kv3.1 in rat cochlear nuclei. *Neurol. Res.* 2005;27;436-440.

Kasten M R et al. Differential regulation of action potential firing in adult murine thalamocortical neurons by Kv3.2, Kv1, and SK potassium and N-type calcium channels. *J. Physiol.* 2007; 584(2):565-582.

Kaczmarek L et al. Regulation of the timing of MNTB neurons by short-term and long-term modulation of potassium channels. *Hearing Res.* 2005;206; 133-145.

Lau D et al. Impaired Fast-Spiking, Suppressed Cortical Inhibition, and Increased Susceptibility to Seizures in Mice Lacking Kv3.2 $K^+$ Channel Proteins. *J. Neurosci.* 2000 December; 20(24):9071-9085.

Leger et al., European Neuropsychopharmacology Volume 25, Supplement 2, September 2015, Page S480

Li W et al. Localization of Two High-Threshol Potassium Channel Subunits in the Rat Central Auditory System. *J. Comp. Neuro.* 2001 May;437:196-218.

Lu R et al. Slack channels expressed in sensory neurons control neuropathic pain in mice. *J. Neurosci.* 2015 January;35(3): 1125-35.

Markram H et al. Interneurons of the neocortical inhibitory system. *Nat. Rev. Neurosci.* 2004 October;5:793-807.

Martina M et al. Functional and Molecular Differences between Voltage-Gated $K^+$ Channels of Fast-Spiking Interneurons and Pyramidal Neurons of Rat Hippocampus. *J. Neurosci.* 1998 October; 18(20):8111-8125.

McCarberg B H et al. The impact of pain on quality of life and the unmet needs of pain management: results from pain sufferers and physicians participating in an Internet survey. *Am. J. Ther.* 2008 July-August; 15(4):312-20.

McDonald A J, Mascagni F. Differential expression of Kv3.1b and Kv3.2 potassium channel subunits in interneurons of the basolateral amygdala. *Neuroscience* 2006; 138:537-547.

McMahon A et al. Allele-dependent changes of olivocerebellar circuit properties in the absence of the voltage-gated potassium channels Kv3.1 and Kv3.3. *Eur. J. Neurosci.* 2004 March; 19:3317-3327.

Muona M, et al. A recurrent de novo mutation in KCNC1 causes progressive myoclonus epilepsy. *Nat Genet.* 2015 January;47(1):39-46.

Muqeem T et al. Regulation of Nociceptive Glutamatergic Signaling by Presynaptic Kv3.4 Channels in the Rat Spinal Dorsal Horn *J Neurosci.* 2018 Apr. 11;38(15): 3729-3740

Olsen T et al. Kv3 K+ currents contribute to spike-timing in dorsal cochlear nucleus principal cells. *Neuropharmacology* 2018 May 1; 133:319-333

Parekh et al., Neuropsychopharmacology volume 43, pages 435-444 (2018)

Pilati N et al. Acoustic over-exposure triggers burst firing in dorsal cochlear nucleus fusiform cells. *Hearing Research* 2012; 283;98-106.

Pirbhoy et al., Journal of Neurochemistry 2020 Volume 155, Issue 5 Pages 538-558

Puente N et al. Precise localization of the voltage-gated potassium channel subunits Kv3.1b and Kv3.3 revealed in the molecular layer of the rat cerebellar cortex by a pre-embedding immunogold method. *Histochem. Cell. Biol.* 2010 September; 134:403-409.

Reynolds G P et al. Calcium Binding Protein Markers of GABA Deficits in Schizophrenia-Post Mortem Studies and Animal Models. *Neurotox. Res.* 2004 February;6(1): 57-62.

Ritter D M et al. Modulation of Kv3.4 channel N-type inactivation by protein kinase C shapes the action potential in dorsal root ganglion neurons. *J. Physiol.* 2012 January;590 (Pt 1): 145-61.

Ritter D M et al. Dysregulation of Kv3.4 channels in dorsal root ganglia following spinal cord injury. *J. Neurosci.* 2015 January;35(3): 1260-73.

Roberts L et al. Ringing Ears: The Neuroscience of Tinnitus. *J. Neurosci.* 2010:30(45); 14972-14979.

Rudy B, McBain C J. Kv3 channels: voltage-gated $K^+$ channels designed for high-frequency repetitive firing. *TRENDS* in *Neurosci.* 2001 September;24(9):517-526.

Sacco T et al. Properties and expression of Kv3 channels in cerebellar Purkinje cells. *Mol. Cell. Neurosci.* 2006 July; 33:170-179.

Schulz P, Steimer T. Neurobiology of Circadian Systems. *CNS Drugs* 2009; 23 (Suppl. 2):3-13.

Song P et al. Acoustic environment determines phosphorylation state of the Kv3.1 potassium channel in auditory neurons *Nat. Neurosci.* 2005 October;8(10): 1335-1342.

Spencer K M et al. Neural synchrony indexes disordered perception and cognition in schizophrenia. *PNAS* 2004 December;101(49): 17288-17293.

Strumbos et al., J Neurosci. 2010 30, 10263-10271

Sun S et al. Inhibitors of voltage-gated sodium channel Nav1.7: patent applications since 2010. *Pharm. Pat. Anal.* 2014 September;3(5):509-21

U.S. Department of Health and Human Services, Food and Drug Administration. Draft Guidance for Industry Analgesic Indications: Developing Drug and Biological Products: http://www.fda.gov/downloads/drugs/guidancecompliceregulatoryinformation/quidances/ucm384691.pdf 2014 February von Hehn C et al. Loss of Kv3.1 Tonotopicity and Alterations in cAMP Response Element-Binding Protein Signaling in Central Auditory Neurons of Hearing Impaired Mice. *J. Neurosci.* 2004;24: 1936-1940.

Wickenden A D, McNaughton-Smith G. Kv7 channels as targets for the treatment of pain. *Curr. Pharm. Des.* 2009; 15(15): 1773-98.

Woolf C J. What is this thing called pain? *J. Clin. Invest.* 2010 November; 120(11):3742-4.

Woolf C J. Central sensitization: implications for the diagnosis and treatment of pain. *Pain* 2011 March; 152 (3 Suppl):S2-15.

Yanagi M et al. Kv3.1-containing K(+) channels are reduced in untreated schizophrenia and normalized with antipsychotic drugs. *Mol Psychiatry.* 2014. 19(5):573-9.

Yeung S Y M et al. Modulation of Kv3 Subfamily Potassium Currents by the Sea Anemone Toxin BDS: Significance for CNS and Biophysical Studies. *J. Neurosci.* 2005 March;25(38):8735-8745.

Zamponi G W et al. The Physiology, Pathology, and Pharmacology of Voltage-Gated Calcium Channels and Their Future Therapeutic Potential *Pharmacol Rev.* 2015 October; 67(4):821-70.

The invention claimed is:

1. A compound of 3-[2-[3-(trifluoromethoxy)phenoxy]pyrimidin-5-yl]-1H-imidazo[4,5-b]pyridin-2-one:

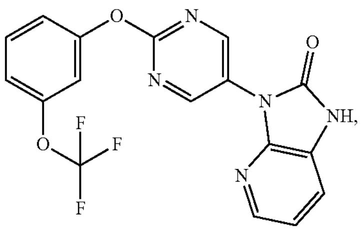 [SMILES: O=c1[nH]c2cccnc2n1-c1cnc(Oc2cccc(OC(F)(F)F)c2)nc1]

or a salt and/or solvate thereof.

2. A compound which is 3-[2-[3-(trifluoromethoxy)phenoxy]pyrimidin-5-yl]-1H-imidazo[4,5-b]pyridin-2-one:

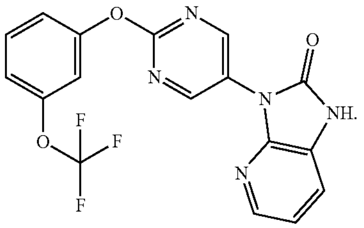 [SMILES: O=c1[nH]c2cccnc2n1-c1cnc(Oc2cccc(OC(F)(F)F)c2)nc1]

3. A salt of 3-[2-[3-(trifluoromethoxy)phenoxy]pyrimidin-5-yl]-1H-imidazo[4,5-b]pyridin-2-one:

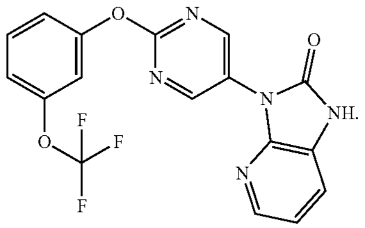 [SMILES: O=c1[nH]c2cccnc2n1-c1cnc(Oc2cccc(OC(F)(F)F)c2)nc1]

4. The salt of claim 3, wherein the salt is a pharmaceutically acceptable salt of 3-[2-[3-(trifluoromethoxy)phenoxy]pyrimidin-5-yl]-1H-imidazo[4,5-b]pyridin-2-one:

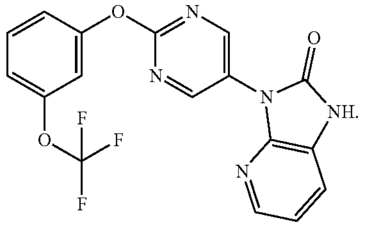 [SMILES: O=c1[nH]c2cccnc2n1-c1cnc(Oc2cccc(OC(F)(F)F)c2)nc1]

* * * * *